US012796631B2

(12) United States Patent
Hirai et al.

(10) Patent No.: US 12,796,631 B2
(45) Date of Patent: Nov. 17, 2026

(54) REBAUDIOSIDE D-RICH STEVIA PLANT

(71) Applicant: SUNTORY HOLDINGS LIMITED, Osaka (JP)

(72) Inventors: Tadayoshi Hirai, Kyoto (JP); Kazunari Iwaki, Kanagawa (JP); Kentaro Ochiai, Kyoto (JP); Saori Takeyama, Kanagawa (JP); Katsuro Miyagawa, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 302 days.

(21) Appl. No.: 17/924,507

(22) PCT Filed: May 11, 2021

(86) PCT No.: PCT/JP2021/017953

§ 371 (c)(1),
(2) Date: Nov. 10, 2022

(87) PCT Pub. No.: WO2021/230256

PCT Pub. Date: Nov. 18, 2021

(65) Prior Publication Data

US 2023/0172136 A1 Jun. 8, 2023

(30) Foreign Application Priority Data

May 12, 2020 (JP) ................................ 2020-084126

(51) Int. Cl.

| | |
|---|---|
| ***A01H 6/14*** | (2018.01) |
| ***A23L 2/60*** | (2006.01) |
| ***A23L 27/00*** | (2016.01) |
| ***A61K 36/28*** | (2006.01) |
| ***C07K 14/415*** | (2006.01) |
| ***C12N 5/04*** | (2006.01) |

(52) U.S. Cl.
CPC .................. *A01H 6/14* (2018.05); *A23L 2/60* (2013.01); *A23L 27/00* (2016.08); *A61K 36/28* (2013.01); *C07K 14/415* (2013.01); *C12N 5/04* (2013.01)

(58) Field of Classification Search
CPC .. A01H 6/14; A23L 27/00; A23L 2/60; A61K 36/28; C07K 14/415; C12N 5/04
See application file for complete search history.

(56) References Cited

U.S. PATENT DOCUMENTS

| | | | | |
|---|---|---|---|---|
| 2007/0116835 | A1 | 5/2007 | Prakash et al. | |
| 2011/0183056 | A1 | 7/2011 | Morita et al. | |
| 2013/0202742 | A1 | 8/2013 | Prakash et al. | |
| 2014/0187761 | A1 | 7/2014 | Morita et al. | |
| 2016/0021918 | A1 | 1/2016 | Brower, III et al. | |
| 2016/0058050 | A1 | 3/2016 | Morita et al. | |
| 2017/0283819 | A1 | 10/2017 | Markosyan et al. | |
| 2018/0077959 | A1 | 3/2018 | Morita et al. | |
| 2019/0330648 | A1* | 10/2019 | Markosyan .............. | C12N 5/04 |
| 2019/0357581 | A1 | 11/2019 | Morita et al. | |
| 2020/0281141 | A1 | 9/2020 | Iwaki et al. | |
| 2021/0037864 | A1 | 2/2021 | Morita et al. | |
| 2021/0068360 | A1 | 3/2021 | Brower, III et al. | |
| 2021/0207159 | A1 | 7/2021 | Markosyan et al. | |
| 2022/0087124 | A1 | 3/2022 | Hirai et al. | |
| 2022/0201955 | A1 | 6/2022 | Hirai et al. | |

FOREIGN PATENT DOCUMENTS

| | | | | |
|---|---|---|---|---|
| CN | 108697137 A | | 10/2018 | |
| CN | 113226017 A | | 8/2021 | |
| CN | 113677196 A | | 11/2021 | |
| EP | 3903575 A1 | | 11/2021 | |
| EP | 3903779 A1 | | 11/2021 | |
| JP | 2016-515814 A | | 6/2016 | |
| WO | 2007/070224 A2 | | 6/2007 | |
| WO | 2010/038911 A1 | | 4/2010 | |
| WO | WO-2016/049531 A1 | * | 3/2016 | |
| WO | WO-2017035524 A1 | * | 3/2017 | ............... A23L 2/60 |
| WO | 2019/074089 A1 | | 4/2019 | |
| WO | WO 2019/0330648 A1 | * | 10/2019 | |

OTHER PUBLICATIONS

Extended European Search Report dated May 2, 2024, issued in European patent application No. 21804612.6.
International Search Report issued in PCT/JP2021/017953, dated Jul. 13, 2021, along with an English translation.

* cited by examiner

*Primary Examiner* — Bratislav Stankovic
*Assistant Examiner* — Emily K Johnson
(74) *Attorney, Agent, or Firm* — Greenblum & Bernstein, P.L.C.

(57) ABSTRACT

A *stevia* plant that contains useful steviol glycoside such as rebaudioside D at higher content as compared with known *stevia* species. Also, a method of producing such a *stevia* plant, and a dried leaf and an extract obtainable from such a plant.

18 Claims, 3 Drawing Sheets

Specification includes a Sequence Listing.

FIG.1

AATTATATGATAGAAATTGTTTTCACATTTTGTGTGCCACACACGTCAACGCC
TCTAAGCCACACGATTAAGGTATGACATTTAGAATAAAATCTTTTATTATTGGA
AGATAGAGACAAAATCTTTTCTTTCCTTATTTATTTTTTATAATAATTACACGCA
TCTTCTATTCTCAACTACTTTAACCTATATGCGCTAGTCCA (SEQ ID NO:22)

FIG.2

GAAACTGAAAGAGAAGTAAGTTAACAGAATGCGTTTYTTCGTAAATAATCTTT
TCTTTTATTTTTATCTTCAAAAAATAAATAACCAAGATTTGTTTGGATTTGTTTC
TATTTATTTAGACAAATCATTATTAATATTTAATMTTTCYCCGTGAATTATATGAT
AGAAATTGTTTTCACATTTTGTGTGCCAYACACGTCAACGCCTCTAAGCCAC
ACGATTAAGGTATGACATTTAGAATAAAATCTTTTATTATTGGAAGATAGAGAC
AAAATCTTTTCTTTCCTTATTTATTTTTTATAATAATTACACGCATCTTCTATTCT
CAACTACTTTAACCTATATGCGCTAGTCCACTACGTAG
(SEQ ID NO:26)

FIG.3

AGAGAAGTAAGWTAACAGAATGCGTTTTTTCGTAAATAATCTTTTCTTTTATT
TTTATCTTCAAAAAATAAATAACCAAGATTTGTTTGGATTTGTTTCTATTTATTT
AGACAAATCATTATTAATATTTAATMTTTCYCCGTGAATTATATGATAGAAATTG
TTTTCACATTTTGTGTGCCAYACACGTCAACGCCTCTAA (SEQ ID NO:30)

FIG.4

CCAAGATTTGTTTGGATTTGTTTCTATTTATTTAGACAAATCATTATTAATATTT
AATCTTTCYCCGTGAATTATATGATAGAAATTGTTTTCACATTTTGTGTGCCAY
ACACGTCAACGCCTCTAAGCCACACGAT (SEQ ID NO:34)

FIG.5

CCAAGATTTGTTTGGATTTGTTTCTATTTATTTAGACAAATCATTATTAATATTT
AATMTTTCTCCGTGAATTATATGATAGAAATTGTTTTCACATTTTGTGTGCCAY
ACACGTCAACGCCTCTAAGCCACACGAT (SEQ ID NO:38)

FIG.6

GGCAGCCATTGATGATGTTGTTGAATGTGATTAATTTGAATGTTATAAAGAAT
TTGGAAAAGAAAAAGGAGGGGACAAAGTTGATGAAATTAGGGGAGTTATGA
TTATGATGGCCATGGTGATTGTGATGAGTGGCACTATGTAATCTAATATTTGA
AGATATGAGACCACTTGACCATGTTATAATCTTATACAAAATAATTAATCCCTC
ACGGTAATTTTTTTCTAATCCTTAAACTGAAATTTGAAAGTAATTTGAGATAGT
GTTTCCCCTAATTTATGCTTTTAGCATGCATTTATTCTATCATATTTTCTATGAG
AATTGG (SEQ ID NO:42)

FIG.7

TGATTTTGAAAGGATCTGACTGTATGTTTATATGACATAGTTATGAGTTTGAA
CCCCAATGGCTAACCCT (SEQ ID NO:46)

FIG.8

AATCAGTCCAATTTAAACGTGCTCTACTTACAGAGTTATCATATTTATTAAGGC
ACTAAAACATGAAACTGACGTGACGAATTGAAAGATTATTCCAATCTTGATCC
ATTTTGCCACTTAAAACAAGATGAAGATAACATAAAAAAGATCGGAAAAAAAT
GATACCATGTAAACGAATACGAAACAACATAAAACAATTAGGTACCCTTGAGT
TTTGATTTCCTGGTAAAAACTAAATAAAAAACACATTAATTCACAACAAACGA
TTATGACCGGTGAAGAAAAAGATTGGAACAGATGATGAAGGAATAACATATT
CTCCTGATGATCGATGATAGATGAGAAATTGGGGTATTAAGGTTTGCAATTC
CAAAGGAATTCGTCAGATAGGAGAAACTGAAAACAGAATATCATGTCTTATTT
AAAAAAAACGGGTATGAGTTTGTGTTTGTGGGTTTTTGGGTTAAATATGAATT
GAGTTACTCTGATGAAGAGAAGTG (SEQ ID NO:133)

REBAUDIOSIDE D-RICH STEVIA PLANT

TECHNICAL FIELD

The present invention relates to a *Stevia* plant with high content of a useful steviol glycoside such as rebaudioside D, a screening method thereof, etc.

BACKGROUND ART

In response to consumers' diversified needs, various drinks have been developed and are commercially available. Saccharides such as sucrose are components very commonly blended in drinks for the purpose of, for example, conferring sweetness. However, their influence on health due to excessive consumption has been pointed out. Thus, there are growing needs for lower calorie and naturally derived sweeteners. For example, Patent Literature 1 discloses a functional sweetener composition containing a vitamin, a high intensity sweetener, and a sweetness improving composition.

Steviol glycoside is known as a sweet component contained in a *Stevia* extract. The *Stevia* extract is mainly extracted and purified from a *Stevia* leaf. *Stevia* is a perennial plant of the family Asteraceae with Paraguay in the South America as its place of origin, and its scientific name is *Stevia rebaudiana* Bertoni. *Stevia* contains a component having approximately 300 or more times the sweetness of sugar and is therefore cultivated for use of this sweet component extracted therefrom as a natural sweetener. The presence of various glycosides such as rebaudioside A (hereinafter, "rebaudioside A" is also abbreviated as "Reb"), RebB, RebC, RebD, RebE and RebD has been reported as steviol glycoside (Patent Literature 2). Among various steviol glycosides, for example, RebA is evaluated as a high intensity sweetener having good quality of sweetness and is widely used. The other steviol glycosides have also been increasingly found to have their unique sweetness and associated taste.

Under these circumstances, a *Stevia* plant containing 3.57% of RebD per dried leaf is known (Patent Literature 3).

CITATION LIST

Patent Literature

Patent Literature 1: WO2007/070224
Patent Literature 2: WO2010/038911
Patent Literature 3: WO2019/074089

SUMMARY OF INVENTION

Technical Problem

RebD reportedly has good quality of taste, among steviol glycosides, but cannot be obtained in large amounts from natural *Stevia* plants. Thus, the obtainment thereof is of concern.

Means for Solving the Problems

The present invention provides a *Stevia* plant containing a useful steviol glycoside such as RebD at high content as compared with the wild type *Stevia* species, a method of producing the plant, and a method of screening for the plant.

In one aspect, the present invention provides the following.

[1-1] A *Stevia* plant having at least one of the following chemical features (1) to (7).
 (1) The content of rebaudioside (Reb) D is 3.6% or more per unit mass of a dried leaf.
 (2) The total content of RebD and RebM is 4.9% or more per unit mass of a dried leaf.
 (3) The mass ratio of RebD to total steviol glycoside is 32.0% or more.
 (4) The total mass ratio of RebD and RebM to total steviol glycoside is 38.2% or more.
 (5) The content of RebN is 1.0% or more per unit mass of a dried leaf.
 (6) The total content of RebD and RebN is 4.0% or more per unit mass of a dried leaf.
 (7) The total content of RebD, RebM, and RebN is 4.4% or more per unit mass of a dried leaf.

[1-2] The plant according to [1-1] having at least one of the following genetic features (A) to (G).
 (A) Heterozygous for the allele wherein the base at the position corresponding to position 40 of SEQ ID NO: 1 is C.
 (B) Heterozygous for the allele wherein the base at the position corresponding to position 21 of SEQ ID NO: 2 is T.
 (C) Heterozygous for the allele wherein the base at the position corresponding to position 28 of SEQ ID NO: 3 is T.
 (D) Heterozygous for the allele wherein the base at the position corresponding to position 59 of SEQ ID NO: 4 is C.
 (E) Heterozygous for the allele wherein the base at the position corresponding to position 64 of SEQ ID NO: 5 is T.
 (F) Heterozygous for the allele wherein the base at the position corresponding to position 290 of SEQ ID NO: 6 is C.
 (G) Heterozygous for the allele wherein the base at the position corresponding to position 33 of SEQ ID NO: 7 is T.

[1-3] A *Stevia* plant having at least one of the following genetic features (A) to (G).
 (A) Heterozygous for the allele wherein the base at the position corresponding to position 40 of SEQ ID NO: 1 is C.
 (B) Heterozygous for the allele wherein the base at the position corresponding to position 21 of SEQ ID NO: 2 is T.
 (C) Heterozygous for the allele wherein the base at the position corresponding to position 28 of SEQ ID NO: 3 is T.
 (D) Heterozygous for the allele wherein the base at the position corresponding to position 59 of SEQ ID NO: 4 is C.
 (E) Heterozygous for the allele wherein the base at the position corresponding to position 64 of SEQ ID NO: 5 is T.
 (F) Heterozygous for the allele wherein the base at the position corresponding to position 290 of SEQ ID NO: 6 is C.
 (G) Heterozygous for the allele wherein the base at the position corresponding to position 33 of SEQ ID NO: 7 is T.

[1-4] The plant according to any one of [1-1] to [1-3], wherein the plant is a non-genetically modified plant.

[1-5] The plant according to any one of [1-1] to [1-4], wherein the plant includes a *Stevia* plant subjected to a mutagenesis treatment and a progeny plant thereof.

[1-6] A seed, a tissue, a dried leaf, a tissue culture or a cell of the plant according to any one of [1-1] to [1-5].

[1-7] The tissue, tissue culture or cell according to [1-6], which is selected from an embryo, a meristem cell, a pollen, a leaf, a root, a root apex, a petal, a protoplast, a leaf section and a callus.

[1-8] A method of producing a *Stevia* plant having at least one of the following chemical features (1) to (7), the method comprising a step of crossing the plant according to any one of [1-1] to [1-5] with a second *Stevia* plant.

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

[1-9] The method according to [1-8], wherein the second plant is the plant according to any one of [1-1] to [1-5].

[1-10] An extract of the plant according to any one of [1-1] to [1-5], or of the seed, tissue, dried leaf, tissue culture or cell according to [1-6] or [1-7], wherein the extract comprises at least one of RebD, RebM and RebN.

[1-11] A method of producing an extract comprising at least one of RebD, RebM and RebN, comprising a step of obtaining an extract from the plant according to any one of [1-1] to [1-5], or from the seed, tissue, dried leaf, tissue culture or cell according to [1-6] or [1-7].

[1-12] A method of producing RebD, RebM and/or RebN, comprising a step of purifying at least one of RebD, RebM and RebN from the extract according to [1-10].

[1-13] A method of producing a food or beverage, a sweetener composition, a flavor or a medicament, comprising:

a step of providing an extract of the plant according to any one of [1-1] to [1-5], an extract of the seed, tissue, dried leaf, tissue culture or cell according to [1-6] or [1-7], or the extract according to [1-10]; and a step of adding the extract to a raw material for the food or beverage, sweetener composition, flavor or medicament.

[1-14] A method of screening for the *Stevia* plant according to any one of [1-1] to [1-5], comprising a step of detecting from the genome of a test *Stevia* plant the presence and/or the absence of at least one of the following genetic features (A) to (G).

(A) Heterozygous for the allele wherein the base at the position corresponding to position 40 of SEQ ID NO: 1 is C.

(B) Heterozygous for the allele wherein the base at the position corresponding to position 21 of SEQ ID NO: 2 is T.

(C) Heterozygous for the allele wherein the base at the position corresponding to position 28 of SEQ ID NO: 3 is T.

(D) Heterozygous for the allele wherein the base at the position corresponding to position 59 of SEQ ID NO: 4 is C.

(E) Heterozygous for the allele wherein the base at the position corresponding to position 64 of SEQ ID NO: 5 is T.

(F) Heterozygous for the allele wherein the base at the position corresponding to position 290 of SEQ ID NO: 6 is C.

(G) Heterozygous for the allele wherein the base at the position corresponding to position 33 of SEQ ID NO: 7 is T.

[1-15] The method according to [1-14], wherein the step of detecting a genetic feature is performed by use of CAPS method, dCAPS method or TaqMan PCR method.

[1-16] The method according to [1-14] or [1-15], further comprising a step of measuring the content of RebD, RebM and/or RebN in a test *Stevia* plant tissue.

[1-17] A screening kit for the *Stevia* plant according to any one of [1-1] to [1-5], comprising a reagent for detecting the presence and/or the absence of at least one of the following genetic features (A) to (G).

(A) Heterozygous for the allele wherein the base at the position corresponding to position 40 of SEQ ID NO: 1 is C.

(B) Heterozygous for the allele wherein the base at the position corresponding to position 21 of SEQ ID NO: 2 is T.

(C) Heterozygous for the allele wherein the base at the position corresponding to position 28 of SEQ ID NO: 3 is T.

(D) Heterozygous for the allele wherein the base at the position corresponding to position 59 of SEQ ID NO: 4 is C.

(E) Heterozygous for the allele wherein the base at the position corresponding to position 64 of SEQ ID NO: 5 is T.

(F) Heterozygous for the allele wherein the base at the position corresponding to position 290 of SEQ ID NO: 6 is C.

(G) Heterozygous for the allele wherein the base at the position corresponding to position 33 of SEQ ID NO: 7 is T.

[1-18] The kit according to [1-17], wherein the reagent comprises a primer and/or a probe for use in CAPS method, dCAPS method or TaqMan PCR method.

[1-19] A method of producing the *Stevia* plant according to any one of [1-1] to [1-5], comprising a step of introducing at least one of the following variations (A) to (G).

(A) the variation from T to C at a position corresponding to position 40 of SEQ ID NO: 1.

(B) the variation from A to T at a position corresponding to position 21 of SEQ ID NO: 2.

(C) the variation from C to T at a position corresponding to position 28 of SEQ ID NO: 3.

(D) the variation from A to C at a position corresponding to position 59 of SEQ ID NO: 4.

(E) the variation from C to T at a position corresponding to position 64 of SEQ ID NO: 5.

(F) the variation from T to C at a position corresponding to position 290 of SEQ ID NO: 6.

(G) the variation from A to T at a position corresponding to position 33 of SEQ ID NO: 7.

[1-20] The method according to [1-19], wherein the introduction of the variation is performed by a mutagenesis treatment.

[2-1] A *Stevia* plant having the following genetic feature (H).

(H) Heterozygous for the allele wherein the base at the position corresponding to position 40 of SEQ ID NO: 130 is C.

[2-2] The plant according to [2-1] having at least one of the following chemical features (1) to (7).

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

[2-3] The plant according to [2-1] or [2-2], wherein the plant is a non-genetically modified plant.

[2-4] The plant according to any one of [2-1] to [2-3], wherein the plant includes a *Stevia* plant subjected to a mutagenesis treatment and a progeny plant thereof.

[2-5] A seed, a tissue, a dried leaf, a tissue culture or a cell of the plant according to any one of [2-1] to [2-4].

[2-6] The tissue, tissue culture or cell according to [2-5], which is selected from an embryo, a meristem cell, a pollen, a leaf, a root, a root apex, a petal, a protoplast, a leaf section and a callus.

[2-7] A method of producing a *Stevia* plant having at least one of the following chemical features (1) to (7), the method comprising a step of crossing the plant according to any one of [2-1] to [2-4] with a second *Stevia* plant.

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

[2-8] The method according to [2-7], wherein the second plant is the plant according to any one of [2-1] to [2-4].

[2-9] An extract of the plant according to any one of [2-1] to [2-4], or of the seed, tissue, dried leaf, tissue culture or cell according to [2-5] or [2-6], wherein the extract comprises at least one of RebD, RebM and RebN.

[2-10] A method of producing an extract comprising at least one of RebD, RebM and RebN, comprising a step of obtaining an extract from the plant according to any one of [2-1] to [2-4], or from finish indent the seed, tissue, dried leaf, tissue culture or cell according to [2-5] or [2-6].

[2-11] A method of producing RebD, RebM and/or RebN, comprising a step of purifying at least one of RebD, RebM and RebN from the extract according to [2-9].

[2-12] A method of producing a food or beverage, a sweetener composition, a flavor or a medicament, comprising:

a step of providing an extract of the plant according to any one of [2-1] to [2-4], an extract of the seed, tissue, dried leaf, tissue culture or cell according to [2-5] or [2-6], or the extract according to [2-9]; and a step of adding the extract to a raw material for the food or beverage, sweetener composition, flavor or medicament.

[2-13] A method of screening for a *Stevia* plant having at least one of the following chemical features (1) to (7), comprising a step of detecting from the genome of a test *Stevia* plant the presence and/or the absence of the genetic feature (H) of being heterozygous for the allele wherein the base at the position corresponding to position 40 of SEQ ID NO: 130 is C.

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

[2-14] The method according to [2-13], wherein the step of detecting a genetic feature is performed by use of CAPS method, dCAPS method or TaqMan PCR method.

[2-15] The method according to [2-13] or [2-14], further comprising a step of measuring the content of RebD, RebM and/or RebN in a test *Stevia* plant tissue.

[2-16] A screening kit for a *Stevia* plant having at least one of the following chemical features (1) to (7), comprising a reagent for detecting the presence and/or the absence of the genetic feature (H) of being heterozygous for the allele wherein the base at the position corresponding to position 40 of SEQ ID NO: 130 is C.

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

[2-17] The kit according to [2-16], wherein the reagent comprises a primer and/or a probe for use in CAPS method, dCAPS method or TaqMan PCR method.

[2-18] A method of producing a *Stevia* plant having at least one of the following chemical features (1) to (7), comprising a step of introducing the variation from G to C at a position corresponding to position 40 of SEQ ID NO: 130.

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

[2-19] The method according to [2-18], wherein the introduction of the variation is performed by a mutagenesis treatment.

Advantageous Effects of Invention

The present invention enables the obtainment of a *Stevia* plant richer in a useful steviol glycoside and the provision of an approach for producing such a plant, a leaf obtainable from such a plant, and a food, a drink, etc. containing the useful steviol glycoside obtained from this leaf.

BRIEF DESCRIPTION OF DRAWINGS

FIG. 1 is a diagram showing the position of the variation (A) in the nucleotide sequence of SEQ ID NO: 22. The boxed base is a base related to the variation (A).

FIG. 2 is a diagram showing the position of the variation (B) in the nucleotide sequence of SEQ ID NO: 26. The boxed base is a base related to the variation (B).

FIG. 3 is a diagram showing the position of the variation (C) in the nucleotide sequence of SEQ ID NO: 30. The boxed base is a base related to the variation (C).

FIG. 4 is a diagram showing the position of the variation (D) in the nucleotide sequence of SEQ ID NO: 34. The boxed base is a base related to the variation (D).

FIG. 5 is a diagram showing the position of the variation (E) in the nucleotide sequence of SEQ ID NO: 38. The boxed base is a base related to the variation (E).

FIG. 6 is a diagram showing the position of the variation (F) in the nucleotide sequence of SEQ ID NO: 42. The boxed base is a base related to the variation (F).

FIG. 7 is a diagram showing the position of the variation (G) in the nucleotide sequence of SEQ ID NO: 46. The boxed base is a base related to the variation (G).

FIG. 8 is a diagram showing the position of the variation (H) in the nucleotide sequence of SEQ ID NO: 133. The boxed base is a base related to the variation (H).

DESCRIPTION OF EMBODIMENTS

Figure 9:
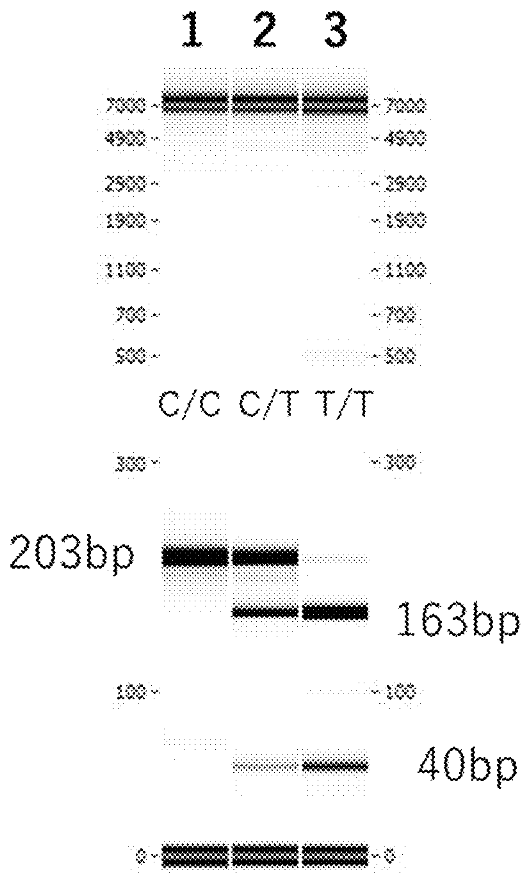
FIG. 9 is a diagram showing results of the analysis on whether a *Stevia* plant has a genetic feature (A) by dCAPS method. Lane 1 shows electrophoretic images of samples of DNA of individuals homozygous for alleles with variation (A) treated with restriction-enzyme RsaI, lane 2 shows electrophoretic images of samples of DNA of individuals heterozygous for alleles with variation (A) treated with restriction-enzyme RsaI, and lane 3 shows DNA of individuals homozygous for alleles without variation (A) treated with restriction-enzyme RsaI.
Figure 10:
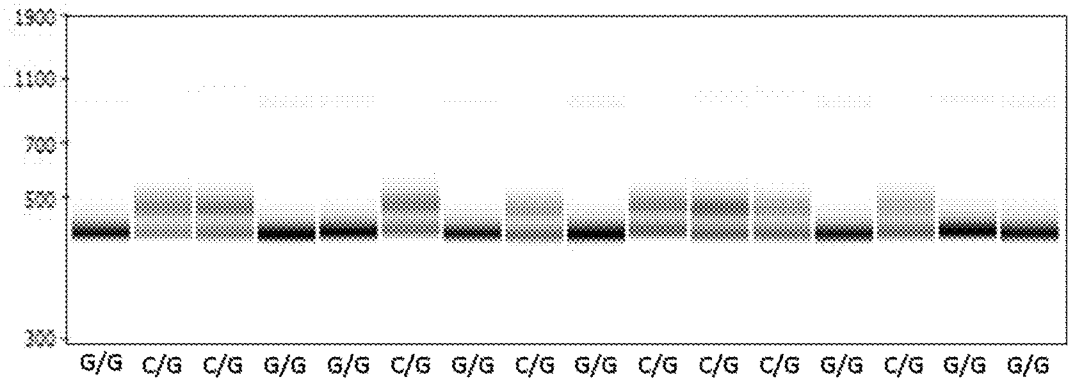
FIG. 10 is a diagram showing results of the analysis on whether a *Stevia* plant has a genetic feature (H) by dCAPS method. Electrophoretic images of samples of DNA of each individual which were amplified by a forward primer of SEQ ID NO: 137 and a reverse primer of SEQ ID NO: 138, followed by a treatment with restriction enzyme EcoRV. Lanes with a single band are the ones for individuals homozygous for alleles without variation (H) (G/G), and lanes with a double band are the ones for individuals heterozygous for alleles with variation (H) (C/G).

Hereinafter, the present invention will be described in detail. The embodiments are given below merely for illustrating the present invention and are not intended to limit the present invention by such embodiments. The present invention can be carried out in various modes without departing from the spirit of the present invention.

Note that all documents, as well as laid-open application publications, patent application publications, and other patent documents cited herein shall be incorporated herein by reference. The present specification incorporates the contents of the specification and the drawings of Japanese Patent Application No. 2020-084126, filed on May 12, 2020, from which the present application claims priority.

1. *Stevia* Plant

In one embodiment, the present invention provides a *Stevia* plant having at least one of the following chemical features (1) to (7) (hereinafter, generically referred to as the "plant A of the present invention" or "*Stevia* plant A of the present invention").

(1) The content of rebaudioside (Reb) D is 3.6% or more per unit mass of a dried leaf.

(2) The total content of RebD and RebM is 4.9% or more per unit mass of a dried leaf.

(3) The mass ratio of RebD to total steviol glycoside is 32.0% or more.

(4) The total mass ratio of RebD and RebM to total steviol glycoside is 38.2% or more.

(5) The content of RebN is 1.0% or more per unit mass of a dried leaf.

(6) The total content of RebD and RebN is 4.0% or more per unit mass of a dried leaf.

(7) The total content of RebD, RebM, and RebN is 4.4% or more per unit mass of a dried leaf.

The total steviol glycoside (TSG) is a generic name for measurable steviol glycosides and includes neither an unknown steviol glycoside nor a steviol glycoside present at a level less than the detection limit. Preferably, the TSG is any combination of two or more members selected from the group consisting of RebA, RebB, RebC, RebD, RebE, RebF, RebG, RebI, RebJ, RebK, RebM, RebN, RebO, RebQ, RebR, dulcoside A, rubusoside, steviolmonoside, steviolbioside and stevioside. In a specific embodiment, the TSG consists of RebA, RebB, RebC, RebD, RebE, RebF, RebG, RebM, RebN and stevioside.

In the plant A of the present invention having the chemical feature (1), the feature "the content of RebD is 3.6% or more per unit mass of a dried leaf" means that, for example, RebD is contained at a ratio of 3.6% by mass or more (e.g., 1.8 mg or more) in a dried leaf having a predetermined mass (e.g., 50 mg). In this embodiment, the ratio of RebD per unit mass of a dried leaf is not limited and may be, for example, 3.6% or more, 3.7% or more, 3.8% or more, 3.9% or more, 4.0% or more, 4.1% or more, 4.2% or more, 4.3% or more, 4.4% or more, 4.5% or more, 4.6% or more, 4.7% or more, 4.8% or more, 4.9% or more, 5.0% or more, 5.1% or more, 5.2% or more, 5.3% or more, 5.4% or more, 5.5% or more, 5.6% or more, 5.7% or more, 5.8% or more, 5.9% or more, 6.0% or more, 6.1% or more, 6.2% or more, 6.3% or more, or the like, and is preferably 4.0% or more. The upper limit of the ratio of RebD per unit mass of a dried leaf is not particularly limited and may be, for example, 20%, 15% or 10%.

In this context, the dried leaf refers to a leaf having a water content decreased to 3 to 4% by weight by drying a fresh leaf of the *Stevia* plant of the present invention.

In the plant A of the present invention having the chemical feature (2), the feature "the total content of RebD and RebM is 4.9% or more per unit mass of a dried leaf" means that, for example, the total mass of RebD and RebM contained in a dried leaf having a predetermined mass (e.g., 50 mg) is 4.9% by mass or more (e.g., 2.45 mg or more). In this embodiment, the total ratio of RebD and RebM per unit mass of a dried leaf is not limited and may be, for example, 4.9% or more, 5.0% or more, 5.1% or more, 5.2% or more, 5.3% or more, 5.4% or more, 5.5% or more, 5.6% or more, 5.7% or more, 5.8% or more, 5.9% or more, 6.0% or more, 6.1% or more, 6.2% or more, 6.3% or more, 6.4% or more, 6.5% or more, 6.6% or more, 6.7% or more, 6.8% or more, 6.9% or more, 7.0% or more, 7.1% or more, 7.2% or more, 7.3% or more, 7.4% or more, 7.5% or more, 7.6% or more, 7.7% or more, 7.8% or more, 7.9% or more, or the like, and is preferably 5.4% or more. The upper limit of the total ratio of RebD and RebM per unit mass of a dried leaf is not particularly limited and may be, for example, 25%, 20% or 15%.

In the plant A of the present invention having the chemical feature (3), the feature "the mass ratio of RebD to TSG is 32.0% or more" means that, for example, when the mass of RebD contained in a leaf (e.g., a dried leaf or a fresh leaf) is indicated by RebD/TSG % as the ratio to the total mass of steviol glycosides obtained from the leaf, the value of RebD/TSG is 32.0% or more. In this embodiment, the value of RebD/TSG is not limited and may be, for example, 32.0% or more, 32.2% or more, 32.4% or more, 32.6% or more, 32.8% or more, 33.0% or more, 33.2% or more, 33.4% or more, 33.6% or more, 33.8% or more, 34.0% or more, 34.2% or more, 34.4% or more, 34.6% or more, 34.8% or more, 35.0% or more, 35.2% or more, 35.4% or more, 35.6% or more, 35.8% or more, 36.0% or more, 36.2% or more, 36.4% or more, 36.6% or more, 36.8% or more, 37.0% or more, 37.2% or more, 37.4% or more, 37.6% or more, 37.8% or more, 38.0% or more, 38.2% or more, 38.4% or more, 38.6% or more, 38.8% or more, 39.0% or more, 39.2% or more, 39.4% or more, 39.6% or more, 39.8% or more, 40.0% or more, or the like, and is preferably 34.0% or more. The upper limit of the mass ratio of RebD to TSG is not particularly limited and may be, for example, 85%, 75%, 65% or 55%.

In the plant A of the present invention having the chemical feature (4), the feature "the total mass ratio of RebD and RebM to TSG is 38.2% or more" means that, for example, when the total mass of RebD and RebM contained in a leaf (e.g., a dried leaf or a fresh leaf) is indicated by (RebD+RebM)/TSG % as the ratio to the total mass of steviol glycosides obtained from the leaf, the value of (RebD+RebM)/TSG is 38.2% or more. In this embodiment, the value of (RebD+RebM)/TSG is not limited and may be, for example, 38.2% or more, 38.5% or more, 38.7% or more, 39.0% or more, 39.2% or more, 39.5% or more, 39.7% or more, 40.0% or more, 40.2% or more, 40.5% or more, 40.7% or more, 41.0% or more, 41.2% or more, 41.5% or more, 41.7% or more, 42.0% or more, 42.2% or more, 42.5% or more, 42.7% or more, 43.0% or more, 43.2% or more, 43.5% or more, 43.7% or more, 44.0% or more, 44.2% or more, 44.5% or more, 44.7% or more, 45.0% or more, 45.2% or more, 45.5% or more, 45.7% or more, 46.0% or more, 46.2% or more, 46.5% or more, 46.7% or more, 47.0% or more, 47.2% or more, 47.5% or more, 47.7% or more, 48.0% or more, 48.2% or more, 48.5% or more, 48.7% or more, 49.0% or more, 49.2% or more, 49.5% or more, or the like, and is preferably 39.2% or more. The upper limit of the mass ratio of RebD+RebM to TSG is not particularly limited and may be, for example, 85%, 75%, 65% or 55%.

In the plant A of the present invention having the chemical feature (5), the feature "the content of RebN is 1.0% or more per unit mass of a dried leaf" means that, for example, RebN is contained at a ratio of 1.0% by mass or more (e.g., 0.5 mg or more) in a dried leaf having a predetermined mass (e.g., 50 mg). In this embodiment, the ratio of RebN per unit mass of a dried leaf is not limited and may be, for example, 1.00% or more, 1.01% or more, 1.02% or more, 1.03% or more, 1.04% or more, 1.05% or more, 1.06% or more, 1.07% or more, 1.08% or more, 1.09% or more, 1.10% or more, 1.11% or more, 1.12% or more, 1.13% or more, 1.14% or more, 1.15% or more, 1.16% or more, 1.17% or more, 1.18% or more, 1.19% or more, 1.20% or more, 1.21% or more, 1.22% or more, 1.23% or more, 1.24% or more, 1.25% or more, or the like, and is preferably 1.10% or more. The upper limit of the ratio of RebN per unit mass of a dried leaf is not particularly limited and may be, for example, 15%, 10%, or 5%.

In the plant A of the present invention having the chemical feature (6), the feature "the total content of RebD and RebN is 4.0% or more per unit mass of a dried leaf" means that, for example, the total mass of RebD and RebN contained in a dried leaf having a predetermined mass (e.g., 50 mg) is 4.0% by mass or more (e.g., 2 mg or more). In this embodiment, the total ratio of RebD and RebN per unit mass of a dried leaf is not limited and may be, for example, 4.0% or more, 4.1% or more, 4.2% or more, 4.3% or more, 4.4% or more, 4.5% or more, 4.6% or more, 4.7% or more, 4.8% or more, 4.9% or more, 5.0% or more, 5.1% or more, 5.2% or more, 5.3% or more, 5.4% or more, 5.5% or more, 5.6% or more, 5.7% or more, 5.8% or more, 5.9% or more, 6.0% or more, 6.1% or more, 6.2% or more, 6.3% or more, 6.4% or more, 6.5% or more, 6.6% or more, 6.7% or more, 6.8% or more, 6.9% or more, 7.0% or more, 7.1% or more, 7.2% or more, 7.3% or more, 7.4% or more, 7.5% or more, or the like, and is preferably 5.2% or more. The upper limit of the total ratio of RebD and RebN per unit mass of a dried leaf is not particularly limited and may be, for example, 25%, 20% or 15%.

In the plant A of the present invention having the chemical feature (7), the feature "the total content of RebD, RebM and RebN is 4.4% or more per unit mass of a dried leaf" means that, for example, the total mass of RebD, RebM and RebN contained in a dried leaf having a predetermined mass (e.g., 50 mg) is 4.4% by mass or more (e.g., 2.2 mg or more). In this embodiment, the total ratio of RebD, RebM and RebN per unit mass of a dried leaf is not limited and may be, for example, 4.4% or more, 4.5% or more, 4.6% or more, 4.7% or more, 4.8% or more, 4.9% or more, 5.0% or more, 5.1% or more, 5.2% or more, 5.3% or more, 5.4% or more, 5.5% or more, 5.6% or more, 5.7% or more, 5.8% or more, 5.9% or more, 6.0% or more, 6.1% or more, 6.2% or more, 6.3% or more, 6.4% or more, 6.5% or more, 6.6% or more, 6.7% or more, 6.8% or more, 6.9% or more, 7.0% or more, 7.1% or more, 7.2% or more, 7.3% or more, 7.4% or more, 7.5% or more, 7.6% or more, 7.7% or more, 7.8% or more, 7.9% or more, 8.0% or more, 8.1% or more, 8.2% or more, 8.3% or more, 8.4% or more, 8.5% or more, 8.6% or more, 8.7% or more, 8.8% or more, 8.9% or more, 9.0% or more, or the like, and is preferably 6.3% or more. The upper limit of the total ratio of RebD, RebM and RebN per unit mass of a dried leaf is not particularly limited and may be, for example, 25%, 20% or 15%.

In some embodiments, the plant A of the present invention may have a plurality of the above chemical features. In these embodiments, the number of chemical features may be any of 2 to 7, i.e., 2, 3, 4, 5, 6 or 7. The combination of the chemical features is not particularly limited and includes, for example, each of the following combinations within the parentheses: (1, 2), (1, 3), (1, 4), (1, 5), (1, 6), (1, 7), (2, 3), (2, 4), (2, 5), (2, 6), (2, 7), (3, 4), (3, 5), (3, 6), (3, 7), (4, 5), (4, 6), (4, 7), (5, 6), (5, 7), (6, 7), (1, 2, 3), (1, 2, 4), (1, 2, 5), (1, 2, 6), (1, 2, 7), (1, 3, 4), (1, 3, 5), (1, 3, 6), (1, 3, 7), (1, 4, 5), (1, 4, 6), (1, 4, 7), (1, 5, 6), (1, 5, 7), (1, 6, 7), (2, 3, 4), (2, 3, 5), (2, 3, 6), (2, 3, 7), (2, 4, 5), (2, 4, 6), (2, 4, 7), (2, 5, 6), (2, 5, 7), (2, 6, 7), (3, 4, 5), (3, 4, 6), (3, 4, 7), (3, 5, 6), (3, 5, 7), (3, 6, 7), (4, 5, 6), (4, 5, 7), (4, 6, 7), (5, 6, 7), (1, 2, 3, 4), (1, 2, 3, 5), (1, 2, 3, 6), (1, 2, 3, 7), (1, 2, 4, 5), (1, 2, 4, 6), (1, 2, 4, 7), (1, 2, 5, 6), (1, 2, 5, 7), (1, 2, 6, 7), (1, 3, 4, 5), (1, 3, 4, 6), (1, 3, 4, 7), (1, 3, 5, 6), (1, 3, 5, 7), (3, 6, 7), (4, 5, 6), (4, 5, 7), (4, 6, 7), (5, 6, 7), (2, 3, 4, 5), (2, 3, 4, 6), (2, 3, 4, 7), (2, 3, 5, 6), (2, 3, 5, 7), (2, 3, 6, 7), (2, 4, 5, 6), (2, 4, 5, 7), (2, 4, 6, 7), (2, 5, 6, 7), (3, 4, 5, 6), (3, 4, 5, 7), (3, 4, 6, 7), (3, 5, 6, 7), (4, 5, 6, 7), (1, 2, 3, 4, 5), (1, 2, 3, 4, 6), (1, 2, 3, 4, 7), (1, 2, 3, 5, 6), (1, 2, 3, 5, 7), (1, 2, 3, 6, 7), (1, 2, 4, 5, 6), (1, 2, 4, 5, 7), (1, 2, 4, 6, 7), (1, 2, 5, 6, 7), (1, 3, 4, 5, 6), (1, 3, 4, 5, 7), (1, 3, 4, 6, 7), (1, 3, 5, 6, 7), (1, 4, 5, 6, 7), (2, 3, 4, 5, 6), (2, 3, 4, 5, 7), (2, 3, 4, 6, 7), (2, 3, 5, 6, 7), (2, 4, 5, 6, 7), (3, 4, 5, 6, 7), (1, 2, 3, 4, 5, 6), (1, 2, 3, 4, 5, 7), (1, 2, 3, 4, 6, 7), (1, 2, 3, 5, 6, 7), (1, 2, 4, 5, 6, 7), (1, 3, 4, 5, 6, 7), (2, 3, 4, 5, 6, 7) and (1, 2, 3, 4, 5, 6, 7). In the above, for example, (1, 2) means the combination of the chemical feature (1) and the chemical feature (2).

In one embodiment, the present invention provides a *Stevia* plant having at least one of the following genetic features (A) to (G) (hereinafter, generically referred to as the "plant B of the present invention" or "*Stevia* plant B of the present invention").

(A) Heterozygous for the allele wherein the base at the position corresponding to position 40 of SEQ ID NO: 1 is C (see FIG. 1).

(B) Heterozygous for the allele wherein the base at the position corresponding to position 21 of SEQ ID NO: 2 is T (see FIG. 2).

(C) Heterozygous for the allele wherein the base at the position corresponding to position 28 of SEQ ID NO: 3 is T (see FIG. 3).

(D) Heterozygous for the allele wherein the base at the position corresponding to position 59 of SEQ ID NO: 4 is C (see FIG. 4).

(E) Heterozygous for the allele wherein the base at the position corresponding to position 64 of SEQ ID NO: 5 is T (see FIG. 5).

(F) Heterozygous for the allele wherein the base at the position corresponding to position 290 of SEQ ID NO: 6 is C (see FIG. 6).

(G) Heterozygous for the allele wherein the base at the position corresponding to position 33 of SEQ ID NO: 7 is T (see FIG. 7).

In one embodiment, the present invention provides a *Stevia* plant having the following genetic feature (H) (hereinafter, generically referred to as the "plant D of the present invention" or "*Stevia* plant D of the present invention").

(H) Heterozygous for the allele wherein the base at the position corresponding to position 40 of SEQ ID NO: 130 is C (see FIG. 8).

The phrase "position corresponding to" means the following. In case a sequence identical to a reference sequence (e.g., SEQ ID NOs: 1 to 7, etc.) is present in the genome, it means a position in the sequence (e.g., 40, 21, 28, 59, 64, 290, 33, etc.) present in the genome, and in case a sequence identical to the reference sequence is not present in the genome, it means a position in a sequence in the genome corresponding to the reference sequence, which corresponds to the position in the reference sequence. Whether or not a sequence identical to or corresponding to the reference sequence exists in the genome can be determined by, for example, amplifying genomic DNA of the *Stevia* plant of interest with a primer capable of amplifying the reference sequence by PCR, sequencing the amplified product, and performing alignment analysis between the obtained sequence and the reference sequence. Non-limiting examples of a sequence corresponding to a reference sequence include, for example, a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the reference sequence. The position corresponding to the position in the reference sequence in the sequence corresponding to the reference sequence in the genome can be determined by taking into account the nucleotide sequence before and after the position in the reference sequence and the like. For example, a position in the sequence corresponding to the reference sequence in the genome corresponding to a position in the reference sequence can be determined by an alignment analysis of a reference sequence with a sequence corresponding to a reference sequence in the genome.

For instance, when taking "the position corresponding to position 40 of SEQ ID NO: 1" of the genetic feature (A) of the present invention as an example, in case the genome of a *Stevia* plant has a portion consisting of a nucleotide sequence identical to SEQ ID NO: 1, "the position corresponding to position 40 of SEQ ID NO: 1" is position 40 from the 5' end of the portion consisting of a nucleotide sequence identical to SEQ ID NO: 1 in the genome. On the other hand, in case the genome of a *Stevia* plant has a portion consisting of a nucleotide sequence which is not identical to, but which corresponds to SEQ ID NO: 1, the genome does not have a portion consisting of a nucleotide sequence identical to SEQ ID NO: 1. Therefore, "the position corresponding to position 40 of SEQ ID NO: 1" does not necessarily correspond to position 40 from the 5' end of the portion corresponding to SEQ ID NO: 1. However, it is possible to identify "the position corresponding to position 40 of SEQ ID NO: 1" in the genome of such a *Stevia* plant by taking into account the nucleotide sequence before and after the position 40 of SEQ ID NO: 1, and the like. For instance, one can identify "the position corresponding to position 40 of SEQ ID NO: 1" in the genome of a *Stevia* plant by an alignment analysis of the nucleotide sequence of a portion corresponding to SEQ ID NO: 1 in the genome of a *Stevia* plant and the nucleotide sequence of SEQ ID NO: 1.

Here, a position selected from the group consisting of (A) a position corresponding to position 40 of SEQ ID NO: 1, (B) a position corresponding to position 21 of SEQ ID NO: 2, (C) a position corresponding to position 28 of SEQ ID NO: 3, (D) a position corresponding to position 59 of SEQ ID NO: 4, (E) a position corresponding to position 64 of SEQ ID NO: 5, (F) a position corresponding to position 290 of SEQ ID NO: 6, and (G) a position corresponding to position 33 of SEQ ID NO: 7 may be generically referred to as a "polymorphic site of the present invention" or a "variation site of the present invention". Also, each of the above positions (A) to (G) may be referred to as a "polymorphic site (A)", a "polymorphic site (B)", a "variation site (A)", a "variation site (B)", or the like. Further, (H) a position corresponding to position 40 of SEQ ID NO: 130 may be referred to as a "polymorphic site (H)" or a "variation site (H)".

"The portion consisting of a nucleotide sequence corresponding to SEQ ID NO: 1" means, for instance, a portion consisting of a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the nucleotide sequence of SEQ ID NO: 1.

In one embodiment, "the portion consisting of a nucleotide sequence corresponding to SEQ ID NO: 1" includes a portion of the genome of a *Stevia* plant which can be amplified by PCR using a forward primer which hybridizes to a complementary sequence of a portion of positions 1 to 39 from the 5' end of SEQ ID NO: 1 (i.e., from the 5' end of SEQ ID NO: 1 to the base upstream by one base relative to the variation site (A)) and a reverse primer which hybridizes to a portion of positions 1 to 163 from the 3' end of SEQ ID NO: 1 (i.e., from the 3' end of SEQ ID NO: 1 to the base downstream by one base relative to the variation site (A)).

For simplicity, the genetic feature (A) of the present invention is used here as an example for explanation, but the same applies to the genetic features (B) to (H) of the present invention.

In a specific embodiment, "the portion consisting of a nucleotide sequence corresponding to SEQ ID NO: 1" includes, for instance, a portion of the genome of a *Stevia* plant which can be amplified by PCR using a forward primer comprising the nucleotide sequence of SEQ ID NO: 8 and a reverse primer comprising the nucleotide sequence of SEQ ID NO: 9.

In a specific embodiment, "the portion consisting of a nucleotide sequence corresponding to SEQ ID NO: 2" includes, for instance, a portion of the genome of a *Stevia* plant which can be amplified by PCR using a forward primer comprising the nucleotide sequence of SEQ ID NO: 10 and a reverse primer comprising the nucleotide sequence of SEQ ID NO: 11.

In a specific embodiment, "the portion consisting of a nucleotide sequence corresponding to SEQ ID NO: 3" includes, for instance, a portion of the genome of a *Stevia* plant which can be amplified by PCR using a forward primer comprising the nucleotide sequence of SEQ ID NO: 12 and a reverse primer comprising the nucleotide sequence of SEQ ID NO: 13.

In a specific embodiment, "the portion consisting of a nucleotide sequence corresponding to SEQ ID NO: 4" includes, for instance, a portion of the genome of a *Stevia* plant which can be amplified by PCR using a forward primer comprising the nucleotide sequence of SEQ ID NO: 14 and a reverse primer comprising the nucleotide sequence of SEQ ID NO: 15.

In a specific embodiment, "the portion consisting of a nucleotide sequence corresponding to SEQ ID NO: 5" includes, for instance, a portion of the genome of a *Stevia* plant which can be amplified by PCR using a forward primer comprising the nucleotide sequence of SEQ ID NO: 16 and a reverse primer comprising the nucleotide sequence of SEQ ID NO: 17.

In a specific embodiment, "the portion consisting of a nucleotide sequence corresponding to SEQ ID NO: 6" includes, for instance, a portion of the genome of a *Stevia* plant which can be amplified by PCR using a forward primer comprising the nucleotide sequence of SEQ ID NO: 18 and a reverse primer comprising the nucleotide sequence of SEQ ID NO: 19.

In a specific embodiment, "the portion consisting of a nucleotide sequence corresponding to SEQ ID NO: 7" includes, for instance, a portion of the genome of a *Stevia* plant which can be amplified by PCR using a forward primer comprising the nucleotide sequence of SEQ ID NO: 20 and a reverse primer comprising the nucleotide sequence of SEQ ID NO: 21.

In a specific embodiment, "the portion consisting of a nucleotide sequence corresponding to SEQ ID NO: 130" includes, for instance, a portion of the genome of a *Stevia* plant which can be amplified by PCR using a forward primer comprising the nucleotide sequence of SEQ ID NO: 131 and a reverse primer comprising the nucleotide sequence of SEQ ID NO: 132.

In a specific embodiment, "the allele wherein the base at the position corresponding to position 40 of SEQ ID NO: 1 is C" comprises the nucleotide sequence of SEQ ID NO: 22, 23, 24 or 25.

In a specific embodiment, "the allele wherein the base at the position corresponding to position 21 of SEQ ID NO: 2 is T" comprises the nucleotide sequence of SEQ ID NO: 26, 27, 28 or 29.

In a specific embodiment, "the allele wherein the base at the position corresponding to position 28 of SEQ ID NO: 3 is T" comprises the nucleotide sequence of SEQ ID NO: 30, 31, 32 or 33.

In a specific embodiment, "the allele wherein the base at the position corresponding to position 59 of SEQ ID NO: 4 is C" comprises the nucleotide sequence of SEQ ID NO: 34, 35, 36 or 37.

In a specific embodiment, "the allele wherein the base at the position corresponding to position 64 of SEQ ID NO: 5 is T" comprises the nucleotide sequence of SEQ ID NO: 38, 39, 40 or 41.

In a specific embodiment, "the allele wherein the base at the position corresponding to position 290 of SEQ ID NO: 6 is C" comprises the nucleotide sequence of SEQ ID NO: 42, 43, 44 or 45.

In a specific embodiment, "the allele wherein the base at the position corresponding to position 33 of SEQ ID NO: 7 is T" comprises the nucleotide sequence of SEQ ID NO: 46, 47, 48 or 49.

In a specific embodiment, "the allele wherein the base at the position corresponding to position 40 of SEQ ID NO: 130 is T" comprises the nucleotide sequence of SEQ ID NO: 133, 134, 135 or 136.

Also, a variation selected from the group consisting of (A) a variation from T to C at a position corresponding to position 40 of SEQ ID NO: 1, (B) a variation from A to T at a position corresponding to position 40 of SEQ ID NO: 2, (C) a variation from C to T at a position corresponding to position 28 of SEQ ID NO: 3, (D) a variation from A to C at a position corresponding to position 59 of SEQ ID NO: 4, (E) a variation from C to T at a position corresponding to position 64 of SEQ ID NO: 5, (F) a variation from T to C at a position corresponding to position 290 of SEQ ID NO: 6, and (G) a variation from A to T at a position corresponding to position 33 of SEQ ID NO: 7 may be generically referred to as a "polymorphism of the present invention" or a "variation of the present invention". Also, each of the above variations (A) to (G) may be referred to as a "polymorphism (A) of the present invention", "polymorphism (B) of the present invention", a "variation (A) of the present invention", a "variation (B) of the present invention", or the like. Further, a variation from G to C at a position corresponding to position 40 of SEQ ID NO: 130 may be referred to as a "polymorphism (H) of the present invention" or a "variation (H) of the present invention".

The above genetic features can be detected by PCR method, TaqMan PCR method, sequencing method, microarray method, Invader method, TILLING method, RAD (random amplified polymorphic DNA) method, restriction fragment length polymorphism (RFLP) method, PCR-SSCP method, AFLP (amplified fragment length polymorphism) method, SSLP (simple sequence length polymorphism) method, CAPS (cleaved amplified polymorphic sequence) method, dCAPS (derived cleaved amplified polymorphic sequence) method, allele-specific oligonucleotide (ASO) method, ARMS method, denaturing gradient gel electrophoresis (DGGE) method, CCM (chemical cleavage of mismatch) method, DOL method, MALDI-TOF/MS method, TDI method, padlock probe method, molecular beacon method, DASH (dynamic allele specific hybridization) method, UCAN method, ECA method, PINPOINT method, PROBE (primer oligo base extension) method, VSET (very short extension) method, Survivor assay, Sniper assay, Luminex assay, GOOD method, LCx method, SNaPshot method, Mass ARRAY method, pyrosequencing method, SNP-IT method, melting curve analysis method, etc., but detection methods are not limited thereto.

In a specific embodiment, each genetic feature of the present invention is detectable by dCAPS method using the following combination of a primer set and a restriction enzyme.

In case a candidate plant has the variation (A), for example, only a band of approximately 203 bp long (e.g., SEQ ID NO: 52) is obtained by: performing PCR amplification using a forward primer having the nucleotide sequence shown in SEQ ID NO: 50 and a reverse primer having the nucleotide sequence shown in SEQ ID NO: 51 on the genomic DNA of the candidate plant; and treating the obtained PCR product (approximately 203 bp long, e.g., SEQ ID NO: 52) with a restriction enzyme RsaI. On the other hand, in case the candidate plant does not have the variation (A) (the base at the position corresponding to position 40 of SEQ ID NO: 1 is T), a band of approximately 40 bp long (e.g., SEQ ID NO: 54) and a band of approximately 163 bp long (e.g., SEQ ID NO: 55) are obtained by: performing PCR amplification in the same way as above; and treating the obtained PCR product (approximately 203 bp long, e.g., SEQ ID NO: 53) with a restriction enzyme RsaI. An example in which the genetic feature (A) was detected by the above approach is shown in FIG. 8. Lane 1 was loaded with a sample prepared by treating DNA of a *Stevia* individual homozygous for the allele having the variation (A) with the restriction enzyme RsaI. Lane 2 was loaded with a sample prepared by treating DNA of a *Stevia* individual heterozygous for the allele having the variation (A) (i.e., an individual having the genetic feature (A) of the present invention) with the restriction enzyme RsaI. Lane 3 was loaded with a sample prepared by treating DNA of a *Stevia* individual homozygous for the allele not having the variation (A) with the restriction enzyme RsaI. The band of approximately 40 bp long and the band of approximately 163 bp long from enzymatic degradation, and the band of approximately 203 bp long without enzymatic degradation are found in the lane 2. Thus, the candidate plant can be determined as having the genetic feature (A) of the present invention, when the band of approximately 40 bp long and/or the band of approximately 163 bp long derived from a degraded product, and the band of approximately 203 bp long derived from a non-degraded product are found by the above dCAPS method.

In case a candidate plant has the variation (B), for example, a band of approximately 18 bp long (e.g., SEQ ID NO: 60) and a band of approximately 346 bp long (e.g., SEQ ID NO: 61) are obtained by: performing PCR amplification using a forward primer having the nucleotide sequence shown in SEQ ID NO: 56 and a reverse primer having the nucleotide sequence shown in SEQ ID NO: 57 on the genomic DNA of the candidate plant; and treating the obtained PCR product (approximately 364 bp long, e.g., SEQ ID NO: 58) with a restriction enzyme AclI. On the other hand, in case the candidate plant does not have the variation (B), only a band of approximately 364 bp long (e.g., SEQ ID NO: 59) is obtained by: performing PCR amplification in the same way as above; and treating the obtained PCR product (approximately 364 bp long, e.g., SEQ ID NO: 59) with a restriction enzyme AclI. Thus, the candidate plant can be determined as having the genetic feature (B) of the present invention, when the band of approximately 18 bp long and/or the band of approximately 346 bp long derived from a degraded product, and the band of approximately 364 bp long derived from a non-degraded product are found by the above dCAPS method.

In case a candidate plant has the variation (C), for example, a band of approximately 19 bp long (e.g., SEQ ID NO: 66) and a band of approximately 334 bp long (e.g., SEQ ID NO: 67) are obtained by: performing PCR amplification using a forward primer having the nucleotide sequence shown in SEQ ID NO: 62 and a reverse primer having the nucleotide sequence shown in SEQ ID NO: 63 on the genomic DNA of the candidate plant; and treating the obtained PCR product (approximately 353 bp long, e.g., SEQ ID NO: 64) with a restriction enzyme AluI. On the other hand, in case the candidate plant does not have the variation (C), only a band of approximately 353 bp long (e.g., SEQ ID NO: 65) is obtained by: performing PCR amplification in the same way as above; and treating the obtained PCR product (approximately 353 bp long, e.g., SEQ ID NO: 65) with a restriction enzyme AluI. Thus, the candidate plant can be determined as having the genetic feature (C) of the present invention, when the band of approximately 19 bp long and/or the band of approximately 334 bp long derived from a degraded product, and the band of approximately 353 bp long derived from a non-degraded product are found by the above dCAPS method.

In case a candidate plant has the variation (D), for example, a band of approximately 21 bp long (e.g., SEQ ID NO: 72) and a band of approximately 328 bp long (e.g., SEQ ID NO: 73) are obtained by: performing PCR amplification using a forward primer having the nucleotide sequence shown in SEQ ID NO: 68 and a reverse primer having the nucleotide sequence shown in SEQ ID NO: 69 on the genomic DNA of the candidate plant; and treating the obtained PCR product (approximately 349 bp long, e.g., SEQ ID NO: 70) with a restriction enzyme AluI. On the other hand, in case the candidate plant does not have the variation (D), only a band of approximately 349 bp long (e.g., SEQ ID NO: 71) is obtained by: performing PCR amplification in the same way as above; and treating the obtained PCR product (approximately 349 bp long, e.g., SEQ ID NO: 71) with a restriction enzyme AluI. Thus, the candidate plant can be determined as having the genetic feature (D) of the present invention, when the band of approximately 21 bp long and/or the band of approximately 328 bp long derived from a degraded product, and the band of approximately 349 bp long derived from a non-degraded product are found by the above dCAPS method.

In case a candidate plant has the variation (E), for example, a band of approximately 21 bp long (e.g., SEQ ID NO: 78) and a band of approximately 328 bp long (e.g., SEQ ID NO: 79) are obtained by: performing PCR amplification using a forward primer having the nucleotide sequence shown in SEQ ID NO: 74 and a reverse primer having the nucleotide sequence shown in SEQ ID NO: 75 on the genomic DNA of the candidate plant; and treating the obtained PCR product (approximately 349 bp long, e.g., SEQ ID NO: 76) with a restriction enzyme AluI. On the other hand, in case the candidate plant does not have the variation (E), only a band of approximately 349 bp long (e.g., SEQ ID NO: 77) is obtained by: performing PCR amplification in the same way as above; and treating the obtained PCR product (approximately 349 bp long, e.g., SEQ ID NO: 77) with a restriction enzyme AluI. Thus, the candidate plant can be determined as having the genetic feature (E) of the present invention, when the band of approximately 21 bp long and/or the band of approximately 328 bp long derived from a degraded product, and the band of approximately 349 bp long derived from a non-degraded product are found by the above dCAPS method.

In case a candidate plant has the variation (F), for example, only a band of approximately 326 bp long (e.g., SEQ ID NO: 82) is obtained by: performing PCR amplification using a forward primer having the nucleotide sequence shown in SEQ ID NO: 80 and a reverse primer having the nucleotide sequence shown in SEQ ID NO: 81 on the genomic DNA of the candidate plant; and treating the obtained PCR product (approximately 326 bp long, e.g., SEQ ID NO: 82) with a restriction enzyme RsaI. On the other hand, in case the candidate plant does not have the variation (F) (the base at the position corresponding to position 290 of SEQ ID NO: 6 is T), a band of approximately 290 bp long (e.g., SEQ ID NO: 84) and a band of approximately 36 bp long (e.g., SEQ ID NO: 85) are obtained by: performing PCR amplification in the same way as above; and treating the obtained PCR product (approximately 326 bp long, e.g., SEQ ID NO: 83) with a restriction enzyme RsaI. Thus, the candidate plant can be determined as having the genetic feature (F) of the present invention, when the band of approximately 36 bp long and/or the band of approximately 290 bp long derived from a degraded product, and the band of approximately 326 bp long derived from a non-degraded product are found by the above dCAPS method.

In case a candidate plant has the variation (G), for example, only a band of approximately 196 bp long (e.g., SEQ ID NO: 88) is obtained by: performing PCR amplification using a forward primer having the nucleotide sequence shown in SEQ ID NO: 86 and a reverse primer having the nucleotide sequence shown in SEQ ID NO: 87 on the genomic DNA of the candidate plant; and treating the obtained PCR product (approximately 196 bp long, e.g., SEQ ID NO: 88) with a restriction enzyme MseI. On the other hand, in case the candidate plant does not have the variation (G) (the base at the position corresponding to position 33 of SEQ ID NO: 7 is A), a band of approximately 30 bp long (e.g., SEQ ID NO: 90) and a band of approximately 166 bp long (e.g., SEQ ID NO: 91) are obtained by: performing PCR amplification in the same way as above; and treating the obtained PCR product (approximately 196 bp long, e.g., SEQ ID NO: 89) with a restriction enzyme MseI. Thus, the candidate plant can be determined as having the genetic feature (G) of the present invention, when the band of approximately 30 bp long and/or the band of approximately 166 bp long derived from a degraded product, and the band of approximately 196 bp long derived from a non-degraded product are found by the above dCAPS method.

In case a candidate plant has the variation (H), for example, a band of approximately 37 bp long (e.g., SEQ ID NO: 141) and a band of approximately 463 bp long (e.g., SEQ ID NO: 142) are obtained by: performing PCR amplification using a forward primer having the nucleotide sequence shown in SEQ ID NO: 137 and a reverse primer having the nucleotide sequence shown in SEQ ID NO: 138 on the genomic DNA of the candidate plant; and treating the obtained PCR product (approximately 500 bp long, e.g., SEQ ID NO: 139) with a restriction enzyme EcoRV. On the other hand, in case the candidate plant does not have the variation (H), only a band of approximately 500 bp long (e.g., SEQ ID NO: 140) is obtained by: performing PCR amplification in the same way as above; and treating the obtained PCR product (approximately 500 bp long, e.g., SEQ ID NO: 140) with a restriction enzyme EcoRV. Thus, the candidate plant can be determined as having the genetic feature (H) of the present invention, when the band of approximately 37 bp long and/or the band of approximately 463 bp long derived from a degraded product, and the band of approximately 500 bp long derived from a non-degraded product are found by the above dCAPS method.

The term "approximately" as to bp long described above means±5 bp. The restriction enzyme treatment can be performed according to conditions recommended by the distributor of each restriction enzyme used.

In some embodiments, the plant B of the present invention may have a plurality of the above genetic features (A) to (G). In these embodiments, the number of genetic features may be any of 2 to 7, i.e., 2, 3, 4, 5, 6 or 7. The combination of the genetic features is not particularly limited and includes, for example, each of the following combinations within the parentheses: (A, B), (A, C), (A, D), (A, E), (A, F), (A, G), (B, C), (B, D), (B, E), (B, F), (B, G), (C, D), (C, E), (C, F), (C, G), (D, E), (D, F), (D, G), (E, F), (E, G), (F, G), (A, B, C), (A, B, D), (A, B, E), (A, B, F), (A, B, G), (A, C, D), (A, C, E), (A, C, F), (A, C, G), (A, D, E), (A, D, F), (A, D, G), (A, E, F), (A, E, G), (A, F, G), (B, C, D), (B, C, E), (B, C, F), (B, C, G), (B, D, E), (B, D, F), (B, D, G), (B, E, F), (B, E, G), (B, F, G), (C, D, E), (C, D, F), (C, D, G), (C, E, F), (C, E, G), (C, F, G), (D, E, F), (D, E, G), (D, F, G), (E, F, G), (A, B, C, D), (A, B, C, E), (A, B, C, F), (A, B, C, G), (A, B, D, E), (A, B, D, F), (A, B, D, G), (A, B, E, F), (A, B, E, G), (A, B, F, G), (A, C, D, E), (A, C, D, F), (A, C, D, G), (A, C, E, F), (A, C, E, G), (C, F, G), (D, E, F), (D, E, G), (D, F, G), (E, F, G), (B, C, D, E), (B, C, D, F), (B, C, D, G), (B, C, E, F), (B, C, E, G), (B, C, F, G), (B, D, E, F), (B, D, E, G), (B, D, F, G), (B, E, F, G), (C, D, E, F), (C, D, E, G), (C, D, F, G), (C, E, F, G), (D, E, F, G), (A, B, C, D, E), (A, B, C, D, F), (A, B, C, D, G), (A, B, C, E, F), (A, B, C, E, G), (A, B, C, F, G), (A, B, D, E, F), (A, B, D, E, G), (A, B, D, F, G), (A, B, E, F, G), (A, C, D, E, F), (A, C, D, E, G), (A, C, D, F, G), (A, C, E, F, G), (A, D, E, F, G), (B, C, D, E, F), (B, C, D, E, G), (B, C, D, F, G), (B, C, E, F, G), (B, D, E, F, G), (C, D, E, F, G), (A, B, C, D, E, F), (A, B, C, D, E, G), (A, B, C, D, F, G), (A, B, C, E, F, G), (A, B, D, E, F, G), (A, C, D, E, F, G), (B, C, D, E, F, G) and (A, B, C, D, E, F, G). In the above, for example, (A, B) means the combination of the genetic feature (A) and the genetic feature (B).

In some embodiments, the plant D of the present invention may further have a plurality of the above genetic features (A) to (G). In these embodiments, the number of genetic features may be any of 2 to 8, i.e., 2, 3, 4, 5, 6, 7 or 8. The combination of the genetic features is not particularly limited and includes, for example, each of the following combinations within the parentheses: (A, H), (B, H), (C, H), (D, H), (E, H), (F, H), (G, H), (A, B, H), (A, C, H), (A, D, H), (A, E, H), (A, F, H), (A, G, H), (B, C, H), (B, D, H), (B, E, H), (B, F, H), (B, G, H), (C, D, H), (C, E, H), (C, F, H), (C, G, H), (D, E, H), (D, F, H), (D, G, H), (E, F, H), (E, G, H), (F, G, H), (A, B, C, H), (A, B, D, H), (A, B, E, H), (A, B, F, H), (A, B, G, H), (A, C, D, H), (A, C, E, H), (A, C, F, H), (A, C, G, H), (A, D, E, H), (A, D, F, H), (A, D, G, H), (A, E, F, H), (A, E, G, H), (A, F, G, H), (B, C, D, H), (B, C, E, H), (B, C, F, H), (B, C, G, H), (B, D, E, H), (B, D, F, H), (B, D, G, H), (B, E, F, H), (B, E, G, H), (B, F, G, H), (C, D, E, H), (C, D, F, H), (C, D, G, H), (C, E, F, H), (C, E, G, H), (C, F, G, H), (D, E, F, H), (D, E, G, H), (D, F, G, H), (E, F, G, H), (A, B, C, D, H), (A, B, C, E, H), (A, B, C, F, H), (A, B, C, G, H), (A, B, D, E, H), (A, B, D, F, H), (A, B, D, G, H), (A, B, E, F, H), (A, B, E, G, H), (A, B, F, G, H), (A, C, D, E, H), (A, C, D, F, H), (A, C, D, G, H), (A, C, E, F, H), (A, C, E, G, H), (C, F, G, H), (D, E, F, H), (D, E, G, H), (D, F, G, H), (E, F, G, H), (B, C, D, E, H), (B, C, D, F, H), (B, C, D, G, H), (B, C, E, F, H), (B, C, E, G, H), (B, C, F, G, H), (B, D, E, F, H), (B, D, E, G, H), (B, D, F, G, H), (B, E, F, G, H), (C, D, E, F, H), (C, D, E, G, H), (C, D, F, G, H), (C, E, F, G, H), (D, E, F, G, H), (A, B, C, D, E, H), (A, B, C, D, F, H), (A, B, C, D, G, H), (A, B, C, E, F, H), (A, B, C, E, G, H), (A, B, C, F, G, H), (A, B, D, E, F, H), (A, B, D, E, G, H), (A, B, D, F, G, H), (A, B, E, F, G, H), (A, C, D, E, F, H), (A, C, D, E, G, H), (A, C, D, F, G, H), (A, C, E, F, G, H), (A, D, E, F, G, H), (B, C, D, E, F, H), (B, C, D, E, G, H), (B, C, D, F, G, H), (B, C, E, F, G, H), (B, D, E, F, G, H), (C, D, E, F, G, H), (A, B, C, D, E, F, H), (A, B, C, D, E, G, H), (A, B, C, D, F, G, H), (A, B, C, E, F, G, H), (A, B, D, E, F, G, H), (A, C, D, E, F, G, H), (B, C, D, E, F, G, H) and (A, B, C, D, E, F, G, H).

The variation sites (A) to (E) of the present invention are positioned as adjacent as within 173 bp to each other on the genome and are in linkage disequilibrium. Thus, the plant B of the present invention having any of the genetic features (A) to (E) tends to have the other genetic features (A) to (E).

The presence of the genetic features (A) to (H) of the present invention is highly related to the presence of the chemical features (1) to (7) of the present invention. Hence, a *Stevia* plant having at least one of the genetic features (A) to (H) of the present invention is likely to have the chemical features (1) to (7) of the present invention, and a *Stevia* plant having at least one of the chemical features (1) to (7) of the present invention may be screened for by using at least one of the genetic features (A) to (H) of the present invention as an index.

In a specific embodiment, the present invention provides a *Stevia* plant having at least one of the chemical features (1) to (7) and at least one of the genetic features (A) to (G) (hereinafter, may be generically referred to as "plant C of the present invention" or "*Stevia* plant C of the present invention").

In some embodiments, the plant C of the present invention has at least one of the chemical features (1) to (7) and at least one of the genetic features (A) to (E). In some embodiments, the plant C of the present invention has at least one of the chemical features (1) to (7) and the genetic feature (F). In some embodiments, the plant C of the present invention has at least one of the chemical features (1) to (7) and the genetic feature (G). In a specific embodiment, the plant C of the present invention has at least one of the chemical features (1) to (7), at least one of the genetic features (A) to (E), and the genetic feature (F). In a specific embodiment, the plant C of the present invention has at least one of the chemical features (1) to (7), at least one of the genetic features (A) to (E), and the genetic feature (G). In a specific embodiment, the plant C of the present invention has at least one of the chemical features (1) to (7), at least one of the genetic features (A) to (E), and the genetic features (F) and (G).

The plants A to C of the present invention may be generically referred to as a "plant of the present invention".

In a specific embodiment, the present invention provides a *Stevia* plant having at least one of the chemical features (1) to (7) and the genetic feature (H) (hereinafter, may be generically referred to as "plant E of the present invention" or "*Stevia* plant E of the present invention"). The plant E of the present invention may further have at least one of the genetic features (A) to (G).

In some embodiments, the plant E of the present invention has at least one of the chemical features (1) to (7), the genetic feature (H) and at least one of the genetic features (A) to (E). In some embodiments, the plant E of the present invention has at least one of the chemical features (1) to (7), the genetic feature (H) and the genetic feature (F). In some embodiments, the plant E of the present invention has at least one of the chemical features (1) to (7), the genetic feature (H) and the genetic feature (G). In a specific embodiment, the plant E of the present invention has at least one of the chemical features (1) to (7), the genetic feature (H), at least one of the genetic features (A) to (E), and the genetic feature (F). In a specific embodiment, the plant E of the present invention has at least one of the chemical features (1) to (7), the genetic feature (H), at least one of the genetic features (A) to (E), and the genetic feature (G). In a specific embodiment, the plant E of the present invention has at least one of the chemical features (1) to (7), the genetic feature (H), at least one of the genetic features (A) to (E), and the genetic features (F) and (G).

The steviol glycosides such as RebD, RebM and RebN can be extracted in the state of a liquid extract by reacting a fresh leaf or a dried leaf of the plant A to E of the present invention with a suitable solvent (an aqueous solvent such as water or an organic solvent such as an alcohol, ether or acetone). For the extraction conditions, etc., see a method described in Ohta et al., J. Appl. Glycosci., Vol. 57, No. 3, 199-209 (2010) or WO2010/038911, or a method described in Examples mentioned later.

Individual steviol glycosides, for example, RebD and RebM, can be further purified from the liquid extract thus obtained by use of a method known in the art such as a gradient of ethyl acetate or any of other organic solvents: water, high performance liquid chromatography (HPLC), gas chromatography, time-of-flight mass spectrometry (TOF-MS), or ultra (high) performance liquid chromatography (UPLC).

The contents of the steviol glycosides such as RebD, RebM and RebN can be measured by a method described in Ohta et al., supra or WO2010/038911, or a method described in Examples mentioned later. Specifically, for instance, a fresh leaf can be sampled from the *Stevia* plant A to E of the present invention, followed by measurement by LC-MS/MS and the like.

The plant A to E of the present invention may be the one obtained by a genetic modification approach or a progeny thereof (hereinafter, may be referred to as "genetically modified plant") or the one obtained by a non-genetic modification approach or a progeny thereof (hereinafter, may be referred to as "non-genetically modified plant"). Examples of the "non-genetic modification approach" include, besides hybridization, selfing, and the like, a method of inducing a variation in the gene of a host cell (or a host plant) without transfection with a foreign gene. Examples of such a method include a method of allowing a mutagen to act on a plant cell. Examples of such a mutagen include ethyl methanesulfonate (EMS) and sodium azide. For example, EMS can be used at a concentration such as 0.1%, 0.2%, 0.3%, 0.4%, 0.5%, 0.6%, 0.7%, 0.8%, 0.9%, or 1.0% to treat a plant cell. The treatment time is 1 to 48 hours, 2 to 36 hours, 3 to 30 hours, 4 to 28 hours, 5 to 26 hours, or 6 to 24 hours. The procedures themselves of the treatment are known in the art and can be performed by dipping a water-absorbed seed obtained through a water absorption process in a treatment solution containing the mutagen at the concentration described above for the treatment time described above.

An alternative example of the non-genetic modification approach can be a method of irradiating a plant cell with radiation or light beam such as X-ray, y ray, or ultraviolet ray. In this case, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity is 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, or 1 to 10 Gr. The irradiation distance is 1 cm to 200 in, 5 cm to 100 m, 7 cm to 75 m, 9 cm to 50 m, 10 cm to 30 m, 10 cm to 20 in, or 10 cm to 10 n. The irradiation time is 1 minute to 2 years, 2 minutes to 1 year, 3 minutes to 0.5 years, 4 minutes to 1 month, 5 minutes to 2 weeks, or 10 minutes to 1 week. The irradiation intensity, distance and time differ depending on the type of radiation or the state of the subject to be irradiated (cell, callus, or plant) and can be appropriately adjusted by those skilled in the art.

Approaches such as cell fusion, anther culture (haploid induction), and remote crossing (haploid induction) are also known in the art.

In general, plant cells may involve a mutation during culture. Therefore, it is preferred to regenerate a plant individual, for more stably maintaining the trait.

The scope of the present invention does not exclude a plant obtained by the ex-post facto genetic recombination (e.g., genome editing) with the plant A to E of the present invention as a host (e.g., a plant further provided with another trait by genetic recombination with the plant A to E of the present invention as a host).

The plant A to E of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like. The leaf may be a dried leaf.

The plant A to E of the present invention may also include a tissue culture or a cultured plant cell. This is because the plant can be regenerated by culturing such a tissue culture or a cultured plant cell. Examples of a regenerable form of the plant A to E of the present invention include, but are not limited to, embryos, meristem cells, pollens, leaves, roots, root apices, petals, protoplasts, leaf sections and calluses.

2. Method of Producing Plant of Present Invention

In an alternative aspect, the present invention provides a method of producing a *Stevia* plant having at least one of the chemical features (1) to (7), the method comprising a step of crossing the *Stevia* plant of the present invention with a second *Stevia* plant (hereinafter, may be referred to as the "production method A of the present invention").

The *Stevia* plant produced by the method may have the same phenotype and genetic features as those of the plant of the present invention.

In an alternative aspect, the present invention also provides a method of producing a *Stevia* plant having at least one of the chemical features (1) to (7), the method comprising a step of crossing the *Stevia* plant D or E of the present invention with a second *Stevia* plant (hereinafter, may be referred to as the "production method B of the present invention").

The *Stevia* plant produced by the method may have the same phenotype and genetic features as those of the plant D or E of the present invention.

The ranges of the amount of RebD, the amount of RebN, the total amount of RebD and RebM, the total amount of RebD and RebN, and the total amount of RebD, RebM and RebN in the plant obtained by the production methods A to B of the present invention, the ranges of the ratios of the amount of RebD and the total amount of RebD and RebM to the amount of TSG, the combination of each feature (chemical feature and/or genetic feature), and the like are as described above about the plant of the present invention.

In the production methods A to B of the present invention, "hybridizing" means that at least one of the plants A to E of the present invention (first generation (S1)) is crossed with a second plant (S1) to obtain a progeny plant thereof (plant produced by the production method of the present invention (second generation (S2)). The hybridizing method is preferably backcross. The "backcross", for instance, is an approach of further crossing a progeny plant (S2) generated between the plant of the present invention and the second plant, with the plant of the present invention (i.e., a plant having the genetic feature(s) of the present invention) (S1) to produce a plant having the genetic feature(s) of the present invention. When the second plant (S1) for use in the production method of the present invention has the same phenotype and genetic features as those of the plant of the present invention, the crossing is substantially backcross. Hybridization is preferably performed over two generations or more, but in case where the genetic feature is heterozygous, etc., a plant having a desired combination of genetic features may be obtained in one generation.

Alternatively, the plants A to E of the present invention can also be produced by selfing. The selfing can be performed by the self-pollination of the stamen pollen of the plant of the present invention with the pistil of the plants A to E of the present invention.

Since the plant produced by the production method of the present invention has the same phenotype and genetic features as those of the plant of the present invention, the plant produced by the production method of the present invention can be further crossed with a third *Stevia* plant to produce a *Stevia* plant having a phenotype equivalent to that of the plant of the present invention.

In an alternative embodiment, the plants A to E of the present invention may be produced by regenerating a plant by the culture of the tissue culture or the cultured plant cell mentioned above. The culture conditions are the same as those for culturing a tissue culture or a cultured plant cell of the wild type *Stevia* plant and are known in the art (Protocols for in vitro cultures and secondary metabolite analysis of aromatic and medicinal plants, Method in molecular biology, vol. 1391, pp. 113-123).

In a further alternative embodiment, the plant of the present invention may be produced by introducing the variation of the present invention to the genome of a *Stevia* plant. Furthermore, the plants D to E of the present invention and the *Stevia* plant having at least one of the chemical features (1) to (7) may be produced by introducing the variation (H) of the present invention to the genome of a *Stevia* plant. The introduction of the variation may be performed by a genetic modification approach or may be performed by a non-genetic modification approach. The "non-genetic modification approach" is as described above with respect to the plant of the present invention.

3. Method of Screening for Plant of Present Invention

The plant of the present invention or the plant having the same phenotype and/or genetic feature as those of the plant of the present invention can be screened for by detecting the genetic feature(s) of the present invention from a tissue of this plant. In this context, "screening" means that the plant of the present invention is discriminated from the other plants to select the plant of the present invention.

Thus, in an alternative aspect, the present invention provides a method of screening for a *Stevia* plant, comprising a step of detecting the presence and/or the absence of at least one of the genetic features (A) to (G) of the present invention from the genome of a test plant (hereinafter, may be referred to as the "screening method A of the present invention").

In one embodiment, the genetic feature(s) to be detected is at least one of the genetic features (A) to (E) (particularly, the genetic feature (A)). In another embodiment, the genetic feature(s) to be detected is the genetic feature (F). In another embodiment, the genetic feature(s) to be detected is the genetic feature (G). In some embodiments, the genetic feature(s) to be detected is at least one of the genetic features (A) to (E) and the genetic feature (F). In some embodiments, the genetic feature(s) to be detected is at least one of the genetic features (A) to (E) and the genetic feature (G). In some embodiments, the genetic feature(s) to be detected is the genetic feature (F) and the genetic feature (G). In some embodiments, the genetic feature(s) to be detected is the genetic features (A), (F) and (G). As described above, since the variations related to the genetic features (A) to (E) are in linkage disequilibrium, the detection of any one of these genetic features allows the presence or absence of the remaining genetic features to be predicted.

In an alternative aspect, the present invention provides a method of screening for a *Stevia* plant having the genetic feature (H) or a *Stevia* plant having at least one of the chemical features (1) to (7), comprising a step of detecting the presence and/or the absence of the genetic feature (H) of the present invention from the genome of a test plant (hereinafter, may be referred to as the "screening method B of the present invention").

In one embodiment, the genetic feature to be detected is the genetic feature (H). In some embodiments, the genetic features to be detected are at least one of the genetic features (A) to (E) and the genetic feature (H). In some embodiments, the genetic features to be detected is the genetic feature (F) and the genetic feature (H). In some embodiments, the genetic features to be detected are the genetic feature (G) and the genetic feature (H). In some embodiments, the genetic features to be detected are at least one of the genetic features (A) to (E), the genetic feature (F) and the genetic feature (H). In some embodiments, the genetic features to be detected are at least one of the genetic features (A) to (E), the genetic feature (G) and the genetic feature (H). In some embodiments, the genetic features to be detected are the genetic feature (F), the genetic feature (G) and the genetic feature (H). In some embodiments, the genetic features to be detected are the genetic features (A), (F), (G) and (H). The screening methods A to B of the present invention may further comprise a step of selecting from among the test plants a plant in which the presence of at least one genetic feature of the above is detected.

The presence of the genetic feature(s) of the present invention can be determined, for example, by detecting:

(I) the presence of both of an allele wherein the base at the position corresponding to position 40 of SEQ ID NO: 1 is C (e.g., an allele comprising the nucleotide sequence of SEQ ID NO: 22, 23, 24 or 25; hereinafter, may be referred to as "allele a") and an allele wherein the base at the position corresponding to position 40 of SEQ ID NO: 1 is T (e.g., an allele comprising the nucleotide sequence of SEQ ID NO: 1, 92, 93 or 94; hereinafter, may be referred to as "allele A");

(II) the presence of both of an allele wherein the base at the position corresponding to position 21 of SEQ ID NO: 2 is T (e.g., an allele comprising the nucleotide sequence of SEQ ID NO: 26, 27, 28 or 29; hereinafter, may be referred to as "allele b") and an allele wherein the base at the position corresponding to position 21 of SEQ ID NO: 2 is A (e.g., an allele comprising the nucleotide sequence of SEQ ID NO: 2, 95, 96 or 97; hereinafter, may be referred to as "allele B");

(III) the presence of both of an allele wherein the base at the position corresponding to position 28 of SEQ ID NO: 3 is T (e.g., an allele comprising the nucleotide sequence of SEQ ID NO: 30, 31, 32 or 33; hereinafter, may be referred to as "allele c") and an allele wherein the base at the position corresponding to position 28 of SEQ ID NO: 3 is C (e.g., an allele comprising the nucleotide sequence of SEQ ID NO: 3, 98, 99 or 100; hereinafter, may be referred to as "allele C");

(IV) the presence of both of an allele wherein the base at the position corresponding to position 59 of SEQ ID NO: 4 is C (e.g., an allele comprising the nucleotide sequence of SEQ ID NO: 34, 35, 36 or 37; hereinafter, may be referred to as "allele d") and an allele wherein the base at the position corresponding to position 59 of SEQ ID NO: 4 is A (e.g., an allele comprising the nucleotide sequence of SEQ ID NO: 4, 101, 102 or 103; hereinafter, may be referred to as "allele D");

(V) the presence of both of an allele wherein the base at the position corresponding to position 64 of SEQ ID NO: 5 is T (e.g., an allele comprising the nucleotide sequence of SEQ ID NO: 38, 39, 40 or 41; hereinafter, may be referred to as "allele e") and an allele wherein the base at the position corresponding to position 64 of SEQ ID NO: 5 is C (e.g., an allele comprising the nucleotide sequence of SEQ ID NO: 5, 104, 105 or 106; hereinafter, may be referred to as "allele E");

(VI) the presence of both of an allele wherein the base at the position corresponding to position 290 of SEQ ID NO: 6 is C (e.g., an allele comprising the nucleotide sequence of SEQ ID NO: 42, 43, 44 or 45; hereinafter, may be referred to as "allele f") and an allele wherein the base at the position corresponding to position 290 of SEQ ID NO: 6 is T (e.g., an allele comprising the nucleotide sequence of SEQ ID NO: 6, 107, 108 or 109; hereinafter, may be referred to as "allele F"); and/or (VII) the presence of both of an allele wherein the base at the position corresponding to position 33 of SEQ ID NO: 7 is T (e.g., an allele comprising the nucleotide sequence of SEQ ID NO: 46, 47, 48 or 49; hereinafter, may be referred to as "allele g") and an allele wherein the base at the position corresponding to position 33 of SEQ ID NO: 7 is A (e.g., an allele comprising the nucleotide sequence of SEQ ID NO: 7, 110, 111 or 112; hereinafter, may be referred to as "allele G").

Further, the presence of the genetic feature (H) of the present invention can be determined, for example, by detecting the presence of both of an allele wherein the base at the position corresponding to position 40 of SEQ ID NO: 130 is C (e.g., an allele comprising the nucleotide sequence of SEQ ID NO: 133, 134, 135 or 136; hereinafter, may be referred to as "allele h") and an allele wherein the base at the position corresponding to position 40 of SEQ ID NO: 130 is T (e.g., an allele comprising the nucleotide sequence of SEQ ID NO: 130, 143, 144 or 145; hereinafter, may be referred to as "allele H").

The absence of the genetic feature(s) of the present invention can be determined, for example, by detecting:

(i) the presence of only any one of the allele A and the allele a;

(ii) the presence of only any one of the allele B and the allele b;

(iii) the presence of only any one of the allele C and the allele c;

(iv) the presence of only any one of the allele D and the allele d;

(v) the presence of only any one of the allele E and the allele e;

(vi) the presence of only any one of the allele F and the allele f; and/or (vii) the presence of only any one of the allele G and the allele g.

The absence of the genetic feature (H) of the present invention can be determined, for example, by detecting the presence of only any one of the allele H and the allele h.

Specific examples of methods of detecting the genetic features of the present invention include, but not limited to, PCR method, TaqMan PCR method, sequencing method, microarray method, Invader method, TILLING method, RAD method, RFLP method, PCR-SSCP method, AFLP method, SSLP method, CAPS method, dCAPS method, ASO method, ARMS method, DGGE method, CCM method, DOL method, MALDI-TOF/MS method, TDI method, padlock probe method, molecular beacon method, DASH method, UCAN method, ECA method, PINPOINT method, PROBE method, VSET method, Survivor assay, Sniper assay, Luminex assay, GOOD method, LCx method, SNaPshot method, Mass ARRAY method, pyrosequencing method, SNP-IT method, melting curve analysis method, etc.

In the case of PCR method, it is preferable to generate a primer such that the 3' end portion has a sequence complementary to any one of the variation sites (A) to (H) of the present invention. By using a primer designed in this way, the polymerase extension reaction proceeds because the primer hybridizes completely to the template if the template sample has the variation, whereas if the template does not have the variation of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has a variation, and if the amplification product is not present, it can be judged that the template does not have a variation.

Alternatively, the genetic features (A) to (H) of the present invention can be detected by designing the primer sequence so that the variation sites (A) to (H) of the present invention and the primer sequence do not overlap and the genetic variation of the present invention can be PCR amplified, and by sequencing the nucleotide sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqMan PCR method uses fluorescently labeled allele-specific oligos and Taq DNA polymerases (Livak, K. J. Genet. Anal. 14, 143 (1999); Morris T. et al., J. Clin. Microbiol. 34, 2933 (1996)).

The sequencing method is a method of analyzing the presence or absence of a variation by amplifying a region containing the variation by PCR and sequencing the DNA sequence using a Dye Terminator or the like (Sambrook, Fritsch and Maniatis, "Molecular Cloning: A Laboratory Manual" 2nd Edition (1989), Cold Spring Harbor Laboratory Press).

A DNA microarray is one in which one end of a nucleotide probe is immobilized in an array on a support, and includes a DNA chip, a Gene chip, a microchip, a bead array, and the like. By using a probe containing a sequence complementary to the variation sites (A) to (H) of the present invention, the presence or absence of the variations (A) to (H) of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele of a variation such as SNPs and one invader probe to template DNA and the cleavage of DNA by Cleavase enzyme with a special endonuclease activity which cleaves a DNA by recognizing its structure (Livak, K. J. Biomol. Eng. 14, 143-149 (1999); Morris T. et al., J. Clin. Microbiol. 34, 2933 (1996); Lyamichev, V. et al., Science, 260, 778-783 (1993), and the like).

TILLING (Targeting Induced Local Lesions IN Genomes) method is a method in which mutational mismatches in the genomes of a mutagenized mutant population are screened by PCR-amplification and CEL I nuclease-treatment.

In one embodiment, the genetic feature (A) of the present invention can be detected, for example, by dCAPS method using the following primer set and a restriction enzyme.

Primer Set:

A primer set comprising a forward primer comprising a continuous sequence of 15 to 39-base long from the 3' end of SEQ ID NO: 50 and a reverse primer comprising a sequence (e.g., SEQ ID NO: 51) complementary to any continuous sequence of 15 bases or more which is positioned at the 3' side of position 41 of SEQ ID NO: 1 or 22, or a primer set comprising a forward primer comprising a continuous sequence of 15 to 20-base long from the 3' end of SEQ ID NO: 113 or 114 and a reverse primer comprising a sequence (e.g., SEQ ID NO: 117) complementary to any continuous sequence of 15 bases or more which is positioned at the 3' side of position 22 of SEQ ID NO: 115 or 116.

Restriction Enzyme:

A restriction enzyme for the primer set based on SEQ ID NO: 50 includes RsaI, a restriction enzyme for the primer set based on SEQ ID NO: 113 includes Tsp45I, and a restriction enzyme for the primer set based on SEQ ID NO: 114 includes AciI.

In one embodiment, the genetic feature (B) of the present invention can be detected, for example, by dCAPS method using the following primer set and a restriction enzyme.

Primer Set:

A primer set comprising a forward primer comprising a continuous sequence of 15 to 20-base long from the 3' end of SEQ ID NO: 56, 118 or 119 and a reverse primer comprising a sequence (e.g., SEQ ID NO: 57) complementary to any continuous sequence of 15 bases or more which is positioned at the 3' side of position 22 of SEQ ID NO: 2 or 26.

Restriction Enzyme:

A restriction enzyme for the primer set based on SEQ ID NO: 56 includes AclI, a restriction enzyme for the primer set based on SEQ ID NO: 118 includes AluI, and a restriction enzyme for the primer set based on SEQ ID NO: 119 includes PacI.

In one embodiment, the genetic feature (C) of the present invention can be detected, for example, by dCAPS method using the following primer set and a restriction enzyme.

Primer Set:

A primer set comprising a forward primer comprising a continuous sequence of 15 to 20-base long from the 3' end of SEQ ID NO: 62, 120 or 121 and a reverse primer comprising a sequence (e.g., SEQ ID NO: 63) complementary to any continuous sequence of 15 bases or more which is positioned at the 3' side of position 22 of SEQ ID NO: 64 or 65.

Restriction Enzyme:

A restriction enzyme for the primer set based on SEQ ID NO: 62 includes AluI, a restriction enzyme for the primer set based on SEQ ID NO: 120 includes BglI, and a restriction enzyme for the primer set based on SEQ ID NO: 121 includes ScaI.

In one embodiment, the genetic feature (D) of the present invention can be detected, for example, by dCAPS method using the following primer set and a restriction enzyme.

Primer Set:

A primer set comprising a forward primer comprising a continuous sequence of 15 to 21-base long from the 3' end of SEQ ID NO: 68, 122 or 123 and a reverse primer comprising a sequence (e.g., SEQ ID NO: 69) complementary to any continuous sequence of 15 bases or more which is positioned at the 3' side of position 23 of SEQ ID NO: 70 or 71.

Restriction Enzyme:

A restriction enzyme for the primer set based on SEQ ID NO: 62 includes AluI, a restriction enzyme for the primer set based on SEQ ID NO: 122 includes MboI, and a restriction enzyme for the primer set based on SEQ ID NO: 123 includes BglII.

In one embodiment, the genetic feature (E) of the present invention can be detected, for example, by dCAPS method using the following primer set and a restriction enzyme.

Primer Set:

A primer set comprising a forward primer comprising a continuous sequence of 15 to 22-base long from the 3' end of SEQ ID NO: 74, 124 or 125 and a reverse primer comprising a sequence (e.g., SEQ ID NO: 75) complementary to any continuous sequence of 15 bases or more which is positioned at the 3' side of position 24 of SEQ ID NO: 76 or 77.

Restriction Enzyme:

A restriction enzyme for the primer set based on SEQ ID NO: 74 includes AluI, a restriction enzyme for the primer set based on SEQ ID NO: 124 includes MboI, and a restriction enzyme for the primer set based on SEQ ID NO: 124 includes BglII.

In one embodiment, the genetic feature (F) of the present invention can be detected, for example, by dCAPS method using the following primer set and a restriction enzyme.

Primer Set:

A primer set comprising a forward primer comprising a sequence (e.g., SEQ ID NO: 80) of any continuous sequence of 15 bases or more which is positioned at the 5' side of position 289 of SEQ ID NO: 6 or 42 and a reverse primer comprising a continuous sequence of 15 to 36-base long from the 3' end of SEQ ID NO: 81, 126 or 127.

Restriction Enzyme:

A restriction enzyme for the primer set based on SEQ ID NO: 81 includes RsaI, a restriction enzyme for the primer set based on SEQ ID NO: 126 includes SnaI, and a restriction enzyme for the primer set based on SEQ ID NO: 127 includes AluI.

In one embodiment, the genetic feature (G) of the present invention can be detected, for example, by dCAPS method using the following primer set and a restriction enzyme.

Primer Set:

A primer set comprising a forward primer comprising a continuous sequence of 15 to 32-base long from the 3' end of the sequence selected from SEQ ID NOs: 86, 128 and 129 and a reverse primer comprising a sequence (e.g., SEQ ID NO: 87) complementary to any continuous sequence of 15 bases or more which is positioned at the 3' side of position 34 of SEQ ID NO: 88 or 89.

Restriction Enzyme:

A restriction enzyme for the primer set based on SEQ ID NO: 86 includes MseI, a restriction enzyme for the primer set based on SEQ ID NO: 128 includes NlaIII, and a restriction enzyme for the primer set based on SEQ ID NO: 129 includes Tsp45I.

In one embodiment, the genetic feature (H) of the present invention can be detected, for example, by dCAPS method using the following primer set and a restriction enzyme.

Primer Set:

A primer set comprising a forward primer comprising a continuous sequence of 15 to 39-base long from the 3' end of the sequence selected from SEQ ID NOs: 137, 146, 147 and 148 and a reverse primer comprising a sequence (e.g., SEQ ID NO: 138) complementary to any continuous sequence of 15 bases or more which is positioned at the 3' side of position 41 of SEQ ID NO: 130 or 133.

Restriction Enzyme:

A restriction enzyme for the primer set based on SEQ ID NO: 137 includes EcoRV, a restriction enzyme for the primer set based on SEQ ID NO: 146 includes BaeI, a restriction enzyme for the primer set based on SEQ ID NO: 147 includes BclI, Ksp22I or FbaI, and a restriction enzyme for the primer set based on SEQ ID NO: 148 includes HindI, HincII, MjaIV or Hpy166II.

The sequences of the primers can be optimized within a range that satisfies the conditions described above. For the optimization of primer design, see, for example, Sambrook and Russell, "Molecular Cloning: A Laboratory Manual" 3rd Edition (2001), Cold Spring Harbor Laboratory Press. Each of the primers may be 15 to 50-base long, 18 to 48-base long, 20 to 45-base long, 30 to 40-base long, or the like. The restriction enzyme for each primer set also includes other enzymes that recognize the same sequence and cleave the same site as in the above enzyme, or an isoschizomer of the above enzyme. It is also possible to design a primer set other than those described above on the basis of the genetic feature(s) of the present invention and select a restriction enzyme appropriate therefor.

In a specific embodiment, the genetic features (A) to (G) of the present invention can be detected, e.g., by dCAPS method using the primer set having the following sequence and restriction enzyme

TABLE 1

Examples of combination of primer set and restriction enzyme for detecting genetic feature (A)

| Forward primer | Reverse primer | Restriction enzyme |
|---|---|---|
| SEQ ID NO: 50 | SEQ ID NO: 51 | RsaI |
| SEQ ID NO: 113 | SEQ ID NO: 117 | Tsp45I |
| SEQ ID NO: 114 | SEQ ID NO: 117 | AciI |

TABLE 2

Examples of combination of primer set and restriction enzyme for detecting genetic feature (B)

| Forward primer | Reverse primer | Restriction enzyme |
|---|---|---|
| SEQ ID NO: 56 | SEQ ID NO: 57 | AdlI |
| SEQ ID NO: 118 | SEQ ID NO: 57 | AluI |
| SEQ ID NO: 119 | SEQ ID NO: 57 | PacI |

TABLE 3

Examples of combination of primer set and restriction enzyme for detecting genetic feature (C)

| Forward primer | Reverse primer | Restriction enzyme |
|---|---|---|
| SEQ ID NO: 62 | SEQ ID NO: 63 | AluI |
| SEQ ID NO: 120 | SEQ ID NO: 63 | BglI |
| SEQ ID NO: 121 | SEQ ID NO: 63 | SeaI |

TABLE 4

Examples of combination of primer set and restriction enzyme for detecting genetic feature (D)

| Forward primer | Reverse primer | Restriction enzyme |
|---|---|---|
| SEQ ID NO: 68 | SEQ ID NO: 69 | AluI |
| SEQ ID NO: 122 | SEQ ID NO: 69 | MboI |
| SEQ ID NO: 123 | SEQ ID NO: 69 | BglII |

TABLE 5

Examples of combination of primer set and restriction enzyme for detecting genetic feature (E)

| Forward primer | Reverse primer | Restriction enzyme |
|---|---|---|
| SEQ ID NO: 74 | SEQ ID NO: 75 | AluI |
| SEQ ID NO: 124 | SEQ ID NO: 75 | MboI |
| SEQ ID NO: 125 | SEQ ID NO: 75 | BglII |

TABLE 6

Examples of combination of primer set and restriction enzyme for detecting genetic feature (F)

| Forward primer | Reverse primer | Restriction enzyme |
|---|---|---|
| SEQ ID NO: 80 | SEQ ID NO: 81 | RsaI |
| SEQ ID NO: 80 | SEQ ID NO: 126 | SnaI |
| SEQ ID NO: 80 | SEQ ID NO: 127 | AluI |

TABLE 7

Examples of combination of primer set and restriction enzyme for detecting genetic feature (G)

| Forward primer | Reverse primer | Restriction enzyme |
|---|---|---|
| SEQ ID NO: 86 | SEQ ID NO: 87 | MseI |
| SEQ ID NO: 128 | SEQ ID NO: 87 | NlaIII |
| SEQ ID NO: 129 | SEQ ID NO: 87 | Tsp45I |

In a specific embodiment, the genetic feature (H) of the present invention can be detected, e.g., by dCAPS method using the primer set having the following sequence and restriction enzyme.

TABLE 8

Examples of combination of primer set and restriction enzyme for detecting genetic feature (H)

| Forward primer | Reverse primer | Restriction enzyme |
|---|---|---|
| SEQ ID NO: 137 | SEQ ID NO: 138 | EcoRV |
| SEQ ID NO: 146 | SEQ ID NO: 138 | BaeI |
| SEQ ID NO: 147 | SEQ ID NO: 138 | BclI/Ksp22I/FbaI |
| SEQ ID NO: 148 | SEQ ID NO: 138 | HindII/HincII/ MjaIV/Hpy166II |

The combinations of the primer set and the restriction enzyme described above are mere examples, and other combinations of primer sets and restriction enzymes capable of detecting the genetic feature(s) of the present invention can be found by those skilled in the art.

The screening methods A to B of the present invention may further comprise a step of determining the content of RebD, RebM and/or RebN of a tissue (e.g., a leave) of the test *Stevia* plant tissue for which at least one of the genetic features (A) to (H) of the present invention have been detected. The determination of the content of RebD, RebM and/or RebN is as described in the section relating to the plant of the present invention. In this embodiment, the screening methods A to B of the present invention may be applied to daughter plants obtained by selecting individuals with a higher content of RebD from among the test *Stevia* plants in which at least one of the genetic features (A) to (H) of the present invention is/are detected, and crossing the selected individuals with another *Stevia* plants. Thus, the screening methods A to B of the present invention may comprise one or more of the following steps.

(i) Detecting at least one of the genetic features (A) to (H) of the present invention from the genome of a test *Stevia* plant;

(ii) determining the content of RebD, RebM and/or RebN of the test *Stevia* plant tissue in which at least one of the genetic features (A) to (H) of the present invention has/have been detected;

(iii) selecting an individual with a higher content of RebD, RebM and/or RebN from among the test *Stevia* plants in which at least one of the genetic features (A) to (H) of the present invention has/have been detected;

(iv) crossing the selected individual with a higher content of RebD, RebM and/or RebN with another *Stevia* plant;

(v) detecting at least one of the genetic features (A) to (H) of the present invention from the genome of daughter plants obtained by crossing, (vi) measuring the content of RebD, RebM and/or RebN of the tissue of the daughter plants in which at least one of the genetic features (A) to (H) of the present invention has/have been detected, (vii) selecting individuals having a higher content of RebD, RebM and/or RebN from among the daughter plants in which at least one of the genetic feature (A) to (H) are detected.

Individuals with a high content of RebD, RebM and/or RebN of choice may be, for example, up to 50%, up to 40%, up to 30%, up to 20%, up to 10%, up to 5%, up to 4%, up to 3%, up to 2%, or up to 1% of the test *Stevia* plants in which at least one of the genetic features (A) to (H) of the present invention has/have been detected, with respect to the high content of RebD, RebM and/or RebN. Other *Stevia* plants to be crossed may or may not contain the genetic features (A) to (H) of the present invention. In the above embodiment, steps (iv) to (vii) can be repeated a plurality of times. In this way, *Stevia* plants with a higher content of RebD, RebM and/or RebN can be screened.

In the screening methods A to B of the present invention, the test *Stevia* plant may be a natural plant or a non-genetically modified plant. Non-genetically modified plants are as described in the section relating to the plant of the present invention.

In the screening methods A to B of the present invention, the test *Stevia* plant may include a *Stevia* plant subjected to a mutagenesis treatment and a progeny plant thereof. The induction of a variation is as described in the section relating to the plant of the present invention, and includes treatment with a mutagen, treatment with radiation or irradiation with light, and the like.

The present invention also provides the primer sets described above and combinations thereof, for example, the primer sets described above in Tables 1 to 8 and combinations of these primer sets (e.g., a combination of at least one each of the primer sets described in Tables 1 to 8, such as a combination of the primer set of the forward primer comprising SEQ ID NO: 50 and the reverse primer comprising SEQ ID NO: 51 described in Table 1, and the primer set of the forward primer comprising SEQ ID NO: 80 and the reverse primer comprising SEQ ID NO: 81 described in Table 6). The present invention further provides a primer set capable of amplifying a region having a nucleotide sequence selected from the group consisting of SEQ ID NOs: 1 to 7, 22, 26, 30, 34, 38, 42, 46, 130 and 133 by PCR, for example, a primer set with a forward primer comprising a nucleotide sequence of SEQ ID NO: 8, and a reverse primer comprising a nucleotide sequence of SEQ ID NO: 9; a primer set with a forward primer comprising a nucleotide sequence of SEQ ID NO: 10, and a reverse primer comprising a nucleotide sequence of SEQ ID NO: 11; a primer set with a forward primer comprising a nucleotide sequence of SEQ ID NO: 12, and a reverse primer comprising a nucleotide sequence of SEQ ID NO: 13; a primer set with a forward primer comprising a nucleotide sequence of SEQ ID NO: 14, and a reverse primer comprising a nucleotide sequence of SEQ ID NO: 15; a primer set with a forward primer comprising a nucleotide sequence of SEQ ID NO: 16, and a reverse primer comprising a nucleotide sequence of SEQ ID NO: 17; a primer set with a forward primer comprising a nucleotide sequence of SEQ ID NO: 18, and a reverse primer comprising a nucleotide sequence of SEQ ID NO: 19; a primer set with a forward primer comprising a nucleotide sequence of SEQ ID NO: 20, and a reverse primer comprising a nucleotide sequence of SEQ ID NO: 21; a primer set with a forward primer comprising a nucleotide sequence of SEQ ID NO: 131, and a reverse primer comprising a nucleotide sequence of SEQ ID NO: 132; and the like.

In addition, the present invention provides a probe capable of detecting the presence and/or absence of the genetic features of the present invention, which may be referred to as the "probe of the present invention" hereinafter. The probe of the present invention may have a structure suitable for various detection methods (e.g., realtime PCR method such as TaqMan PCR method and the like) for the presence and/or absence of the genetic feature(s) of the present invention. For example, the probe of the present invention may comprise a nucleotide sequence complementary to a portion of a genome comprising a variation site of the present invention. Non-limiting examples of such probes include those comprising a sequence complementary to a nucleotide sequence selected from SEQ ID NOs: 23 to 25, 27 to 29, 31 to 33, 35 to 37, 39 to 41, 43 to 45, 47 to 49, 92 to 112. Of these sequences, SEQ ID NOs: 23 to 25, 27 to 29, 31 to 33, 35 to 37, 39 to 41, 43 to 45, 47 to 49 are specific for alleles comprising the variation of the present invention, and SEQ ID NOs: 92 to 112 are specific for alleles not containing the variation of the present invention. Further, SEQ ID NOs: 23 to 25 are specific for allele a, SEQ ID NOs: 27 to 29 are specific for allele b, SEQ ID NOs: 31 to 33 are specific for allele c, SEQ ID NOs: 35 to 37 are specific for allele d, SEQ ID NOs: 39 to 41 are specific for allele e, SEQ ID NOs: 43 to 45 are specific for allele f, SEQ ID NOs: 47 to 49 are specific for allele g. On the other hand, SEQ ID NOs: 92 to 94 are specific for allele A, SEQ ID NOs: 95 to 97 are specific for allele B, SEQ ID NOs: 98 to 100 are specific for allele C, SEQ ID NOs: 101 to 103 are specific for allele D, SEQ ID NOs: 104 to 106 are specific for allele E, SEQ ID NOs: 107 to 109 are specific for allele F, and SEQ ID NOs: 110 to 112 are specific for allele G. The presence of the genetic feature(s) of the present invention may be detected by detection of both of an allele comprising the variation of the present invention and an allele not comprising the variation of the present invention, and the absence of the genetic feature(s) of the present invention by detection of only an allele comprising the variation of the present invention or by detection of only an allele not comprising the variation of the present invention. The probes of the present invention preferably have a label. Non-limiting examples of such labels include fluorescent labels, luminescent labels, radioactive labels, dyes, enzymes, quenchers, binding moieties with detectable labels, and the like. In a specific embodiment, the probe of the present invention has a polynucleotide comprising a nucleotide sequence complementary to a nucleotide sequence selected from SEQ ID NOs: 23 to 25, 27 to 29, 31 to 33, 35 to 37, 39 to 41, 43 to 45, 47 to 49, 92 to 112 and a label.

Furthermore, the present invention provides a probe capable of detecting the presence and/or absence of the genetic feature (H) of the present invention, which may be referred to as the "probe (H) of the present invention" hereinafter. The probe (H) of the present invention may have a structure suitable for various detection methods (e.g., realtime PCR method such as TaqMan PCR method and the like) for the presence and/or absence of the genetic feature (H) of the present invention. For example, the probe (H) of the present invention may comprise a nucleotide sequence complementary to a portion of a genome comprising a variation site (H) of the present invention. Non-limiting examples of such probes include those comprising a sequence complementary to a nucleotide sequence selected from SEQ ID NOs: 134 to 136 and 143 to 145. Of these sequences, SEQ ID NOs: are specific for alleles comprising the variation (H) of the present invention, and SEQ ID NOs: 143 to 145 are specific for alleles not containing the variation (H) of the present invention. Further, included are those comprising a sequence complementary to the nucleotide sequence selected from SEQ ID NOs: 134 to 136 and 143 to 145. These are specific for allele h, and SEQ ID NOs: 143 to 145 are specific for allele H. The presence of the genetic feature (H) of the present invention may be detected by detection of both of an allele comprising the variation (H) of the present invention and an allele not comprising the variation (H) of the present invention, and the absence of the genetic feature (H) of the present invention by detection of only an allele comprising the variation (H) of the present invention or by detection of only an allele not comprising the variation (H) of the present invention. The probe (H) of the present invention preferably have a label. In a specific embodiment, the probe of the present invention has a polynucleotide comprising a nucleotide sequence complementary to a nucleotide sequence selected from SEQ ID NOs: 134 to 136 and 143 to 145, and a label.

The present invention further provides a kit comprising the above-mentioned primer set and a restriction enzyme appropriate therefor. In a specific embodiment, the kit of the present invention comprises a primer set stated in the above Tables 1-7 and a restriction enzyme appropriate therefor. The present invention also provides a kit comprising a primer set capable of amplifying by PCR a region having a nucleotide sequence selected from the group consisting of SEQ ID NOs: 1 to 7, 22, 26, 30, 34, 38, 42, 46, 130 and 133, and the above-mentioned probe of the present invention appropriate therefor.

These primer sets, probes and kits can be used to detect the genetic features (A) to (H) of the present invention, used in the screening methods A to B of the present invention, and the like. These primer sets and kits may also comprise an instruction including an explanation on the detection of genetic features (A) to (H) of the present invention and on the screening methods A to B of the present invention, e.g., a written instruction, information of a site comprising information regarding the method of use (e.g., URL and 2D code), and media, e.g., a flexible disk, a CD, a DVD, a Blu-ray disk, a memory card, a USB memory, etc., having recorded thereon information regarding the method of use, and the like.

In some embodiments, the present invention provides a screening kit for the *Stevia* plant of the present invention, comprising a reagent for detecting the presence and/or the absence of at least one of the genetic features (A) to (G). The reagent may comprise a primer and/or a probe for use in CAPS method, dCAPS method or TaqManPCR method. In a specific embodiment, the reagent for detecting the presence and/or the absence of at least one of the genetic features (A) to (G) comprises a combination of a primer set and a restriction enzyme for detecting at least one of the above genetic features (A) to (G) by the dCAPS method, for instance a combination of a primer set and a restriction enzyme stated in Tables 1-7, or a combination of a primer set that amplifies the variation site(s) of the present invention (e.g., a site comprising a sequence selected from SEQ ID NOs: 22 to 49), and a probe having a nucleotide sequence complementary to a site related to at least one of the genetic features (A) to (G) (e.g., a site comprising a sequence selected from SEQ ID NOs: 23 to 25, 27 to 29, 31 to 33, 35 to 37, 39 to 41, 43 to 45, and 47 to 49), which can be used in the TaqMan PCR method or the like.

In another embodiment, the present invention provides a screening kit for the *Stevia* plant D or E of the present invention, comprising a reagent for detecting the presence and/or the absence of the genetic feature (H). The reagent may comprise a primer and/or a probe for use in CAPS method, dCAPS method or TaqMan PCR method. In a specific embodiment, the reagent for detecting the presence and/or the absence of the genetic feature (H) comprises a combination of a primer set and a restriction enzyme for detecting at least one of the above genetic feature (H) by the dCAPS method, for instance a combination of a primer set and a restriction enzyme stated in Table 8, or a combination of a primer set that amplifies the variation site (H) of the present invention (e.g., a site comprising a sequence selected from SEQ ID NOs: 133 to 136), and a probe having a nucleotide sequence complementary to a site related to the genetic feature (H) (e.g., a site comprising a sequence selected from SEQ ID NOs: 133 to 136), which can be used in the TaqMan PCR method or the like.

4. Method of Producing Extract Derived from Plant and Product Comprising the Extract In a further aspect, the present invention provides a method of producing an extract containing RebD, RebM and/or RebN, comprising a step of obtaining an extract from the plant of the present invention, a *Stevia* plant selected by the screening method A of the present invention or a *Stevia* plant produced by the production method A of the present invention, or a seed, a leaf (e.g., dried leaf or fresh leaf), a tissue, a tissue culture or a cell of the plant (hereinafter, may be referred to as the "extract production method A of the present invention").

Further provided is an extract containing RebD, RebM and/or RebN from the plant of the present invention, a *Stevia* plant selected by the screening method A of the present invention or a *Stevia* plant produced by the production method A of the present invention, or a seed, a leaf (e.g., dried leaf or fresh leaf), a tissue, a tissue culture or a cell of the plant (hereinafter, may be referred to as the "extract A of the present invention"). The extract A of the present invention is preferably produced by the extract production method A of the present invention. Furthermore provided is a method of producing RebD, RebM and/or RebN, comprising a step of purifying RebD, RebM and/or RebN from the extract A of the present invention (hereinafter, may be referred to as the "steviol glycoside production method A of the present invention"). The steviol glycoside production method A of the present invention may further comprise a step of obtaining an extract comprising RebD, RebM and/or RebN from the plant of the present invention, a *Stevia* plant selected by the screening method A of the present invention or a *Stevia* plant produced by the production method A of the present invention.

In a further aspect, the present invention provides a method of producing an extract containing RebD, RebM and/or RebN, comprising a step of obtaining an extract from the plants D to E of the present invention, a *Stevia* plant selected by the screening method B of the present invention or a *Stevia* plant produced by the production method B of the present invention, or a seed or a leaf (e.g., dried leaf or fresh leaf) of the plant (hereinafter, may be referred to as the "extract production method B of the present invention").

Further provided is an extract containing RebD, RebM and/or RebN from the plants D to E of the present invention, a *Stevia* plant selected by the screening method B of the present invention or a *Stevia* plant produced by the production method B of the present invention, or a seed, a leaf (e.g., dried leaf or fresh leaf), a tissue, a tissue culture or a cell of the plant (hereinafter, may be referred to as the "extract B of the present invention"). The extract B of the present invention is preferably produced by the extract production method B of the present invention. Furthermore provided is a method of producing RebD, RebM and/or RebN, comprising a step of purifying RebD, RebM and/or RebN from the extract B of the present invention (hereinafter, may be referred to as the "steviol glycoside production method B of the present invention"). The steviol glycoside production method B of the present invention may further comprise a step of obtaining an extract comprising RebD, RebM and/or RebN from the plants D to E of the present invention, a *Stevia* plant selected by the screening method B of the present invention or a *Stevia* plant produced by the production method B of the present invention.

The extract containing RebD, RebM and/or RebN can be obtained by reacting a fresh leaf or a dried leaf of the plants A to E of the present invention with a suitable solvent (an aqueous solvent such as water or an organic solvent such as an alcohol, ether or acetone). For the extraction conditions, etc., see a method described in Ohta et al., supra or WO2010/038911, or a method described in Examples mentioned later.

RebD, RebM and/or RebN can be purified from the extract containing RebD, RebM, and/or RebN by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The extracts A to B of the present invention comprises RebD, RebM and/or RebN at higher content as compared with a *Stevia* species having none of the genetic features (A) to (H) of the present invention.

The extracts A to B of the present invention may comprise RebD, RebM and/or RebN at higher content by about 50% or more, about 100% or more, about 150% or more, about 200% or more, about 250% or more, about 300% or more, about 350% or more, about 400% or more, about 450% or more, about 500% or more, about 550% or more, about 600% or more, about 650% or more, about 700% or more, about 750% or more, about 800% or more, about 850% or more, about 900% or more, about 950% or more, about 1000% or more, about 1050% or more, about 1100% or more, about 1150% or more, about 1200% or more, about 1250% or more, about 1300% or more, about 1350% or more, about 1400% or more, about 1450% or more, about 1500% or more, about 1550% or more, about 1600% or more, about 1650% or more, about 1700% or more, about 1750% or more, about 1800% or more, about 1850% or more, about 1900% or more, about 1950% or more, about 2000% or more, about 2050% or more, about 2100% or more as compared with an extract obtained from a *Stevia* plant having none of the genetic features (A) to (H) of the present invention. The extracts A to B of the present invention and the extract obtained from the *Stevia* plant having none of the genetic features (A) to (H) of the present invention may be those obtained by the same process.

The extracts A to B of the present invention thus obtained and/or RebD, RebM and/or RebN obtained by the steviol glycoside production methods A to B of the present invention can be mixed with other component(s) to produce a novel food or beverage, sweetener composition, flavor or medicament with increased content of RebD, RebM and/or RebN. Accordingly, in an alternative aspect, the present invention provides a method of producing a food or beverage, a sweetener composition, a flavor or a medicament, comprising a step of mixing the extracts A to B of the present invention, and/or RebD, RebM and/or RebN obtained by the steviol glycoside production methods A to B of the present invention with other component(s). The present invention further provides a novel food or beverage, sweetener composition, flavor or medicament with increased content of RebD, RebM and/or RebN, obtained by the production method. In this context, the food or beverage comprises a beverage and a food. Thus, in a certain embodiment, the present invention provides a novel beverage, food, sweetener composition, flavor or medicament and also provides a method of producing the beverage, food, sweetener composition, flavor or medicament.

5. Nucleotide Sequence Relating to Plant of Present Invention

In another aspect, the present invention provides nucleotide sequences relating to the plant of the present invention.

Nucleotide sequences relating to a *Stevia* plant having the genetic feature (A) comprise or consist of a nucleotide sequence selected from SEQ ID NOs: 22 to 25. Nucleotide sequences relating to a *Stevia* plant having the genetic feature (B) comprise or consist of a nucleotide sequence selected from SEQ ID NOs: 26 to 29. Nucleotide sequences relating to a *Stevia* plant having the genetic feature (C) comprise or consist of a nucleotide sequence selected from SEQ ID NOs: 30 to 33. Nucleotide sequences relating to a *Stevia* plant having the genetic feature (D) comprise or consist of a nucleotide sequence selected from SEQ ID NOs: 34 to 37. Nucleotide sequences relating to a *Stevia* plant having the genetic feature (E) comprise or consist of a nucleotide sequence selected from SEQ ID NOs: 38 to 41. Nucleotide sequences relating to a *Stevia* plant having the genetic feature (F) comprise or consist of a nucleotide sequence selected from SEQ ID NOs: 42 to 45. Nucleotide sequences relating to a *Stevia* plant having the genetic feature (G) comprise or consist of a nucleotide sequence selected from SEQ ID NOs: 46 to 49. Nucleotide sequences relating to a *Stevia* plant having the genetic feature (H) comprise or consist of a nucleotide sequence selected from SEQ ID NOs: 133 to 136.

EXAMPLES

Hereinafter, the present invention will be described with reference to Examples, etc. However, the present invention is not limited by these specific embodiments.

[Example 1] Preparation of *Stevia* Plant with High RebD Content

1. Production of Test Lines

A wild type *Stevia* species (commercially available variety) was treated with ethyl methanesulfonate (EMS), and the resultant was seeded and cultivated in a greenhouse within the Suntory World Research Center. An appropriate amount of fresh leaves was sampled from each grown individual, and the concentration of RebD was quantitatively determined by LC-MS/MS (Shimadzu LCMS8050). Specifically, 0.25 g of the fresh leaves was dried by freeze drying, and 0.05 g of homogenized dry matter thereof was added into a 100-fold amount (5 mL) of pure water. Extraction by ultrasonic treatment for 20 minutes, and centrifugation and filtration were performed, followed by 60-fold dilution with 32% acetonitrile to obtain a liquid sample. The concentration of RebD was quantitatively determined by LC/MS-MS analysis on this 1 mL of liquid sample in a LCMS8050 MRM mode, and individuals having the concentration of 2% or more were selected and crossed to obtain seeds. Such selection was repeated over four generations to obtain the fourth filial generation (S4 generation).

2. Measurement of Steviol Glycoside Contained in Each Individual

An appropriate amount of fresh leaves was sampled from individuals of a plurality of S4 generation lines obtained as described above. The concentrations (% by mass with respect to a dried leaf) of RebA, RebB, RebC, RebD, RebE, RebF, RebG, RebM, RebN and stevioside (STV) were quantitatively determined by LC/MS-MS analysis in the same way as in the preceding section 1, and the total sum thereof was regarded as the concentration of total steviol glycoside (TSG). The results are shown in the table below.

TABLE 9

Glycoside concentration in S4 generation lines

| Line number | RebA | RebB | RebC | RebD | STV | RebF | RebM | RebN | RebE | RebG | TSG |
|---|---|---|---|---|---|---|---|---|---|---|---|
| S4-1 | 7.01 | 0.20 | 0.70 | 6.28 | 1.32 | 0.24 | 1.53 | 1.11 | 0.52 | 0.01 | 18.91 |
| S4-2 | 5.14 | 0.08 | 0.34 | 5.74 | 0.49 | 0.19 | 1.08 | 0.89 | 0.50 | 0.00 | 14.45 |
| S4-3 | 4.62 | 0.10 | 0.39 | 5.50 | 0.48 | 0.16 | 1.60 | 1.11 | 0.39 | 0.00 | 14.35 |
| S4-4 | 3.93 | 0.07 | 0.40 | 5.23 | 0.60 | 0.15 | 1.23 | 1.23 | 0.43 | 0.00 | 13.28 |
| S4-5 | 4.79 | 0.13 | 0.54 | 4.83 | 1.36 | 0.19 | 1.58 | 1.18 | 0.37 | 0.01 | 14.99 |
| S4-6 | 6.60 | 0.13 | 0.52 | 4.76 | 0.43 | 0.22 | 1.73 | 1.10 | 0.20 | 0.01 | 15.70 |
| S4-7 | 6.68 | 0.14 | 0.50 | 4.49 | 1.29 | 0.21 | 0.98 | 0.87 | 0.42 | 0.01 | 15.59 |
| S4-8 | 6.74 | 0.12 | 0.40 | 4.47 | 1.00 | 0.23 | 0.98 | 0.53 | 0.27 | 0.01 | 14.75 |
| S4-9 | 5.49 | 0.15 | 0.43 | 4.36 | 5.46 | 0.22 | 0.66 | 0.63 | — | — | 17.40 |
| S4-10 | 7.71 | 0.14 | 0.60 | 4.36 | 0.56 | 0.27 | 1.54 | 0.91 | 0.20 | 0.01 | 16.29 |
| S4-11 | 4.88 | 0.17 | 0.42 | 4.35 | 1.29 | 0.20 | 1.12 | 0.78 | 0.33 | 0.01 | 13.55 |
| S4-12 | 4.07 | 0.07 | 0.32 | 4.31 | 0.59 | 0.16 | 1.29 | 0.87 | 0.41 | 0.00 | 12.08 |
| S4-13 | 6.49 | 0.16 | 0.48 | 3.72 | 0.95 | 0.22 | 1.31 | 0.81 | 0.21 | 0.01 | 14.37 |
| S4-14 | 5.82 | 0.14 | 0.48 | 3.65 | 0.98 | 0.21 | 1.26 | 0.65 | 0.20 | 0.01 | 13.41 |
| S4-15 | 4.45 | 0.10 | 0.39 | 3.62 | 0.80 | 0.16 | 1.21 | 0.94 | 0.26 | 0.00 | 11.93 |
| S4-16 | 3.60 | 0.06 | 0.33 | 3.56 | 0.24 | 0.14 | 1.08 | 1.06 | 0.27 | 0.01 | 10.35 |
| S4-17 | 5.97 | 0.11 | 0.48 | 3.55 | 0.75 | 0.20 | 1.18 | 0.92 | 0.27 | 0.01 | 13.43 |
| S4-18 | 5.86 | 0.09 | 0.42 | 3.51 | 0.96 | 0.20 | 1.20 | 0.59 | 0.22 | 0.01 | 13.07 |
| S4-19 | 9.05 | 0.11 | 0.52 | 1.55 | 0.46 | 0.26 | 1.09 | 0.19 | 0.02 | 0.02 | 13.27 |
| S4-20 | 4.94 | 0.06 | 0.19 | 1.52 | 0.33 | 0.14 | 1.14 | 0.21 | — | — | 8.55 |
| S4-21 | 4.23 | 0.03 | 0.16 | 1.44 | 0.18 | 0.13 | 1.22 | 0.24 | — | — | 7.64 |
| S4-22 | 4.26 | 0.09 | 0.21 | 1.32 | 0.27 | 0.11 | 1.35 | 0.13 | — | — | 7.73 |
| S4-23 | 8.96 | 0.05 | 0.99 | 1.20 | 7.39 | 0.35 | 0.12 | 0.20 | — | — | 19.38 |
| S4-24 | 9.70 | 0.06 | 1.00 | 1.11 | 8.98 | 0.38 | 0.10 | 0.18 | — | — | 21.60 |
| S4-25 | 5.81 | 0.06 | 0.32 | 1.11 | 0.11 | 0.17 | 1.54 | 0.26 | 0.01 | 0.01 | 9.39 |
| S4-26 | 1.67 | 0.03 | 0.23 | 1.06 | 1.93 | 0.08 | 0.08 | 0.18 | — | — | 5.41 |
| S4-27 | 7.31 | 0.03 | 0.83 | 1.05 | 4.66 | 0.32 | 0.12 | 0.20 | — | — | 14.61 |
| S4-28 | 2.23 | 0.05 | 0.15 | 0.98 | 0.64 | 0.08 | 0.29 | 0.12 | — | — | 4.76 |
| S4-29 | 3.60 | 0.04 | 0.15 | 0.73 | 0.18 | 0.11 | 0.57 | 0.14 | — | — | 5.52 |

As shown in the results, high RebD-content lines having a RebD content exceeding 3.5% by mass based on a dried leaf were obtained (S4-1 to S4-18) by the selection of high RebD-content individuals.

[Example 2] Detection of Genetic Feature Unique to *Stevia* Plant with High RebD Content (1)

Genomic DNA was extracted from the fresh leaves of some individuals tested in Example 1, and analyzed for genetic features unique to *Stevia* plants with high RebD content using a sequencer (HiSeq 2500, Illumina, Inc.). As a result, genetic features (A) to (G) tended to be detected in the lines with high RebD content. Then, in order to efficiently detect the genetic features, dCAPS primers for detecting the genetic features (A), (F) and (G) were generated, and the remaining individuals were evaluated for the presence or absence of these genetic features by the dCAPS method. The study by the dCAPS method was omitted for the genetic features (B) to (E), because their variation sites were positioned close to that of the genetic feature (A) on the genome and were likely to be in linkage disequilibrium.

The following dCAPS primers and restriction enzymes were used.

TABLE 10

Sequence of dCAPS primers and restriction enzyme

| Genetic feature | Forward primer | Reverse primer | Restriction enzyme |
|---|---|---|---|
| (A) | AATTATATGATAGAAATTGTTTTCACATTTTGTGTGCCG (SEQ ID NO: 50) | TGGACTAGCGCATATAGGTTAAAGTA (SEQ ID NO: 51) | RsaI |
| (F) | GGCAGCCATTGATGATGTTGTTGAA (SEQ ID NO: 80) | CCAATTCTCATAGAAAATATGATAGAATAAATGCGT (SEQ ID NO: 81) | RsaI |
| (G) | TGATTTTGAAAGGATCTGACTGTATGTTTTTA (SEQ ID NO: 86) | TGTTGACCATCAAGCCACAT (SEQ ID NO: 87) | MseI |

TABLE 11

Possession of genetic feature by lines of S4 generation

| Line number | Genetic feature (A) | Genetic feature (F) | Genetic feature (G) |
|---|---|---|---|
| S4-1 | ○ | ○ | ○ |
| S4-2 | ○ | ○ | ○ |
| S4-3 | ○ | ○ | ○ |
| S4-4 | ○ | ○ | ○ |
| S4-5 | ○ | ○ | ○ |
| S4-6 | ○ | ○ | ○ |
| S4-7 | ○ | ○ | ○ |
| S4-8 | ○ | ○ | ○ |
| S4-9 | ○ | ○ | ○ |
| S4-10 | ○ | ○ | ○ |
| S4-11 | ○ | ○ | ○ |
| S4-12 | ○ | ○ | ○ |
| S4-13 | ○ | ○ | ○ |
| S4-14 | ○ | ○ | ○ |
| S4-15 | ○ | ○ | ○ |
| S4-16 | ○ | ○ | ○ |
| S4-17 | ○ | ○ | ○ |
| S4-18 | ○ | ○ | ○ |
| S4-19 | x | x | x |
| S4-20 | x | x | x |
| S4-21 | x | x | x |

The detection of each genetic feature by the dCAPS method was performed as follows. First, genomic DNA was extracted from the fresh leaves of each individual tested in Example 1, and PCR was performed using the above dCAPS primers for each genetic feature. The above restriction enzyme for each genetic feature was added to the PCR product, and enzymatic reaction was performed at 37° C. The restriction enzyme-treated products were electrophoresed using a microchip type electrophoresis apparatus LabChip GX Touch HT (PerkinElmer, Inc.). The presence or absence of the genetic feature was determined on the basis of the obtained band pattern. Specifically, since all the genetic features (A), (F) and (G) are of being heterozygous, an individual for which both the bands of a degraded product and a non-degraded product were found was determined as having the genetic feature (indicated by a circle), and an individual for which only any one of the degraded product and the non-degraded product was found was determined as having no genetic feature (indicated by a x-mark).

As shown in the table below, all the lines with high RebD content had the genetic features (A), (F) and (G). On the other hand, the lines having a RebD content of less than 1.6% had none of the genetic features (A), (F) and (G).

TABLE 11-continued

Possession of genetic feature by lines of S4 generation

| Line number | Genetic feature (A) | Genetic feature (F) | Genetic feature (G) |
|---|---|---|---|
| S4-22 | x | x | x |
| S4-23 | x | x | x |
| S4-24 | x | x | x |
| S4-25 | x | x | x |
| S4-26 | x | x | x |
| S4-27 | x | x | x |
| S4-28 | x | x | x |
| S4-29 | x | x | x |

As is evident from the above results, the lines having the genetic feature(s) of the present invention not only had a high RebD content (approximately 4.46% on average, up to 6.28%) but tended to also have a high total content of RebD and RebM (approximately 5.71% on average, up to 7.81%), mass ratio of RebD to TSG (approximately 31.28% on average, up to 39.70%), total mass ratio of RebD and RebM to TSG (approximately 40.15% on average, up to 49.47%), RebN content (approximately 0.90% on average, up to 1.23%), total content of RebD and RebN (approximately 5.36% on average, up to 7.39%) and total content of RebD, RebM, and RebN (approximately 6.61% on average, up to 8.91%).

[Example 3] Detection of Genetic Feature Unique to *Stevia* Plant with High RebD Content (2)

Genomic DNA was extracted from the fresh leaves of individuals of lines of S4 generation other than those tested in Example 1, and analyzed for genetic features unique to *Stevia* plants with high RebD content using a sequencer (HiSeq 2500, Illumina, Inc.). As a result, genetic feature (H) tended to be detected in the lines with high RebD content. Then, in order to efficiently detect the genetic feature (H), dCAPS primers for detecting the genetic feature (H) were generated, and the remaining individuals were evaluated for the presence or absence of these genetic features by the dCAPS method. In addition, concentrations of steviol glycosides were quantitatively determined in a same manner as Example 1

The following dCAPS primers and restriction enzymes were used.

```
Forward primer:
                                    (SEQ ID NO: 137)
AATCAGTCCAATTTAAACGTGCTCTACTTACAGAGATAT

Reverse primer:
                                    (SEQ ID NO: 138)
CACTTCTCTTCATCAGAGTAACTCAATTC
```

Restriction Enzyme: EcoRV

The detection of each genetic feature by the dCAPS method was performed as follows. First, genomic DNA was extracted from the fresh leaves of each individual of the lines of S4 generation, and PCR was performed using the above dCAPS primers. The above restriction enzyme was added to the PCR product, and enzymatic reaction was performed at 37° C. The restriction enzyme-treated products were electrophoresed using a microchip type electrophoresis apparatus LabChip GX Touch HT (PerkinElmer, Inc.). The presence or absence of the genetic feature (H) was determined on the basis of the obtained band pattern. Specifically, since the genetic feature (H) is of being heterozygous, an individual for which both the bands of a degraded product and a non-degraded product were found was determined as having the genetic feature (H) (indicated by a circle), and an individual for which only any one of the degraded product and the non-degraded product was found was determined as having no genetic feature (H) (indicated by a x-mark). In addition, the presence or absence of the genetic features (A) and (F) was also evaluated for the same individual in the same manner as Example 2.

As shown in Tables 12 to 13, all the individuals having the genetic feature (H) had also the genetic features (A) and (F), but some individuals with a low total content of RebD and RebM had the genetic features (A) and (F), but not the genetic feature (H). From these results, it was found that by selecting individuals having the genetic feature (H), some individuals with a low total content of RebD and RebM were excluded from individuals having the genetic features (A) and (F), and a population with a higher average total content of RebD and RebM was obtained (see Table 14). Further, regarding steviol glycoside properties relating to other chemical features (i.e., RebD content, mass ratio of RebD to TSG, total mass ratio of RebD and RebM to TSG, Reb N content, total content of RebD and RebN, and total content of RebD, RebM, and RebN), a population having the genetic feature (H) was superior to a population having the genetic features (A) and (F).

TABLE 12

Glycoside concentration in S4 generation lines

| Line number | RebA | RebB | RebC | RebD | STV | RebF | RebM | RebN | RebE | RebI | RebJ | TSG |
|---|---|---|---|---|---|---|---|---|---|---|---|---|
| S4A-1 | 5.16 | 0.10 | 0.33 | 2.09 | 2.49 | 0.18 | 0.38 | 0.32 | 0.27 | 0.03 | 0.20 | 11.54 |
| S4A-2 | 4.69 | 0.09 | 0.36 | 2.01 | 2.17 | 0.18 | 0.45 | 0.37 | 0.22 | 0.03 | 0.21 | 10.77 |
| S4A-3 | 5.06 | 0.12 | 0.41 | 1.95 | 3.31 | 0.19 | 0.41 | 0.38 | 0.31 | 0.03 | 0.22 | 12.40 |
| S4A-4 | 4.29 | 0.09 | 0.26 | 1.87 | 2.11 | 0.15 | 0.45 | 0.24 | 0.25 | 0.03 | 0.14 | 9.89 |
| S4A-5 | 3.74 | 0.07 | 0.28 | 1.91 | 2.32 | 0.14 | 0.39 | 0.28 | 0.29 | 0.02 | 0.19 | 9.63 |
| S4A-6 | 5.53 | 0.12 | 0.39 | 1.91 | 3.09 | 0.20 | 0.38 | 0.31 | 0.31 | 0.03 | 0.20 | 12.46 |
| S4A-7 | 4.22 | 0.08 | 0.27 | 1.87 | 2.00 | 0.14 | 0.37 | 0.29 | 0.27 | 0.02 | 0.17 | 9.71 |
| S4A-8 | 4.87 | 0.09 | 0.33 | 1.85 | 2.47 | 0.16 | 0.39 | 0.33 | 0.27 | 0.02 | 0.20 | 10.99 |
| S4A-9 | 5.38 | 0.11 | 0.41 | 1.81 | 3.45 | 0.17 | 0.36 | 0.33 | 0.31 | 0.03 | 0.22 | 12.60 |
| S4A-10 | 4.16 | 0.08 | 0.30 | 1.65 | 2.01 | 0.14 | 0.35 | 0.28 | 0.21 | 0.02 | 0.17 | 9.37 |
| S4A-11 | 3.91 | 0.09 | 0.26 | 1.50 | 2.78 | 0.14 | 0.30 | 0.20 | 0.24 | 0.02 | 0.13 | 9.57 |
| S4A-12 | 4.78 | 0.10 | 0.28 | 1.37 | 2.37 | 0.17 | 0.37 | 0.21 | 0.14 | 0.04 | 0.03 | 9.85 |
| S4A-13 | 5.06 | 0.09 | 0.34 | 1.42 | 2.50 | 0.15 | 0.28 | 0.30 | 0.22 | 0.04 | 0.04 | 10.45 |
| S4A-14 | 3.35 | 0.08 | 0.22 | 1.46 | 2.31 | 0.12 | 0.23 | 0.19 | 0.20 | 0.02 | 0.10 | 8.27 |
| S4A-15 | 3.90 | 0.08 | 0.30 | 1.41 | 2.73 | 0.13 | 0.26 | 0.27 | 0.21 | 0.03 | 0.05 | 9.37 |
| S4A-16 | 4.09 | 0.08 | 0.26 | 1.20 | 1.75 | 0.14 | 0.33 | 0.23 | 0.10 | 0.04 | 0.02 | 8.25 |
| S4A-17 | 3.84 | 0.10 | 0.28 | 1.28 | 2.56 | 0.14 | 0.25 | 0.24 | 0.20 | 0.02 | 0.03 | 8.95 |
| S4A-18 | 4.85 | 0.13 | 0.34 | 1.24 | 2.21 | 0.17 | 0.28 | 0.20 | 0.14 | 0.03 | 0.11 | 9.69 |
| S4A-19 | 3.75 | 0.08 | 0.25 | 1.21 | 2.80 | 0.14 | 0.28 | 0.23 | 0.16 | 0.03 | 0.03 | 8.96 |
| S4A-20 | 2.76 | 0.05 | 0.22 | 1.23 | 1.72 | 0.10 | 0.23 | 0.27 | 0.21 | 0.02 | 0.04 | 6.85 |
| S4A-21 | 3.00 | 0.07 | 0.25 | 1.25 | 2.34 | 0.11 | 0.18 | 0.20 | 0.23 | 0.01 | 0.14 | 7.80 |
| S4A-22 | 3.21 | 0.05 | 0.24 | 1.04 | 1.59 | 0.11 | 0.27 | 0.26 | 0.11 | 0.03 | 0.03 | 6.94 |
| S4A-23 | 4.53 | 0.09 | 0.20 | 0.71 | 0.59 | 0.12 | 0.48 | 0.11 | 0.02 | 0.07 | 0.05 | 6.95 |
| S4A-24 | 3.90 | 0.07 | 0.23 | 0.86 | 1.83 | 0.12 | 0.23 | 0.18 | 0.11 | 0.03 | 0.03 | 7.60 |
| S4A-25 | 2.92 | 0.06 | 0.20 | 0.82 | 1.91 | 0.10 | 0.19 | 0.16 | 0.10 | 0.02 | 0.02 | 6.50 |
| S4A-26 | 3.84 | 0.09 | 0.25 | 0.76 | 2.31 | 0.14 | 0.19 | 0.15 | 0.10 | 0.03 | 0.02 | 7.88 |
| S4A-27 | 4.65 | 0.08 | 0.27 | 0.61 | 0.72 | 0.13 | 0.31 | 0.14 | 0.02 | 0.06 | 0.05 | 7.03 |
| S4A-28 | 0.02 | 0.00 | 0.03 | 0.04 | 6.14 | 0.00 | 0.00 | 0.02 | 2.69 | 0.00 | 0.00 | 8.94 |

TABLE 13

| Possession of genetic feature by lines of S4 generation | | | |
|---|---|---|---|
| Line number | Genetic feature (A) | Genetic feature (F) | Genetic feature (H) |
| S4A-1 | ○ | ○ | ○ |
| S4A-2 | ○ | ○ | ○ |
| S4A-3 | ○ | ○ | ○ |
| S4A-4 | ○ | ○ | ○ |
| S4A-5 | ○ | ○ | ○ |
| S4A-6 | ○ | ○ | ○ |
| S4A-7 | ○ | ○ | ○ |
| S4A-8 | ○ | ○ | ○ |
| S4A-9 | ○ | ○ | ○ |
| S4A-10 | ○ | ○ | ○ |
| S4A-11 | ○ | ○ | ○ |
| S4A-12 | ○ | ○ | ○ |
| S4A-13 | ○ | ○ | ○ |
| S4A-14 | ○ | ○ | ○ |
| S4A-15 | ○ | ○ | ○ |
| S4A-16 | ○ | ○ | ○ |
| S4A-17 | ○ | ○ | ○ |
| S4A-18 | ○ | ○ | ○ |
| S4A-19 | ○ | ○ | x |
| S4A-20 | ○ | ○ | ○ |
| S4A-21 | ○ | ○ | ○ |
| S4A-22 | ○ | ○ | ○ |
| S4A-23 | ○ | ○ | x |
| S4A-24 | ○ | ○ | ○ |
| S4A-25 | ○ | ○ | ○ |
| S4A-26 | ○ | ○ | ○ |
| S4A-27 | ○ | ○ | x |
| S4A-28 | ○ | ○ | x |

TABLE 14

| Improvement of steviol glycoside properties in population having genetic feature (H) | | | |
|---|---|---|---|
| | Population with genetic features (A) and (F) | Population with geneticfeature (H) | Increase rate (%) |
| RebD | 1.37 | 1.49 | 8.88 |
| RebN | 0.24 | 0.26 | 8.08 |
| RebDM | 1.68 | 1.80 | 7.67 |
| RebDN | 1.61 | 1.75 | 8.76 |
| RebDMN | 1.92 | 2.06 | 7.72 |
| RebD/TSG | 0.15 | 0.16 | 7.30 |
| RebDM/TSG | 0.18 | 0.19 | 5.72 |

* RebDM indicates total content of RebD and RebM, RebDN indicates total content of RebD and RebN, RebDMN indicates total content of RebD, RebM and RebN, RebD/TSG indicates ratio of RebD content to TSG content, and RebDM/TSG indicates ratio of total content of RebD and RebM to TSG content.

INDUSTRIAL APPLICABILITY

The present invention enables the more efficient provision of useful steviol glycoside such as RebD and can therefore promote the provision of a food or beverage, a sweetener composition, a flavor or a medicament, etc. comprising such steviol glycoside and thereby having good quality of taste.

The invention claimed is:

1. A *stevia* plant having at least one of the following chemical features (1) to (7):

(1) the content of rebaudioside (Reb) D is 3.6% or more per unit mass of a dried leaf;

(2) the total content of RebD and RebM is 4.9% or more per unit mass of a dried leaf;

(3) the mass ratio of RebD to total steviol glycoside is 32.0% or more;

(4) the total mass ratio of RebD and RebM to total steviol glycoside is 38.2% or more;

(5) the content of RebN is 1.0% or more per unit mass of a dried leaf;

(6) the total content of RebD and RebN is 4.0% or more per unit mass of a dried leaf;

(7) the total content of RebD, RebM, and RebN is 4.9% or more per unit mass of a dried leaf; and having at least one of the following genetic features (A) to (H):

(A) heterozygous for the allele wherein the base at the position corresponding to position 40 of SEQ ID NO: 1 is C;

(B) heterozygous for the allele wherein the base at the position corresponding to position 21 of SEQ ID NO: 2 is T;

(C) heterozygous for the allele wherein the base at the position corresponding to position 28 of SEQ ID NO: 3 is T;

(D) heterozygous for the allele wherein the base at the position corresponding to position 59 of SEQ ID NO: 4 is C;

(E) heterozygous for the allele wherein the base at the position corresponding to position 64 of SEQ ID NO: 5 is T;

(F) heterozygous for the allele wherein the base at the position corresponding to position 290 of SEQ ID NO: 6 is C;

(G) heterozygous for the allele wherein the base at the position corresponding to position 33 of SEQ ID NO: 7 is T;

(H) heterozygous for the allele wherein the base at the position corresponding to position 40 of SEQ ID NO: 130 is C.

2. A *stevia* plant having at least one of the following genetic features (A) to (H):

(A) heterozygous for the allele wherein the base at the position corresponding to position 40 of SEQ ID NO: 1 is C;

(B) heterozygous for the allele wherein the base at the position corresponding to position 21 of SEQ ID NO: 2 is T;

(C) heterozygous for the allele wherein the base at the position corresponding to position 28 of SEQ ID NO: 3 is T;

(D) heterozygous for the allele wherein the base at the position corresponding to position 59 of SEQ ID NO: 4 is C;

(E) heterozygous for the allele wherein the base at the position corresponding to position 64 of SEQ ID NO: 5 is T;

(F) heterozygous for the allele wherein the base at the position corresponding to position 290 of SEQ ID NO: 6 is C;

(G) heterozygous for the allele wherein the base at the position corresponding to position 33 of SEQ ID NO: 7 is T;

(H) heterozygous for the allele wherein the base at the position corresponding to position 40 of SEQ ID NO: 130 is C.

3. The plant according to claim 1, wherein the plant is a non-genetically modified plant.

4. The plant according to claim 1, wherein the plant includes a *stevia* plant subjected to a mutagenesis treatment and a progeny plant thereof.

5. A seed, a tissue, a dried leaf, a tissue culture or a cell of the plant according to claim 1,
wherein the seed includes the genetic features (A)-(H).

6. The tissue, tissue culture or cell according to claim 5, which is selected from an embryo, a meristem cell, a pollen, a leaf, a root, a root apex, a petal, a protoplast, a leaf section and a callus,
wherein the embryo includes the genetic features (A)-(H).

7. A method of producing a *stevia* plant having at least one of the following chemical features (1) to (7), the method comprising crossing the plant according to claim 1 with a second *stevia* plant:
(1) the content of rebaudioside (Reb) D is 3.6% or more per unit mass of a dried leaf;
(2) the total content of RebD and RebM is 4.9% or more per unit mass of a dried leaf,
(3) the mass ratio of RebD to total steviol glycoside is 32.0% or more;
(4) the total mass ratio of RebD and RebM to total steviol glycoside is 38.2% or more;
(5) the content of RebN is 1.0% or more per unit mass of a dried leaf;
(6) the total content of RebD and RebN is 4.0% or more per unit mass of a dried leaf;
(7) the total content of RebD, RebM, and RebN is 4.9% or more per unit mass of a dried leaf.

8. The method according to claim 7, wherein the second plant is a plant having at least one of the following chemical features (1) to (7):
(1) the content of rebaudioside (Reb) D is 3.6% or more per unit mass of a dried leaf;
(2) the total content of RebD and RebM is 4.9% or more per unit mass of a dried leaf;
(3) the mass ratio of RebD to total steviol glycoside is 32.0% or more;
(4) the total mass ratio of RebD and RebM to total steviol glycoside is 38.2% or more;
(5) the content of RebN is 1.0% or more per unit mass of a dried leaf,
(6) the total content of RebD and RebN is 4.0% or more per unit mass of a dried leaf;
(7) the total content of RebD, RebM, and RebN is 4.9% or more per unit mass of a dried leaf.

9. An extract of the plant according to claim 1, or of a seed, tissue, dried leaf, tissue culture or cell of the plant, wherein the extract comprises at least one of RebD, RebM and RebN,
wherein the seed includes the genetic features (A)-(H).

10. A method of producing an extract comprising at least one of RebD, RebM and RebN, comprising:
providing the plant according to claim 1 or the seed, tissue, dried leaf, tissue culture or cell thereof; and
obtaining an extract from the plant, seed, tissue, dried leaf, tissue culture or cell,
wherein the seed includes the genetic features (A)-(H).

11. A method of producing RebD, RebM and/or RebN, comprising:
providing the plant according to claim 1 or the seed, tissue, dried leaf, tissue culture or cell thereof;
obtaining an extract from the plant, seed, tissue, dried leaf, tissue culture or cell; and
purifying at least one of RebD, RebM and RebN from the extract,
wherein the seed includes the genetic features (A)-(H).

12. A method of producing a food or beverage, a sweetener composition, a flavor or a medicament, comprising:
providing the plant according to claim 1 or the seed, tissue, dried leaf, tissue culture or cell thereof,
obtaining an extract from the plant, seed, tissue, dried leaf, tissue culture or cell; and
adding the extract to a raw material for the food or beverage, sweetener composition, flavor or medicament,
wherein the seed includes the genetic features (A)-(H).

13. A method of producing the *stevia* plant according to claim 1, comprising introducing at least one of the following variations (A) to (H):
(A) the variation from T to C at a position corresponding to position 40 of SEQ ID NO: 1;
(B) the variation from A to T at a position corresponding to position 21 of SEQ ID NO: 2;
(C) the variation from C to T at a position corresponding to position 28 of SEQ ID NO: 3;
(D) the variation from A to C at a position corresponding to position 59 of SEQ ID NO: 4;
(E) the variation from C to T at a position corresponding to position 64 of SEQ ID NO: 5;
(F) the variation from T to C at a position corresponding to position 290 of SEQ ID NO: 6;
(G) the variation from A to T at a position corresponding to position 33 of SEQ ID NO: 7;
(H) the variation from G to C at a position corresponding to position 40 of SEQ ID NO: 130.

14. A method of producing an extract comprising at least one of RebD, RebM and RebN, comprising:
providing the plant according to claim 2 or the seed, tissue, dried leaf, tissue culture or cell thereof; and
obtaining an extract from the plant, seed, tissue, dried leaf, tissue culture or cell,
wherein the seed includes the genetic features (A)-(H).

15. A method of producing RebD, RebM and/or RebN, comprising:
providing the plant according to claim 2 or the seed, tissue, dried leaf, tissue culture or cell thereof;
obtaining an extract from the plant, seed, tissue, dried leaf, tissue culture or cell; and
purifying at least one of RebD, RebM and RebN from the extract,
wherein the seed includes the genetic features (A)-(H).

16. A method of producing a food or beverage, a sweetener composition, a flavor or a medicament, comprising:
providing the plant according to claim 2 or the seed, tissue, dried leaf, tissue culture or cell thereof;
obtaining an extract from the plant, seed, tissue, dried leaf, tissue culture or cell; and
adding the extract to a raw material for the food or beverage, sweetener composition, flavor or medicament,
wherein the seed includes the genetic features (A)-(H).

17. A method of producing a food or beverage, a sweetener composition, a flavor or a medicament, comprising:
providing the plant according to claim 1 or the seed, tissue, dried leaf, tissue culture or cell thereof;
obtaining an extract from the plant, seed, tissue, dried leaf, tissue culture or cell;
purifying at least one of RebD, RebM and RebN from the extract; and adding the at least one of RebD, RebM and RebN to a raw material for the food or beverage, sweetener composition, flavor or medicament, wherein the seed includes the genetic features (A)-(H).

18. A method of producing a food or beverage, a sweetener composition, a flavor or a medicament, comprising:

providing the plant according to claim 2 or the seed, tissue, dried leaf, tissue culture or cell thereof;

obtaining an extract from the plant, seed, tissue, dried leaf, tissue culture or cell;

purifying at least one of RebD, RebM and RebN from the extract; and adding the at least one of RebD, RebM and RebN to a raw material for the food or beverage, sweetener composition, flavor or medicament, wherein the seed includes the genetic features (A)-(H).

* * * * *

SEQUENCE LISTING

```
<160> NUMBER OF SEQ ID NOS: 148

<210> SEQ ID NO 1
<211> LENGTH: 203
<212> TYPE: DNA
<213> ORGANISM: Stevia rebaudiana

<400> SEQUENCE: 1

aattatatga tagaaattgt tttcacattt tgtgtgccat acacgtcaac gcctctaagc      60

cacacgatta aggtatgaca tttagaataa aatcttttat tattggaaga tagagacaaa     120

atcttttctt tccttattta ttttttataa taattacacg catcttctat tctcaactac     180

tttaacctat atgcgctagt cca                                             203


<210> SEQ ID NO 2
<211> LENGTH: 364
<212> TYPE: DNA
<213> ORGANISM: Stevia rebaudiana

<400> SEQUENCE: 2

gaaactgaaa gagaagtaag ataacagaat gcgtttyttc gtaaataatc ttttctttta      60

tttttatctt caaaaaataa ataaccaaga tttgtttgga tttgtttcta tttatttaga     120

caaatcatta ttaatattta atmtttcycc gtgaattata tgatagaaat tgttttcaca     180

ttttgtgtgc cayacacgtc aacgcctcta agccacacga ttaaggtatg acatttagaa     240

taaaatcttt tattattgga agatagagac aaaatctttt ctttccttat ttattttttta     300

taataattac acgcatcttc tattctcaac tactttaacc tatatgcgct agtccactac     360

gtag                                                                  364
```

<210> SEQ ID NO 3
<211> LENGTH: 202
<212> TYPE: DNA
<213> ORGANISM: Stevia rebaudiana

<400> SEQUENCE: 3
agagaagtaa gwtaacagaa tgcgtttctt cgtaaataat cttttctttt atttttatct 60
tcaaaaaata aataaccaag atttgtttgg atttgtttct atttatttag acaaatcatt 120
attaatattt aatmtttcyc cgtgaattat atgatagaaa ttgttttcac attttgtgtg 180
ccayacacgt caacgcctct aa 202

<210> SEQ ID NO 4
<211> LENGTH: 137
<212> TYPE: DNA
<213> ORGANISM: Stevia rebaudiana

<400> SEQUENCE: 4
ccaagatttg tttggatttg tttctattta tttagacaaa tcattattaa tatttaatat 60
ttcyccgtga attatatgat agaaattgtt ttcacatttt gtgtgccaya cacgtcaacg 120
cctctaagcc acacgat 137

<210> SEQ ID NO 5
<211> LENGTH: 137
<212> TYPE: DNA
<213> ORGANISM: Stevia rebaudiana

<400> SEQUENCE: 5
ccaagatttg tttggatttg tttctattta tttagacaaa tcattattaa tatttaatmt 60
ttccccgtga attatatgat agaaattgtt ttcacatttt gtgtgccaya cacgtcaacg 120
cctctaagcc acacgat 137

<210> SEQ ID NO 6
<211> LENGTH: 326
<212> TYPE: DNA
<213> ORGANISM: Stevia rebaudiana

<400> SEQUENCE: 6
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagt atgcatttat 300
tctatcatat tttctatgag aattgg 326

<210> SEQ ID NO 7
<211> LENGTH: 70
<212> TYPE: DNA
<213> ORGANISM: Stevia rebaudiana

<400> SEQUENCE: 7
tgattttgaa aggatctgac tgtatgttta taagacatag ttatgagttt gaaccccaat 60
ggctaaccct 70

<210> SEQ ID NO 8
<211> LENGTH: 39

<212> TYPE: DNA
<213> ORGANISM: Artificial Sequence
<220> FEATURE:
<223> OTHER INFORMATION: Synthetic DNA

<400> SEQUENCE: 8
aattatatga tagaaattgt tttcacattt tgtgtgcca 39

<210> SEQ ID NO 9
<211> LENGTH: 26
<212> TYPE: DNA
<213> ORGANISM: Artificial Sequence
<220> FEATURE:
<223> OTHER INFORMATION: Synthetic DNA

<400> SEQUENCE: 9
tggactagcg catataggtt aaagta 26

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
gaaactgaaa gagaagtaag 20

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
ctacgtagtg gactagcgca 20

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA

<400> SEQUENCE: 12
agagaagtaa gwtaacagaa tgcg 24

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
ttagaggcgt tgacgtgtrt 20

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14

```
ccaagatttg tttggatttg tttct                                        25


<210> SEQ ID NO 15
<211> LENGTH: 19
<212> TYPE: DNA
<213> ORGANISM: Artificial Sequence
<220> FEATURE:
<223> OTHER INFORMATION: Synthetic DNA

<400> SEQUENCE: 15

atcgtgtggc ttagaggcg                                               19


<210> SEQ ID NO 16
<211> LENGTH: 25
<212> TYPE: DNA
<213> ORGANISM: Artificial Sequence
<220> FEATURE:
<223> OTHER INFORMATION: Synthetic DNA

<400> SEQUENCE: 16

ccaagatttg tttggatttg tttct                                        25


<210> SEQ ID NO 17
<211> LENGTH: 19
<212> TYPE: DNA
<213> ORGANISM: Artificial Sequence
<220> FEATURE:
<223> OTHER INFORMATION: Synthetic DNA

<400> SEQUENCE: 17

atcgtgtggc ttagaggcg                                               19


<210> SEQ ID NO 18
<211> LENGTH: 25
<212> TYPE: DNA
<213> ORGANISM: Artificial Sequence
<220> FEATURE:
<223> OTHER INFORMATION: Synthetic DNA

<400> SEQUENCE: 18

ggcagccatt gatgatgttg ttgaa                                        25


<210> SEQ ID NO 19
<211> LENGTH: 36
<212> TYPE: DNA
<213> ORGANISM: Artificial Sequence
<220> FEATURE:
<223> OTHER INFORMATION: Synthetic DNA

<400> SEQUENCE: 19

ccaattctca tagaaaatat gatagaataa atgcat                            36


<210> SEQ ID NO 20
<211> LENGTH: 32
<212> TYPE: DNA
<213> ORGANISM: Artificial Sequence
<220> FEATURE:
<223> OTHER INFORMATION: Synthetic DNA

<400> SEQUENCE: 20

tgattttgaa aggatctgac tgtatgttta ta                                32


<210> SEQ ID NO 21
<211> LENGTH: 20
<212> TYPE: DNA
<213> ORGANISM: Artificial Sequence
```

<220> FEATURE:
<223> OTHER INFORMATION: Synthetic DNA

<400> SEQUENCE: 21
agggttagcc attggggttc 20

<210> SEQ ID NO 22
<211> LENGTH: 203
<212> TYPE: DNA
<213> ORGANISM: Stevia rebaudiana

<400> SEQUENCE: 22
aattatatga tagaaattgt tttcacattt tgtgtgccac acacgtcaac gcctctaagc 60
cacacgatta aggtatgaca tttagaataa aatcttttat tattggaaga tagagacaaa 120
atcttttctt tccttattta ttttttataa taattacacg catcttctat tctcaactac 180
tttaacctat atgcgctagt cca 203

<210> SEQ ID NO 23
<211> LENGTH: 21
<212> TYPE: DNA
<213> ORGANISM: Stevia rebaudiana

<400> SEQUENCE: 23
ttgtgtgcca cacacgtcaa c 21

<210> SEQ ID NO 24
<211> LENGTH: 41
<212> TYPE: DNA
<213> ORGANISM: Stevia rebaudiana

<400> SEQUENCE: 24
ttttcacatt ttgtgtgcca cacacgtcaa cgcctctaag c 41

<210> SEQ ID NO 25
<211> LENGTH: 61
<212> TYPE: DNA
<213> ORGANISM: Stevia rebaudiana

<400> SEQUENCE: 25
atagaaattg ttttcacatt ttgtgtgcca cacacgtcaa cgcctctaag ccacacgatt 60
a 61

<210> SEQ ID NO 26
<211> LENGTH: 364
<212> TYPE: DNA
<213> ORGANISM: Stevia rebaudiana

<400> SEQUENCE: 26
gaaactgaaa gagaagtaag ttaacagaat gcgtttyttc gtaaataatc ttttctttta 60
tttttatctt caaaaaataa ataaccaaga tttgtttgga tttgtttcta tttatttaga 120
caaatcatta ttaatattta atmtttcycc gtgaattata tgatagaaat tgttttcaca 180
ttttgtgtgc cayacacgtc aacgcctcta agccacacga ttaaggtatg acatttagaa 240
taaaatcttt tattattgga agatagagac aaaatctttt ctttccttat ttattttta 300 taataattac acgcatcttc tattctcaac tactttaacc tatatgcgct agtccactac 360
gtag 364

<210> SEQ ID NO 27

<211> LENGTH: 21
<212> TYPE: DNA
<213> ORGANISM: Stevia rebaudiana

<400> SEQUENCE: 27
gagaagtaag ttaacagaat g 21

<210> SEQ ID NO 28
<211> LENGTH: 41
<212> TYPE: DNA
<213> ORGANISM: Stevia rebaudiana

<400> SEQUENCE: 28
gaaactgaaa gagaagtaag ttaacagaat gcgtttyttc g 41

<210> SEQ ID NO 29
<211> LENGTH: 61
<212> TYPE: DNA
<213> ORGANISM: Stevia rebaudiana

<400> SEQUENCE: 29
aatgtttaag gaaactgaaa gagaagtaag ttaacagaat gcgtttyttc gtaaataatc 60
t 61

<210> SEQ ID NO 30
<211> LENGTH: 202
<212> TYPE: DNA
<213> ORGANISM: Stevia rebaudiana

<400> SEQUENCE: 30
agagaagtaa gwtaacagaa tgcgtttttt cgtaaataat cttttctttt atttttatct 60
tcaaaaaata aataaccaag atttgtttgg atttgtttct atttatttag acaaatcatt 120
attaatattt aatmtttcyc cgtgaattat atgatagaaa ttgttttcac attttgtgtg 180
ccayacacgt caacgcctct aa 202

<210> SEQ ID NO 31
<211> LENGTH: 21
<212> TYPE: DNA
<213> ORGANISM: Stevia rebaudiana

<400> SEQUENCE: 31
gaatgcgttt tttcgtaaat a 21

<210> SEQ ID NO 32
<211> LENGTH: 41
<212> TYPE: DNA
<213> ORGANISM: Stevia rebaudiana

<400> SEQUENCE: 32
taagwtaaca gaatgcgttt tttcgtaaat aatcttttct t 41

<210> SEQ ID NO 33
<211> LENGTH: 61
<212> TYPE: DNA
<213> ORGANISM: Stevia rebaudiana

<400> SEQUENCE: 33
gaaagagaag taagwtaaca gaatgcgttt tttcgtaaat aatcttttct tttattttta 60
t 61

<210> SEQ ID NO 34
<211> LENGTH: 137
<212> TYPE: DNA
<213> ORGANISM: Stevia rebaudiana

<400> SEQUENCE: 34
ccaagatttg tttggatttg tttctattta tttagacaaa tcattattaa tatttaatct 60
ttcyccgtga attatatgat agaaattgtt ttcacatttt gtgtgccaya cacgtcaacg 120
cctctaagcc acacgat 137

<210> SEQ ID NO 35
<211> LENGTH: 21
<212> TYPE: DNA
<213> ORGANISM: Stevia rebaudiana

<400> SEQUENCE: 35
aatatttaat ctttcyccgt g 21

<210> SEQ ID NO 36
<211> LENGTH: 41
<212> TYPE: DNA
<213> ORGANISM: Stevia rebaudiana

<400> SEQUENCE: 36
aatcattatt aatatttaat ctttcyccgt gaattatatg a 41

<210> SEQ ID NO 37
<211> LENGTH: 61
<212> TYPE: DNA
<213> ORGANISM: Stevia rebaudiana

<400> SEQUENCE: 37
tatttagaca aatcattatt aatatttaat ctttcyccgt gaattatatg atagaaattg 60
t 61

<210> SEQ ID NO 38
<211> LENGTH: 137
<212> TYPE: DNA
<213> ORGANISM: Stevia rebaudiana

<400> SEQUENCE: 38
ccaagatttg tttggatttg tttctattta tttagacaaa tcattattaa tatttaatmt 60
ttctccgtga attatatgat agaaattgtt ttcacatttt gtgtgccaya cacgtcaacg 120
cctctaagcc acacgat 137

<210> SEQ ID NO 39
<211> LENGTH: 21
<212> TYPE: DNA
<213> ORGANISM: Stevia rebaudiana

<400> SEQUENCE: 39
ttaatmtttc tccgtgaatt a 21

<210> SEQ ID NO 40
<211> LENGTH: 41
<212> TYPE: DNA
<213> ORGANISM: Stevia rebaudiana

<400> SEQUENCE: 40
ttattaatat ttaatmtttc tccgtgaatt atatgataga a 41

<210> SEQ ID NO 41
<211> LENGTH: 61
<212> TYPE: DNA
<213> ORGANISM: Stevia rebaudiana

<400> SEQUENCE: 41
agacaaatca ttattaatat ttaatmtttc tccgtgaatt atatgataga aattgttttc 60
a 61

<210> SEQ ID NO 42
<211> LENGTH: 326
<212> TYPE: DNA
<213> ORGANISM: Stevia rebaudiana

<400> SEQUENCE: 42
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagc atgcatttat 300
tctatcatat tttctatgag aattgg 326

<210> SEQ ID NO 43
<211> LENGTH: 21
<212> TYPE: DNA
<213> ORGANISM: Stevia rebaudiana

<400> SEQUENCE: 43
atgcttttag catgcattta t 21

<210> SEQ ID NO 44
<211> LENGTH: 41
<212> TYPE: DNA
<213> ORGANISM: Stevia rebaudiana

<400> SEQUENCE: 44
cccctaattt atgcttttag catgcattta ttctatcata t 41

<210> SEQ ID NO 45
<211> LENGTH: 61
<212> TYPE: DNA
<213> ORGANISM: Stevia rebaudiana

<400> SEQUENCE: 45
gatagtgttt cccctaattt atgcttttag catgcattta ttctatcata ttttctatga 60
g 61

<210> SEQ ID NO 46
<211> LENGTH: 70
<212> TYPE: DNA
<213> ORGANISM: Stevia rebaudiana

<400> SEQUENCE: 46
tgattttgaa aggatctgac tgtatgttta tatgacatag ttatgagttt gaaccccaat 60
ggctaaccct 70

<210> SEQ ID NO 47
<211> LENGTH: 21

<212> TYPE: DNA
<213> ORGANISM: Stevia rebaudiana

<400> SEQUENCE: 47
tatgtttata tgacatagtt a 21

<210> SEQ ID NO 48
<211> LENGTH: 41
<212> TYPE: DNA
<213> ORGANISM: Stevia rebaudiana

<400> SEQUENCE: 48
gatctgactg tatgtttata tgacatagtt atgagtttga a 41

<210> SEQ ID NO 49
<211> LENGTH: 61
<212> TYPE: DNA
<213> ORGANISM: Stevia rebaudiana

<400> SEQUENCE: 49
attttgaaag gatctgactg tatgtttata tgacatagtt atgagtttga accccaatgg 60
c 61

<210> SEQ ID NO 50
<211> LENGTH: 39
<212> TYPE: DNA
<213> ORGANISM: Artificial Sequence
<220> FEATURE:
<223> OTHER INFORMATION: Synthetic DNA

<400> SEQUENCE: 50
aattatatga tagaaattgt tttcacattt tgtgtgccg 39

<210> SEQ ID NO 51
<211> LENGTH: 26
<212> TYPE: DNA
<213> ORGANISM: Artificial Sequence
<220> FEATURE:
<223> OTHER INFORMATION: Synthetic DNA

<400> SEQUENCE: 51
tggactagcg catataggtt aaagta 26

<210> SEQ ID NO 52
<211> LENGTH: 203
<212> TYPE: DNA
<213> ORGANISM: Artificial Sequence
<220> FEATURE:
<223> OTHER INFORMATION: Synthetic DNA

<400> SEQUENCE: 52
aattatatga tagaaattgt tttcacattt tgtgtgccgc acacgtcaac gcctctaagc 60
cacacgatta aggtatgaca tttagaataa aatcttttat tattggaaga tagagacaaa 120
atcttttctt tccttattta ttttttataa taattacacg catcttctat tctcaactac 180
tttaacctat atgcgctagt cca 203

<210> SEQ ID NO 53
<211> LENGTH: 203
<212> TYPE: DNA
<213> ORGANISM: Artificial Sequence
<220> FEATURE:
<223> OTHER INFORMATION: Synthetic DNA

<400> SEQUENCE: 53
aattatatga tagaaattgt tttcacattt tgtgtgccgt acacgtcaac gcctctaagc 60
cacacgatta aggtatgaca tttagaataa aatcttttat tattggaaga tagagacaaa 120
atcttttctt tccttattta ttttttataa taattacacg catcttctat tctcaactac 180
tttaacctat atgcgctagt cca 203

<210> SEQ ID NO 54
<211> LENGTH: 40
<212> TYPE: DNA
<213> ORGANISM: Artificial Sequence
<220> FEATURE:
<223> OTHER INFORMATION: Synthetic DNA

<400> SEQUENCE: 54
aattatatga tagaaattgt tttcacattt tgtgtgccgt 40

<210> SEQ ID NO 55
<211> LENGTH: 163
<212> TYPE: DNA
<213> ORGANISM: Artificial Sequence
<220> FEATURE:
<223> OTHER INFORMATION: Synthetic DNA

<400> SEQUENCE: 55
acacgtcaac gcctctaagc cacacgatta aggtatgaca tttagaataa aatcttttat 60
tattggaaga tagagacaaa atcttttctt tccttattta ttttttataa taattacacg 120
catcttctat tctcaactac tttaacctat atgcgctagt cca 163

<210> SEQ ID NO 56
<211> LENGTH: 20
<212> TYPE: DNA
<213> ORGANISM: Artificial Sequence
<220> FEATURE:
<223> OTHER INFORMATION: Synthetic DNA

<400> SEQUENCE: 56
gaaactgaaa gagaagaacg 20

<210> SEQ ID NO 57
<211> LENGTH: 20
<212> TYPE: DNA
<213> ORGANISM: Artificial Sequence
<220> FEATURE:
<223> OTHER INFORMATION: Synthetic DNA

<400> SEQUENCE: 57
ctacgtagtg gactagcgca 20

<210> SEQ ID NO 58
<211> LENGTH: 364
<212> TYPE: DNA
<213> ORGANISM: Artificial Sequence
<220> FEATURE:
<223> OTHER INFORMATION: Synthetic DNA

<400> SEQUENCE: 58
gaaactgaaa gagaagaacg ttaacagaat gcgtttyttc gtaaataatc ttttctttta 60
tttttatctt caaaaaataa ataaccaaga tttgtttgga tttgtttcta tttatttaga 120
caaatcatta ttaatattta atmtttcycc gtgaattata tgatagaaat tgttttcaca 180
ttttgtgtgc cayacacgtc aacgcctcta agccacacga ttaaggtatg acatttagaa 240
taaaatcttt tattattgga agatagagac aaaatctttt ctttccttat ttattttta 300 taataattac acgcatcttc tattctcaac tactttaacc tatatgcgct agtccactac 360
gtag 364

<210> SEQ ID NO 59
<211> LENGTH: 364
<212> TYPE: DNA
<213> ORGANISM: Artificial Sequence
<220> FEATURE:
<223> OTHER INFORMATION: Synthetic DNA

<400> SEQUENCE: 59
gaaactgaaa gagaagaacg ataacagaat gcgtttyttc gtaaataatc ttttctttta 60
tttttatctt caaaaaataa ataaccaaga tttgtttgga tttgtttcta tttatttaga 120
caaatcatta ttaatattta atmtttcycc gtgaattata tgatagaaat tgttttcaca 180
ttttgtgtgc cayacacgtc aacgcctcta agccacacga ttaaggtatg acatttagaa 240
taaaatcttt tattattgga agatagagac aaaatctttt ctttccttat ttattttta 300 taataattac acgcatcttc tattctcaac tactttaacc tatatgcgct agtccactac 360
gtag 364

<210> SEQ ID NO 60
<211> LENGTH: 18
<212> TYPE: DNA
<213> ORGANISM: Artificial Sequence
<220> FEATURE:
<223> OTHER INFORMATION: Synthetic DNA

<400> SEQUENCE: 60
gaaactgaaa gagaagaa 18

<210> SEQ ID NO 61
<211> LENGTH: 346
<212> TYPE: DNA
<213> ORGANISM: Artificial Sequence
<220> FEATURE:
<223> OTHER INFORMATION: Synthetic DNA

<400> SEQUENCE: 61
cgttaacaga atgcgtttyt tcgtaaataa tcttttcttt tatttttatc ttcaaaaaat 60
aaataaccaa gatttgtttg gatttgtttc tatttattta gacaaatcat tattaatatt 120
taatmtttcy ccgtgaatta tatgatagaa attgttttca cattttgtgt gccayacacg 180
tcaacgcctc taagccacac gattaaggta tgacatttag aataaaatct tttattattg 240
gaagatagag acaaaatctt ttctttcctt atttattttt tataataatt acacgcatct 300
tctattctca actactttaa cctatatgcg ctagtccact acgtag 346

<210> SEQ ID NO 62
<211> LENGTH: 20
<212> TYPE: DNA
<213> ORGANISM: Artificial Sequence
<220> FEATURE:
<223> OTHER INFORMATION: Synthetic DNA

<400> SEQUENCE: 62
taagwtaaca gaatgcgagc 20

<210> SEQ ID NO 63

<211> LENGTH: 20
<212> TYPE: DNA
<213> ORGANISM: Artificial Sequence
<220> FEATURE:
<223> OTHER INFORMATION: Synthetic DNA

<400> SEQUENCE: 63
acgtagtgga ctagcgcata 20

<210> SEQ ID NO 64
<211> LENGTH: 353
<212> TYPE: DNA
<213> ORGANISM: Artificial Sequence
<220> FEATURE:
<223> OTHER INFORMATION: Synthetic DNA

<400> SEQUENCE: 64
taagwtaaca gaatgcgagc tttcgtaaat aatcttttct tttattttta tcttcaaaaa 60
ataaataacc aagatttgtt tggatttgtt tctatttatt tagacaaatc attattaata 120
tttaatmttt cyccgtgaat tatatgatag aaattgtttt cacattttgt gtgccayaca 180
cgtcaacgcc tctaagccac acgattaagg tatgacattt agaataaaat cttttattat 240
tggaagatag agacaaaatc ttttctttcc ttatttattt tttataataa ttacacgcat 300
cttctattct caactacttt aacctatatg cgctatgcgc tagtccacta cgt 353

<210> SEQ ID NO 65
<211> LENGTH: 353
<212> TYPE: DNA
<213> ORGANISM: Artificial Sequence
<220> FEATURE:
<223> OTHER INFORMATION: Synthetic DNA

<400> SEQUENCE: 65
taagwtaaca gaatgcgagc cttcgtaaat aatcttttct tttattttta tcttcaaaaa 60
ataaataacc aagatttgtt tggatttgtt tctatttatt tagacaaatc attattaata 120
tttaatmttt cyccgtgaat tatatgatag aaattgtttt cacattttgt gtgccayaca 180
cgtcaacgcc tctaagccac acgattaagg tatgacattt agaataaaat cttttattat 240
tggaagatag agacaaaatc ttttctttcc ttatttattt tttataataa ttacacgcat 300
cttctattct caactacttt aacctatatg cgctatgcgc tagtccacta cgt 353

<210> SEQ ID NO 66
<211> LENGTH: 19
<212> TYPE: DNA
<213> ORGANISM: Artificial Sequence
<220> FEATURE:
<223> OTHER INFORMATION: Synthetic DNA

<400> SEQUENCE: 66
taagwtaaca gaatgcgag 19

<210> SEQ ID NO 67
<211> LENGTH: 334
<212> TYPE: DNA
<213> ORGANISM: Artificial Sequence
<220> FEATURE:
<223> OTHER INFORMATION: Synthetic DNA

<400> SEQUENCE: 67
ctttcgtaaa taatcttttc ttttattttt atcttcaaaa aataaataac caagatttgt 60
ttggatttgt ttctatttat ttagacaaat cattattaat atttaatmtt tcyccgtgaa 120
ttatatgata gaaattgttt tcacattttg tgtgccayac acgtcaacgc ctctaagcca 180
cacgattaag gtatgacatt tagaataaaa tcttttatta ttggaagata gagacaaaat 240
cttttctttc cttatttatt ttttataata attacacgca tcttctattc tcaactactt 300
taacctatat gcgctatgcg ctagtccact acgt 334

<210> SEQ ID NO 68
<211> LENGTH: 21
<212> TYPE: DNA
<213> ORGANISM: Artificial Sequence
<220> FEATURE:
<223> OTHER INFORMATION: Synthetic DNA

<400> SEQUENCE: 68
aaatcattat taatatttaa g 21

<210> SEQ ID NO 69
<211> LENGTH: 20
<212> TYPE: DNA
<213> ORGANISM: Artificial Sequence
<220> FEATURE:
<223> OTHER INFORMATION: Synthetic DNA

<400> SEQUENCE: 69
tggcgccggc gaacggttgt 20

<210> SEQ ID NO 70
<211> LENGTH: 349
<212> TYPE: DNA
<213> ORGANISM: Artificial Sequence
<220> FEATURE:
<223> OTHER INFORMATION: Synthetic DNA

<400> SEQUENCE: 70
aaatcattat taatatttaa gctttcyccg tgaattatat gatagaaatt gttttcacat 60
tttgtgtgcc ayacacgtca acgcctctaa gccacacgat taaggtatga catttagaat 120
aaaatctttt attattggaa gatagagaca aaatcttttc tttccttatt tatttttat 180 aataattaca cgcatcttct attctcaact actttaacct atatgcgcta gtccactacg 240
tagagtcgtt cattctgttt tcgagtttct acgttcattc tgtttttgag tgtaaacatc 300
agtcaaatcc catggaaaat aaaacggaga caaccgttcg ccggcgcca 349

<210> SEQ ID NO 71
<211> LENGTH: 349
<212> TYPE: DNA
<213> ORGANISM: Artificial Sequence
<220> FEATURE:
<223> OTHER INFORMATION: Synthetic DNA

<400> SEQUENCE: 71
aaatcattat taatatttaa gatttcyccg tgaattatat gatagaaatt gttttcacat 60
tttgtgtgcc ayacacgtca acgcctctaa gccacacgat taaggtatga catttagaat 120
aaaatctttt attattggaa gatagagaca aaatcttttc tttccttatt tatttttat 180 aataattaca cgcatcttct attctcaact actttaacct atatgcgcta gtccactacg 240
tagagtcgtt cattctgttt tcgagtttct acgttcattc tgtttttgag tgtaaacatc 300
agtcaaatcc catggaaaat aaaacggaga caaccgttcg ccggcgcca 349

<210> SEQ ID NO 72

<211> LENGTH: 21
<212> TYPE: DNA
<213> ORGANISM: Artificial Sequence
<220> FEATURE:
<223> OTHER INFORMATION: Synthetic DNA

<400> SEQUENCE: 72
aaatcattat taatatttaa g 21

<210> SEQ ID NO 73
<211> LENGTH: 328
<212> TYPE: DNA
<213> ORGANISM: Artificial Sequence
<220> FEATURE:
<223> OTHER INFORMATION: Synthetic DNA

<400> SEQUENCE: 73
ctttcyccgt gaattatatg atagaaattg ttttcacatt ttgtgtgcca yacacgtcaa 60
cgcctctaag ccacacgatt aaggtatgac atttagaata aaatctttta ttattggaag 120
atagagacaa aatcttttct ttccttattt atttttata ataattacac gcatcttcta 180
ttctcaacta ctttaaccta tatgcgctag tccactacgt agagtcgttc attctgtttt 240
cgagtttcta cgttcattct gtttttgagt gtaaacatca gtcaaatccc atggaaaata 300
aaacggagac aaccgttcgc cggcgcca 328

<210> SEQ ID NO 74
<211> LENGTH: 22
<212> TYPE: DNA
<213> ORGANISM: Artificial Sequence
<220> FEATURE:
<223> OTHER INFORMATION: Synthetic DNA

<400> SEQUENCE: 74
cattattaat atttaatmta gc 22

<210> SEQ ID NO 75
<211> LENGTH: 20
<212> TYPE: DNA
<213> ORGANISM: Artificial Sequence
<220> FEATURE:
<223> OTHER INFORMATION: Synthetic DNA

<400> SEQUENCE: 75
tctctggcgc cggcgaacgg 20

<210> SEQ ID NO 76
<211> LENGTH: 349
<212> TYPE: DNA
<213> ORGANISM: Artificial Sequence
<220> FEATURE:
<223> OTHER INFORMATION: Synthetic DNA

<400> SEQUENCE: 76
cattattaat atttaatmta gctccgtgaa ttatatgata gaaattgttt tcacattttg 60
tgtgccayac acgtcaacgc ctctaagcca cacgattaag gtatgacatt tagaataaaa 120
tcttttatta ttggaagata gagacaaaat cttttctttc cttatttatt ttttataata 180
attacacgca tcttctattc tcaactactt taacctatat gcgctagtcc actacgtaga 240
gtcgttcatt ctgttttcga gtttctacgt tcattctgtt tttgagtgta aacatcagtc 300
aaatcccatg gaaaataaaa cggagacaac cgttcgccgg cgccagaga 349

<210> SEQ ID NO 77
<211> LENGTH: 349
<212> TYPE: DNA
<213> ORGANISM: Artificial Sequence
<220> FEATURE:
<223> OTHER INFORMATION: Synthetic DNA

<400> SEQUENCE: 77
cattattaat atttaatmta gccccgtgaa ttatatgata gaaattgttt tcacattttg 60
tgtgccayac acgtcaacgc ctctaagcca cacgattaag gtatgacatt tagaataaaa 120
tcttttatta ttggaagata gagacaaaat cttttctttc cttatttatt ttttataata 180
attacacgca tcttctattc tcaactactt taacctatat gcgctagtcc actacgtaga 240
gtcgttcatt ctgttttcga gtttctacgt tcattctgtt tttgagtgta aacatcagtc 300
aaatcccatg gaaaataaaa cggagacaac cgttcgccgg cgccagaga 349

<210> SEQ ID NO 78
<211> LENGTH: 21
<212> TYPE: DNA
<213> ORGANISM: Artificial Sequence
<220> FEATURE:
<223> OTHER INFORMATION: Synthetic DNA

<400> SEQUENCE: 78
cattattaat atttaatmta g 21

<210> SEQ ID NO 79
<211> LENGTH: 328
<212> TYPE: DNA
<213> ORGANISM: Artificial Sequence
<220> FEATURE:
<223> OTHER INFORMATION: Synthetic DNA

<400> SEQUENCE: 79
ctccgtgaat tatatgatag aaattgtttt cacattttgt gtgccayaca cgtcaacgcc 60
tctaagccac acgattaagg tatgacattt agaataaaat cttttattat tggaagatag 120
agacaaaatc ttttctttcc ttatttattt tttataataa ttacacgcat cttctattct 180
caactacttt aacctatatg cgctagtcca ctacgtagag tcgttcattc tgttttcgag 240
tttctacgtt cattctgttt ttgagtgtaa acatcagtca aatcccatgg aaaataaaac 300
ggagacaacc gttcgccggc gccagaga 328

<210> SEQ ID NO 80
<211> LENGTH: 25
<212> TYPE: DNA
<213> ORGANISM: Artificial Sequence
<220> FEATURE:
<223> OTHER INFORMATION: Synthetic DNA

<400> SEQUENCE: 80
ggcagccatt gatgatgttg ttgaa 25

<210> SEQ ID NO 81
<211> LENGTH: 36
<212> TYPE: DNA
<213> ORGANISM: Artificial Sequence
<220> FEATURE:
<223> OTHER INFORMATION: Synthetic DNA

<400> SEQUENCE: 81
ccaattctca tagaaaatat gatagaataa atgcgt 36

<210> SEQ ID NO 82
<211> LENGTH: 326
<212> TYPE: DNA
<213> ORGANISM: Artificial Sequence
<220> FEATURE:
<223> OTHER INFORMATION: Synthetic DNA

<400> SEQUENCE: 82
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagc acgcatttat 300
tctatcatat tttctatgag aattgg 326

<210> SEQ ID NO 83
<211> LENGTH: 326
<212> TYPE: DNA
<213> ORGANISM: Artificial Sequence
<220> FEATURE:
<223> OTHER INFORMATION: Synthetic DNA

<400> SEQUENCE: 83
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagt acgcatttat 300
tctatcatat tttctatgag aattgg 326

<210> SEQ ID NO 84
<211> LENGTH: 290
<212> TYPE: DNA
<213> ORGANISM: Artificial Sequence
<220> FEATURE:
<223> OTHER INFORMATION: Synthetic DNA

<400> SEQUENCE: 84
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagt 290

<210> SEQ ID NO 85
<211> LENGTH: 36
<212> TYPE: DNA
<213> ORGANISM: Artificial Sequence
<220> FEATURE:
<223> OTHER INFORMATION: Synthetic DNA

<400> SEQUENCE: 85
acgcatttat tctatcatat tttctatgag aattgg 36

<210> SEQ ID NO 86
<211> LENGTH: 32

<212> TYPE: DNA
<213> ORGANISM: Artificial Sequence
<220> FEATURE:
<223> OTHER INFORMATION: Synthetic DNA

<400> SEQUENCE: 86
tgattttgaa aggatctgac tgtatgtttt ta 32

<210> SEQ ID NO 87
<211> LENGTH: 20
<212> TYPE: DNA
<213> ORGANISM: Artificial Sequence
<220> FEATURE:
<223> OTHER INFORMATION: Synthetic DNA

<400> SEQUENCE: 87
tgttgaccat caagccacat 20

<210> SEQ ID NO 88
<211> LENGTH: 196
<212> TYPE: DNA
<213> ORGANISM: Artificial Sequence
<220> FEATURE:
<223> OTHER INFORMATION: Synthetic DNA

<400> SEQUENCE: 88
tgattttgaa aggatctgac tgtatgtttt tatgacatag ttatgagttt gaaccccaat 60
ggctaaccct tttagagaag ctccatcacc taccggtggt tcctgtcgga ttattgccac 120
cagaaaaacc caccaacatc gaagacggga atgatgagac gtgggacaca gtcaagatgt 180
ggcttgatgg tcaaca 196

<210> SEQ ID NO 89
<211> LENGTH: 196
<212> TYPE: DNA
<213> ORGANISM: Artificial Sequence
<220> FEATURE:
<223> OTHER INFORMATION: Synthetic DNA

<400> SEQUENCE: 89
tgattttgaa aggatctgac tgtatgtttt taagacatag ttatgagttt gaaccccaat 60
ggctaaccct tttagagaag ctccatcacc taccggtggt tcctgtcgga ttattgccac 120
cagaaaaacc caccaacatc gaagacggga atgatgagac gtgggacaca gtcaagatgt 180
ggcttgatgg tcaaca 196

<210> SEQ ID NO 90
<211> LENGTH: 30
<212> TYPE: DNA
<213> ORGANISM: Artificial Sequence
<220> FEATURE:
<223> OTHER INFORMATION: Synthetic DNA

<400> SEQUENCE: 90
tgattttgaa aggatctgac tgtatgtttt 30

<210> SEQ ID NO 91
<211> LENGTH: 166
<212> TYPE: DNA
<213> ORGANISM: Artificial Sequence
<220> FEATURE:
<223> OTHER INFORMATION: Synthetic DNA

<400> SEQUENCE: 91

```
taagacatag ttatgagttt gaaccccaat ggctaaccct tttagagaag ctccatcacc     60

taccggtggt tcctgtcgga ttattgccac cagaaaaacc caccaacatc gaagacggga    120

atgatgagac gtgggacaca gtcaagatgt ggcttgatgg tcaaca                   166


<210> SEQ ID NO 92
<211> LENGTH: 21
<212> TYPE: DNA
<213> ORGANISM: Stevia rebaudiana

<400> SEQUENCE: 92

ttgtgtgcca tacacgtcaa c                                               21


<210> SEQ ID NO 93
<211> LENGTH: 41
<212> TYPE: DNA
<213> ORGANISM: Stevia rebaudiana

<400> SEQUENCE: 93

ttttcacatt ttgtgtgcca tacacgtcaa cgcctctaag c                         41


<210> SEQ ID NO 94
<211> LENGTH: 61
<212> TYPE: DNA
<213> ORGANISM: Stevia rebaudiana

<400> SEQUENCE: 94

atagaaattg ttttcacatt ttgtgtgcca tacacgtcaa cgcctctaag ccacacgatt     60

a                                                                     61


<210> SEQ ID NO 95
<211> LENGTH: 21
<212> TYPE: DNA
<213> ORGANISM: Stevia rebaudiana

<400> SEQUENCE: 95

gagaagtaag ataacagaat g                                               21


<210> SEQ ID NO 96
<211> LENGTH: 41
<212> TYPE: DNA
<213> ORGANISM: Stevia rebaudiana

<400> SEQUENCE: 96

gaaactgaaa gagaagtaag ataacagaat gcgtttyttc g                         41


<210> SEQ ID NO 97
<211> LENGTH: 61
<212> TYPE: DNA
<213> ORGANISM: Stevia rebaudiana

<400> SEQUENCE: 97

aatgtttaag gaaactgaaa gagaagtaag ataacagaat gcgtttyttc gtaaataatc     60

t                                                                     61


<210> SEQ ID NO 98
<211> LENGTH: 21
<212> TYPE: DNA
<213> ORGANISM: Stevia rebaudiana

<400> SEQUENCE: 98

gaatgcgttt cttcgtaaat a                                               21
```

<210> SEQ ID NO 99
<211> LENGTH: 41
<212> TYPE: DNA
<213> ORGANISM: Stevia rebaudiana

<400> SEQUENCE: 99
taagwtaaca gaatgcgttt cttcgtaaat aatcttttct t 41

<210> SEQ ID NO 100
<211> LENGTH: 61
<212> TYPE: DNA
<213> ORGANISM: Stevia rebaudiana

<400> SEQUENCE: 100
gaaagagaag taagwtaaca gaatgcgttt cttcgtaaat aatcttttct tttattttta 60
t 61

<210> SEQ ID NO 101
<211> LENGTH: 21
<212> TYPE: DNA
<213> ORGANISM: Stevia rebaudiana

<400> SEQUENCE: 101
aatatttaat atttcyccgt g 21

<210> SEQ ID NO 102
<211> LENGTH: 41
<212> TYPE: DNA
<213> ORGANISM: Stevia rebaudiana

<400> SEQUENCE: 102
aatcattatt aatatttaat atttcyccgt gaattatatg a 41

<210> SEQ ID NO 103
<211> LENGTH: 61
<212> TYPE: DNA
<213> ORGANISM: Stevia rebaudiana

<400> SEQUENCE: 103
tatttagaca aatcattatt aatatttaat atttcyccgt gaattatatg atagaaattg 60
t 61

<210> SEQ ID NO 104
<211> LENGTH: 21
<212> TYPE: DNA
<213> ORGANISM: Stevia rebaudiana

<400> SEQUENCE: 104
ttaatmtttc cccgtgaatt a 21

<210> SEQ ID NO 105
<211> LENGTH: 41
<212> TYPE: DNA
<213> ORGANISM: Stevia rebaudiana

<400> SEQUENCE: 105
ttattaatat ttaatmtttc cccgtgaatt atatgataga a 41

<210> SEQ ID NO 106
<211> LENGTH: 61
<212> TYPE: DNA

<213> ORGANISM: Stevia rebaudiana

<400> SEQUENCE: 106
agacaaatca ttattaatat ttaatmtttc cccgtgaatt atatgataga aattgttttc 60
a 61

<210> SEQ ID NO 107
<211> LENGTH: 21
<212> TYPE: DNA
<213> ORGANISM: Stevia rebaudiana

<400> SEQUENCE: 107
atgcttttag tatgcattta t 21

<210> SEQ ID NO 108
<211> LENGTH: 41
<212> TYPE: DNA
<213> ORGANISM: Stevia rebaudiana

<400> SEQUENCE: 108
cccctaattt atgcttttag tatgcattta ttctatcata t 41

<210> SEQ ID NO 109
<211> LENGTH: 61
<212> TYPE: DNA
<213> ORGANISM: Stevia rebaudiana

<400> SEQUENCE: 109
gatagtgttt cccctaattt atgcttttag tatgcattta ttctatcata ttttctatga 60
g 61

<210> SEQ ID NO 110
<211> LENGTH: 21
<212> TYPE: DNA
<213> ORGANISM: Stevia rebaudiana

<400> SEQUENCE: 110
tatgtttata agacatagtt a 21

<210> SEQ ID NO 111
<211> LENGTH: 41
<212> TYPE: DNA
<213> ORGANISM: Stevia rebaudiana

<400> SEQUENCE: 111
gatctgactg tatgtttata agacatagtt atgagtttga a 41

<210> SEQ ID NO 112
<211> LENGTH: 61
<212> TYPE: DNA
<213> ORGANISM: Stevia rebaudiana

<400> SEQUENCE: 112
attttgaaag gatctgactg tatgtttata agacatagtt atgagtttga accccaatgg 60
c 61

<210> SEQ ID NO 113
<211> LENGTH: 20
<212> TYPE: DNA
<213> ORGANISM: Artificial Sequence
<220> FEATURE:
<223> OTHER INFORMATION: Synthetic DNA

<400> SEQUENCE: 113
ttttcacatt ttgtgtgtca 20

<210> SEQ ID NO 114
<211> LENGTH: 20
<212> TYPE: DNA
<213> ORGANISM: Artificial Sequence
<220> FEATURE:
<223> OTHER INFORMATION: Synthetic DNA

<400> SEQUENCE: 114
ttttcacatt ttgtgtgccg 20

<210> SEQ ID NO 115
<211> LENGTH: 340
<212> TYPE: DNA
<213> ORGANISM: Artificial Sequence
<220> FEATURE:
<223> OTHER INFORMATION: Synthetic DNA

<400> SEQUENCE: 115
ttttcacatt ttgtgtgcca tacacgtcaa cgcctctaag ccacacgatt aaggtatgac 60
atttagaata aaatctttta ttattggaag atagagacaa aatcttttct ttccttattt 120
attttttata ataattacac gcatcttcta ttctcaacta ctttaaccta tatgcgctag 180
tccactacgt agagtcgttc attctgtttt cgagtttcta cgttcattct gtttttgagt 240
gtaaacatca gtcaaatccc atggaaaata aaacggagac aaccgttcgc cggcgccaga 300
gaataatatt gttcccggta ccatttcaag gccacataag 340

<210> SEQ ID NO 116
<211> LENGTH: 340
<212> TYPE: DNA
<213> ORGANISM: Artificial Sequence
<220> FEATURE:
<223> OTHER INFORMATION: Synthetic DNA

<400> SEQUENCE: 116
ttttcacatt ttgtgtgcca cacacgtcaa cgcctctaag ccacacgatt aaggtatgac 60
atttagaata aaatctttta ttattggaag atagagacaa aatcttttct ttccttattt 120
attttttata ataattacac gcatcttcta ttctcaacta ctttaaccta tatgcgctag 180
tccactacgt agagtcgttc attctgtttt cgagtttcta cgttcattct gtttttgagt 240
gtaaacatca gtcaaatccc atggaaaata aaacggagac aaccgttcgc cggcgccaga 300
gaataatatt gttcccggta ccatttcaag gccacataag 340

<210> SEQ ID NO 117
<211> LENGTH: 21
<212> TYPE: DNA
<213> ORGANISM: Artificial Sequence
<220> FEATURE:
<223> OTHER INFORMATION: Synthetic DNA

<400> SEQUENCE: 117
cttatgtggc cttgaaatgg t 21

<210> SEQ ID NO 118
<211> LENGTH: 20
<212> TYPE: DNA
<213> ORGANISM: Artificial Sequence
<220> FEATURE:

<223> OTHER INFORMATION: Synthetic DNA

<400> SEQUENCE: 118
gaaactgaaa gagaagtagc 20

<210> SEQ ID NO 119
<211> LENGTH: 20
<212> TYPE: DNA
<213> ORGANISM: Artificial Sequence
<220> FEATURE:
<223> OTHER INFORMATION: Synthetic DNA

<400> SEQUENCE: 119
gaaactgaaa gagaagttaa 20

<210> SEQ ID NO 120
<211> LENGTH: 20
<212> TYPE: DNA
<213> ORGANISM: Artificial Sequence
<220> FEATURE:
<223> OTHER INFORMATION: Synthetic DNA

<400> SEQUENCE: 120
taagwtaaca gaatgagatc 20

<210> SEQ ID NO 121
<211> LENGTH: 20
<212> TYPE: DNA
<213> ORGANISM: Artificial Sequence
<220> FEATURE:
<223> OTHER INFORMATION: Synthetic DNA

<400> SEQUENCE: 121
taagwtaaca gaatgagtac 20

<210> SEQ ID NO 122
<211> LENGTH: 21
<212> TYPE: DNA
<213> ORGANISM: Artificial Sequence
<220> FEATURE:
<223> OTHER INFORMATION: Synthetic DNA

<400> SEQUENCE: 122
aaatcattat taatatttga t 21

<210> SEQ ID NO 123
<211> LENGTH: 21
<212> TYPE: DNA
<213> ORGANISM: Artificial Sequence
<220> FEATURE:
<223> OTHER INFORMATION: Synthetic DNA

<400> SEQUENCE: 123
aaatcattat taatattaga t 21

<210> SEQ ID NO 124
<211> LENGTH: 22
<212> TYPE: DNA
<213> ORGANISM: Artificial Sequence
<220> FEATURE:
<223> OTHER INFORMATION: Synthetic DNA

<400> SEQUENCE: 124
cattattaat atttaatmtt ga 22

<210> SEQ ID NO 125
<211> LENGTH: 22
<212> TYPE: DNA
<213> ORGANISM: Artificial Sequence
<220> FEATURE:
<223> OTHER INFORMATION: Synthetic DNA

<400> SEQUENCE: 125
cattattaat atttaatmga tc 22

<210> SEQ ID NO 126
<211> LENGTH: 36
<212> TYPE: DNA
<213> ORGANISM: Artificial Sequence
<220> FEATURE:
<223> OTHER INFORMATION: Synthetic DNA

<400> SEQUENCE: 126
ccaattctca tagaaaatat gatagaataa atgtat 36

<210> SEQ ID NO 127
<211> LENGTH: 36
<212> TYPE: DNA
<213> ORGANISM: Artificial Sequence
<220> FEATURE:
<223> OTHER INFORMATION: Synthetic DNA

<400> SEQUENCE: 127
ccaattctca tagaaaatat gatagaataa atgcaa 36

<210> SEQ ID NO 128
<211> LENGTH: 32
<212> TYPE: DNA
<213> ORGANISM: Artificial Sequence
<220> FEATURE:
<223> OTHER INFORMATION: Synthetic DNA

<400> SEQUENCE: 128
tgattttgaa aggatctgac tgtatgttta ca 32

<210> SEQ ID NO 129
<211> LENGTH: 32
<212> TYPE: DNA
<213> ORGANISM: Artificial Sequence
<220> FEATURE:
<223> OTHER INFORMATION: Synthetic DNA

<400> SEQUENCE: 129
tgattttgaa aggatctgac tgtatgttta tg 32

<210> SEQ ID NO 130
<211> LENGTH: 500
<212> TYPE: DNA
<213> ORGANISM: Stevia rebaudiana

<400> SEQUENCE: 130
aatcagtcca atttaaacgt gctctactta cagagttatg atatttatta aggcactaaa 60
acatgaaact gacgtgacga attgaaagat tattccaatc ttgatccatt ttgccactta 120
aaacaagatg aagataacat aaaaaagatc ggaaaaaaat gataccatgt aaacgaatac 180
gaaacaacat aaaacaatta ggtacccttg agttttgatt tcctggtaaa aactaaataa 240
aaaacacatt aattcacaac aaacgattat gaccggtgaa gaaaaagatt ggaacagatg 300
atgaaggaat aacatattct cctgatgatc gatgatagat gagaaattgg ggtattaagg 360
tttgcaattc caaaggaatt cgtcagatag gagaaactga aaacagaata tcatgtctta 420
tttaaaaaaa acgggtatga gtttgtgttt gtgggttttt gggttaaata tgaattgagt 480
tactctgatg aagagaagtg 500

<210> SEQ ID NO 131
<211> LENGTH: 39
<212> TYPE: DNA
<213> ORGANISM: Artificial Sequence
<220> FEATURE:
<223> OTHER INFORMATION: Synthetic DNA

<400> SEQUENCE: 131
aatcagtcca atttaaacgt gctctactta cagagttat 39

<210> SEQ ID NO 132
<211> LENGTH: 29
<212> TYPE: DNA
<213> ORGANISM: Artificial Sequence
<220> FEATURE:
<223> OTHER INFORMATION: Synthetic DNA

<400> SEQUENCE: 132
cacttctctt catcagagta actcaattc 29

<210> SEQ ID NO 133
<211> LENGTH: 500
<212> TYPE: DNA
<213> ORGANISM: Stevia rebaudiana

<400> SEQUENCE: 133
aatcagtcca atttaaacgt gctctactta cagagttatc atatttatta aggcactaaa 60
acatgaaact gacgtgacga attgaaagat tattccaatc ttgatccatt ttgccactta 120
aaacaagatg aagataacat aaaaaagatc ggaaaaaaat gataccatgt aaacgaatac 180
gaaacaacat aaaacaatta ggtacccttg agttttgatt tcctggtaaa aactaaataa 240
aaaacacatt aattcacaac aaacgattat gaccggtgaa gaaaaagatt ggaacagatg 300
atgaaggaat aacatattct cctgatgatc gatgatagat gagaaattgg ggtattaagg 360
tttgcaattc caaaggaatt cgtcagatag gagaaactga aaacagaata tcatgtctta 420
tttaaaaaaa acgggtatga gtttgtgttt gtgggttttt gggttaaata tgaattgagt 480
tactctgatg aagagaagtg 500

<210> SEQ ID NO 134
<211> LENGTH: 21
<212> TYPE: DNA
<213> ORGANISM: Stevia rebaudiana

<400> SEQUENCE: 134
acagagttat catatttatt a 21

<210> SEQ ID NO 135
<211> LENGTH: 41
<212> TYPE: DNA
<213> ORGANISM: Stevia rebaudiana

<400> SEQUENCE: 135
tgctctactt acagagttat catatttatt aaggcactaa a 41

<210> SEQ ID NO 136
<211> LENGTH: 61

<212> TYPE: DNA
<213> ORGANISM: Stevia rebaudiana

<400> SEQUENCE: 136
aatttaaacg tgctctactt acagagttat catatttatt aaggcactaa aacatgaaac 60
t 61

<210> SEQ ID NO 137
<211> LENGTH: 39
<212> TYPE: DNA
<213> ORGANISM: Artificial Sequence
<220> FEATURE:
<223> OTHER INFORMATION: Synthetic DNA

<400> SEQUENCE: 137
aatcagtcca atttaaacgt gctctactta cagagatat 39

<210> SEQ ID NO 138
<211> LENGTH: 29
<212> TYPE: DNA
<213> ORGANISM: Artificial Sequence
<220> FEATURE:
<223> OTHER INFORMATION: Synthetic DNA

<400> SEQUENCE: 138
cacttctctt catcagagta actcaattc 29

<210> SEQ ID NO 139
<211> LENGTH: 500
<212> TYPE: DNA
<213> ORGANISM: Artificial Sequence
<220> FEATURE:
<223> OTHER INFORMATION: Synthetic DNA

<400> SEQUENCE: 139
aatcagtcca atttaaacgt gctctactta cagagatatc atatttatta aggcactaaa 60
acatgaaact gacgtgacga attgaaagat tattccaatc ttgatccatt ttgccactta 120
aaacaagatg aagataacat aaaaaagatc ggaaaaaaat gataccatgt aaacgaatac 180
gaaacaacat aaaacaatta ggtacccttg agttttgatt tcctggtaaa aactaaataa 240
aaaacacatt aattcacaac aaacgattat gaccggtgaa gaaaaagatt ggaacagatg 300
atgaaggaat aacatattct cctgatgatc gatgatagat gagaaattgg ggtattaagg 360
tttgcaattc caaaggaatt cgtcagatag gagaaactga aaacagaata tcatgtctta 420
tttaaaaaaa acgggtatga gtttgtgttt gtgggttttt gggttaaata tgaattgagt 480
tactctgatg aagagaagtg 500

<210> SEQ ID NO 140
<211> LENGTH: 500
<212> TYPE: DNA
<213> ORGANISM: Artificial Sequence
<220> FEATURE:
<223> OTHER INFORMATION: Synthetic DNA

<400> SEQUENCE: 140
aatcagtcca atttaaacgt gctctactta cagagatatg atatttatta aggcactaaa 60
acatgaaact gacgtgacga attgaaagat tattccaatc ttgatccatt ttgccactta 120
aaacaagatg aagataacat aaaaaagatc ggaaaaaaat gataccatgt aaacgaatac 180
gaaacaacat aaaacaatta ggtacccttg agttttgatt tcctggtaaa aactaaataa 240
aaaacacatt aattcacaac aaacgattat gaccggtgaa gaaaaagatt ggaacagatg 300
atgaaggaat aacatattct cctgatgatc gatgatagat gagaaattgg ggtattaagg 360
tttgcaattc caaaggaatt cgtcagatag gagaaactga aaacagaata tcatgtctta 420
tttaaaaaaa acgggtatga gtttgtgttt gtgggttttt gggttaaata tgaattgagt 480
tactctgatg aagagaagtg 500

<210> SEQ ID NO 141
<211> LENGTH: 37
<212> TYPE: DNA
<213> ORGANISM: Artificial Sequence
<220> FEATURE:
<223> OTHER INFORMATION: Synthetic DNA

<400> SEQUENCE: 141
aatcagtcca atttaaacgt gctctactta cagagat 37

<210> SEQ ID NO 142
<211> LENGTH: 463
<212> TYPE: DNA
<213> ORGANISM: Artificial Sequence
<220> FEATURE:
<223> OTHER INFORMATION: Synthetic DNA

<400> SEQUENCE: 142
atcatattta ttaaggcact aaaacatgaa actgacgtga cgaattgaaa gattattcca 60
atcttgatcc attttgccac ttaaaacaag atgaagataa cataaaaaag atcggaaaaa 120
aatgatacca tgtaaacgaa tacgaaacaa cataaaacaa ttaggtaccc ttgagttttg 180
atttcctggt aaaaactaaa taaaaaacac attaattcac aacaaacgat tatgaccggt 240
gaagaaaaag attggaacag atgatgaagg aataacatat tctcctgatg atcgatgata 300
gatgagaaat tggggtatta aggtttgcaa ttccaaagga attcgtcaga taggagaaac 360
tgaaaacaga atatcatgtc ttatttaaaa aaaacgggta tgagtttgtg tttgtgggtt 420
tttgggttaa atatgaattg agttactctg atgaagagaa gtg 463

<210> SEQ ID NO 143
<211> LENGTH: 21
<212> TYPE: DNA
<213> ORGANISM: Stevia rebaudiana

<400> SEQUENCE: 143
acagagttat gatatttatt a 21

<210> SEQ ID NO 144
<211> LENGTH: 41
<212> TYPE: DNA
<213> ORGANISM: Stevia rebaudiana

<400> SEQUENCE: 144
tgctctactt acagagttat gatatttatt aaggcactaa a 41

<210> SEQ ID NO 145
<211> LENGTH: 61
<212> TYPE: DNA
<213> ORGANISM: Stevia rebaudiana

<400> SEQUENCE: 145
aatttaaacg tgctctactt acagagttat gatatttatt aaggcactaa aacatgaaac 60
t 61

```
<210> SEQ ID NO 146
<211> LENGTH: 39
<212> TYPE: DNA
<213> ORGANISM: Artificial Sequence
<220> FEATURE:
<223> OTHER INFORMATION: Synthetic DNA

<400> SEQUENCE: 146

aatcagtcca atttaaacgt gctctactta cagaggtat                          39


<210> SEQ ID NO 147
<211> LENGTH: 39
<212> TYPE: DNA
<213> ORGANISM: Artificial Sequence
<220> FEATURE:
<223> OTHER INFORMATION: Synthetic DNA

<400> SEQUENCE: 147

aatcagtcca atttaaacgt gctctactta cagagtgat                          39


<210> SEQ ID NO 148
<211> LENGTH: 39
<212> TYPE: DNA
<213> ORGANISM: Artificial Sequence
<220> FEATURE:
<223> OTHER INFORMATION: Synthetic DNA

<400> SEQUENCE: 148

aatcagtcca atttaaacgt gctctactta cagagttaa                          39
```